US009005923B2

(12) United States Patent
Soetaert et al.

(10) Patent No.: US 9,005,923 B2
(45) Date of Patent: Apr. 14, 2015

(54) **USE OF *CANDIDA BOMBICOLA* STRAINS MODIFIED IN THEIR SOPHOROLIPID PRODUCTION**

(75) Inventors: Wim Soetaert, Lovendegem (BE); Sofie De Maeseneire, Destelbergen (BE); Karen Saerens, Drongen (BE); Sophie Roelants, Ghent (BE); Inge Van Bogaert, Overmere (BE)

(73) Assignee: Universiteit Gent, Ghent (BE)

( * ) Notice: Subject to any disclaimer, the term of this patent is extended or adjusted under 35 U.S.C. 154(b) by 189 days.

(21) Appl. No.: 13/701,784

(22) PCT Filed: Jun. 10, 2011

(86) PCT No.: PCT/EP2011/059683
§ 371 (c)(1),
(2), (4) Date: Dec. 3, 2012

(87) PCT Pub. No.: WO2011/154523
PCT Pub. Date: Dec. 15, 2011

(65) Prior Publication Data
US 2013/0089892 A1    Apr. 11, 2013

(30) Foreign Application Priority Data
Jun. 11, 2010  (GB) .................................. 1009882.0

(51) Int. Cl.
| | |
|---|---|
| C12P 7/64 | (2006.01) |
| C12P 19/44 | (2006.01) |
| C12N 9/02 | (2006.01) |
| C12N 15/81 | (2006.01) |

(52) U.S. Cl.
CPC ............. *C12N 15/815* (2013.01); *C12N 9/0071* (2013.01); *C12P 7/64* (2013.01); *C12P 7/6409* (2013.01); *C12P 19/44* (2013.01)

(58) Field of Classification Search
CPC ............ C12P 19/44; C12P 19/18; C12P 7/64; C12P 7/6409; C12P 19/12; C12P 19/305; C12N 15/815; C12N 9/0071; C12N 15/52; C12N 15/70; C12N 15/81; C12N 9/1051; C07K 14/40
USPC .......... 435/69.1, 134, 41, 254.2, 254.22, 189, 435/193
See application file for complete search history.

(56) References Cited

U.S. PATENT DOCUMENTS 8,158,391 B2 * 4/2012 Gross et al. .................... 435/134

FOREIGN PATENT DOCUMENTS

| WO | WO 2009/141407 | 11/2009 |
|---|---|---|
| WO | WO 2011/061032 | 5/2011 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Saerens, et al. "Identification of the UDP-glucosyltransferase Gene *UGTA1*, Responsible for the First Glycosylation Step in the Sophorolipid Biosynthetic Pathway of *Candida bombicola* ATCC 22214," *FEMS Yeast Research*, vol. 11, No. 1, pp. 123-132, Feb. 1, 2011.
Saerens, et al. "Cloning and Functional Characterization of the UDP-glycosyltransferase UgtB I Involved in Sophorolipid Production by *Candida bombicola* and Creation of a Glucolipid-producing Yeast Strain," *Yeast*, vol. 28, No. 4, pp. 279-292, Apr. 1, 2011.
Van Bogaert, et al. "Knocking out the *MFE-2* Gene of *Candida bombicola* Leads to Improved Medium-chain Sophorolipid Production," *FEMS Yeast Research*, vol. 9, No. 4, pp. 610-617, Jun. 1, 2009.
Breithaupt, et al. "Affinity Chromatography and Further Characterization of the Glucosyltransferases Involved in Hydroxydocosanoic Acid Sophoroside Production in *Candida bogoriensis*," *Journal of Biological Chemistry*, vol. 257, No. 16, pp. 9622-9628, Aug. 25, 1982.
Esders, et al. Glucosyl- and Acetyltransferases Involved in the Biosynthesis of Glycolipids from *Candid bogoriensis, The Journal of Biological Chemistry*, vol. 245, No. 5, pp. 1375-1386, Mar. 10, 1972.
Van Bogaert, et al. "Importance of the Cytochrome P450 Monooxygenase CYP52 family for the Sophorolipid-producing Yeast *Candida bombicola*," *FEMS Yeast Research*, vol. 9, No. 1, pp. 87-94, Feb. 1, 2009.
Hewald, et al. "Genetic Analysis of Biosurfactant Production in *Ustilago maydis*," *Applied and Environmental Microbiology*, vol. 71, No. 6, pp. 3033-3040, Jun. 1, 2005.
Van Bogaert, et al. "Microbial Production and Application of Sophorolipids," *Applied Microbiology and Biotechnology*, vol. 76, No. 1, pp. 23-34, May 3, 2007.
Lottermoser, et al. "Cytochromes P450 of the Sophorose Lipid-producing Yeast *Candida apicola*: Heterogeneity and Polymerase Chain Reaction-mediated Cloning of Two Genes," *Yeast*, vol. 12, No. 6, pp. 565-575, Jan. 1, 1996.
Van Bogaert, et al. "Cerulenin Inhibits de novo Sophorolipid Synthesis of *Candida bombicola*," *Biotechnology Letters*, vol. 30, No. 10, pp. 1829-1832, Jun. 21, 2008.
Van Bogaert, et al. "Development of a Transformation and Selection System for the Glycolipid-producing Yeast *Candida bombicola*," *Yeast*, vol. 25, No. 4, pp. 273-278, Apr. 1, 2008.
International Search Report dated Nov. 15, 2011 issued to priority international application No. PCT/EP2011/059683.

* cited by examiner

*Primary Examiner* — Delia Ramirez
(74) *Attorney, Agent, or Firm* — Knobbe, Martens, Olson & Bear LLP

(57) ABSTRACT

The present invention relates to yeast species which are normally capable of producing sophorolipids but which are modified in such way that they are incapable producing the latter compounds. These sophorolipid-negative strains surprisingly display equal growth characteristics and biomass formation as their wild type counterparts and are hence useful for the production of compounds such as recombinant proteins, glycolipids, polyhydroxyalkanoates and carotenoides. In addition, the present invention discloses two glucosyltransferase genes with key-functions in sophorolipid production.

4 Claims, 17 Drawing Sheets

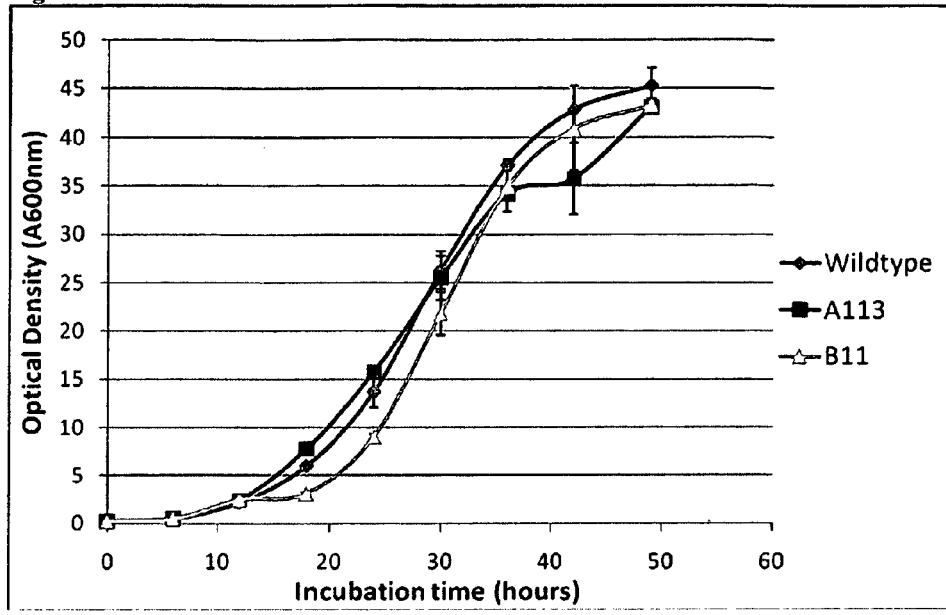

```
  1  cagatatgca tcaggggcac agactaaaag ctgctctcag cgagtaccct tacctcttga
 61  gaaccctcaa aatttaccca gcctgcagca tatcatgcac catggttaaa ttcggaaatg
121  aatttaccgg tggccttgaa ccacgttcct ccaattattt aaggcaataa cctgccactc
181  tcttgatttg attaagaaag actttcaatt tagcttctcc ctacgaatat tcaatgagcc
                                                                    M  S
241  cttcatcaca caaacccctg attctcgctt gcggcttgcc tctttcaggc catataatgc
      P  S  S  H  K  P  L  I  L  A  C  G  L  P  L  S  G  H  I  M
301  ccgttttgag tctggtacac ggccttacgg acgacggata cgaagctact gttgtgacag
      P  V  L  S  L  V  H  G  L  T  D  D  G  Y  E  A  T  V  V  T
361  gcagagcgtt tgaacaaaaa gttcgagatg tgggtgcaga ctttgttcct ttagaaggga
      G  R  A  F  E  Q  K  V  R  D  V  G  A  D  F  V  P  L  E  G
421  acgcagattt tgatgaccac accttagacg atctggtccc gggccgtaaa gacatggccc
      N  A  D  F  D  D  H  T  L  D  D  L  V  P  G  R  K  D  M  A
481  caagcttcga tcgtacagtt caagatgtgg agcacatgat ggtagctact cttcctgagc
      P  S  F  D  R  T  V  Q  D  V  E  H  M  M  V  A  T  L  P  E
541  agtttgccgc tattcagagg gctttcaaaa agctcagcgc aagcggccgc cctgtcgttc
      Q  F  A  A  I  Q  R  A  F  K  K  L  S  A  S  G  R  P  V  V
601  ttgtcagtga agtgctgttt ttcggtgcac accctatcag cctcggtgct cctggtttca
      L  V  S  E  V  L  F  F  G  A  H  P  I  S  L  G  A  P  G  F
```

Figure 3 cont.

```
 661  aacccgctgg ctggatttgt ttaggggttt tgcctctttt gatccgcagt gatcatacct
        K   P   A   G   W   I   C   L   G   V   L   P   L   L   I   R   S   D   H   T
 721  taggacttga caacgacagg agccccgaag cacatgcaaa gaaactcgct atgaaccacg
        L   G   L   D   N   D   R   S   P   E   A   H   A   K   K   L   A   M   N   H
 781  ctcttgagca ccaaattttc gttaaagcca ctgctaagca caaggaaatc tgccgagagt
        A   L   E   H   Q   I   F   V   K   A   T   A   K   H   K   E   I   C   R   E
 841  taggttgcac tgaagatccc aaatttatct gggagcacag ttacattgct gcagacaagt
        L   G   C   T   E   D   P   K   F   I   W   E   H   S   Y   I   A   D   K
 901  tcctgcagct gtgcccgcct tctcttgagt tcagcagaga ccatctgcct agcaacttca
        F   L   Q   L   C   P   P   S   L   E   F   S   R   D   H   L   P   S   N   F
 961  aattcgccgg ctcaacgccc aagcaccgaa ctcaattcac ccctccttcc tggtgggggg
        K   F   A   G   S   T   P   K   H   R   T   Q   F   T   P   P   S   W   W   G
1021  atgttctgag tgccaagcga gtcatcatgg tcactcaagg aactttgct  gtcagttaca
        D   V   L   S   A   K   R   V   I   M   V   T   Q   G   T   F   A   V   S   Y
1081  agcatcttat tgtgcctact cttgaggcct tgaaggacga gcctgacact taacagtag
        K   H   L   I   V   P   T   L   E   A   L   K   D   E   P   D   T   L   T   V
1141  ccatattggg ccgccgcggt gccaagctac cggatgatgt tgtggttcct gagaatgctc
        A   I   L   G   R   R   G   A   K   L   P   D   D   V   V   V   P   E   N   A
1201  gcgtgatcga ctactcaac tacgatgctc tacttcctca cgttgatgct cttgtctaca
        R   V   I   D   Y   F   N   Y   D   A   L   L   P   H   V   D   A   L   V   Y
1261  atggtggata tggcggactt cagcacagct taagccactc tgttccagtt gttattgctg
        N   G   G   Y   G   G   L   Q   H   S   L   S   H   S   V   P   V   V   I   A
1321  gtgactctga agacaagcca atggtggcat cgagagctga ggccgctggc gtggcaattg
        G   D   S   E   D   K   P   M   V   A   S   R   A   E   A   A   G   V   A   I
1381  atttgaaaac tggcttgcct acagtggagc aaatcaaaga agctgttgat tcgataattg
        D   L   K   T   G   L   P   T   V   E   Q   I   K   E   A   V   D   S   I   I
1441  gaaatccgaa attccacgaa gcctcgaaga aggttcaaat ggagttggaa agccacaact
        G   N   P   K   F   H   E   A   S   K   K   V   Q   M   E   L   E   S   H   N
1501  ccttgaaaat tcttgaggaa agcatcgagg aaatcgccag ccatgacttt ggtcttttga
        S   L   K   I   L   E   E   S   I   E   E   I   A   S   H   D   F   G   L   L
1561  ccaagagtga cgaggaaact gaagatatac ctgtcaaagg gccggcctta gcggtgagtt
        T   K   S   D   E   E   T   E   D   I   P   V   K   G   P   A   L   A   V   S
1621  cttagaatcg tacgatcaaa tcagatcagg gaagagaggt agggttttt  ttatttatgt
        S   -
1681  ctttgttttt attgattgaa atttacaata caacaaccat caaattaatt tgaacaaaca
1741  acaacacaca cacactgcaa cttcaaaaa  aataagta
```

Figure 6

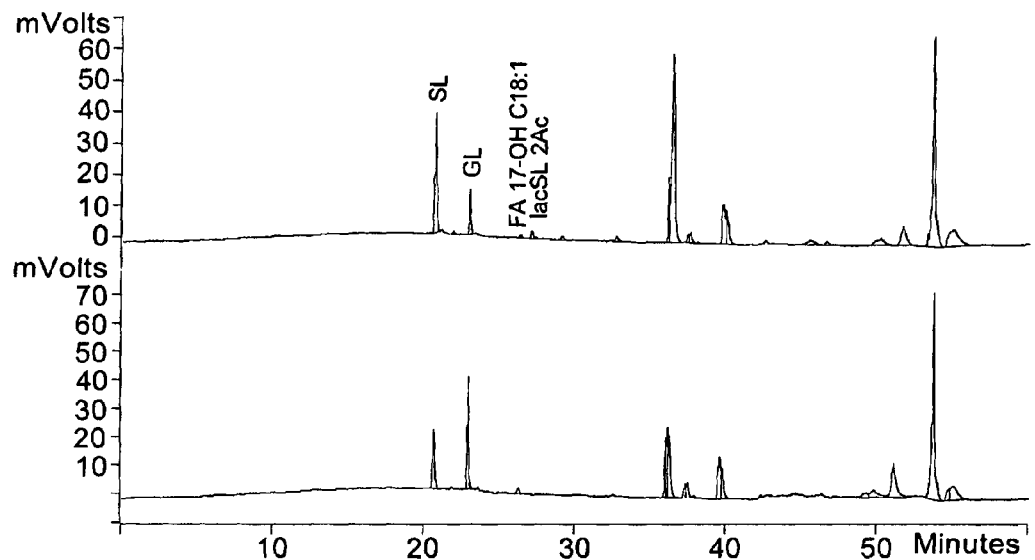

Figure 7

```
        GTII -472For
  1  gagagtggga cctgattcag aatcacacgg acccgtatat ataacaatca ctttccaaca atatagcgag
 71  tattaatata tttccgggta agggttgttc cggacttatg catttaatca caggttgcat cagctaaata
141  tgtcagggcc gacggcgtaa atttagaagg ttaggtcaag atccatcggt caggccaatg gagctctact
211  atgataggca gctgaagcga gacaagatat acttcagttg cgctctctga aaaaattatt ttgtgattct
281  cactcagtgg atgtggcgac acacggaacc aataatctcg ccggaaaggc ggctgaacat cagtcttgca
351  taagtgtgca agtggcctga gcacagcgtg cattacccctt accatacatt cggggcaagt taaatccagc
421  attatataaa cttgattgac acaaatgggc ataaaacaat aaagtctcct atatggccat cgagaaacca
                                                                        M  A  I  E  K  P
491  gtgatagttg cttgtgcctg cccactagcg gggcacgtgg gcccagtgct cagcctggtc cgcggtctac
      V  I  V  A  C   A  P  L  A  G   H  V  G  P  V   L  S  L  V  R   G  L
561  tcaatagagg atatgaggtg actttcgtaa cagggaacgc attcaaggag aaagttattg aggcaggatg
      L  N  R  G   Y  E  V  T  F   V  T  G  N  A   F  K  E  K  V   I  E  A  G
631  cactttcgtc cctctccaag gacgagctga ctaccatgaa tacaatctcc ctgaaatcgc tccaggattg
      C  T  F  V  P   L  Q  G  R  A   D  Y  H  E  Y   N  L  P  E  I   A  P  G  L
701  ctcacgattc ctccaggcct tgagcagacc ggttactcaa tgaatgagat ttttgtgaag gcgattcctg
      L  T  I  P   P  G  L  E  Q   T  G  Y  S  M   N  E  I  F  V   K  A  I  P
771  agcagtacga tgcacttcaa actgctctaa aacaggttga ggctgaaaat aaatcagctg tggtgattgg
      E  Q  Y  D   A  L  Q  T  A   L  K  Q  V  E   A  E  N  K  S   A  V  V  I
841  cgagaccatg tttctagggg tgcatccgat atcactgggt gccccaggtc tcaagcccca aggcgtaatc
      G  E  T  M  F   L  G  V  H  P   I  S  L  G  A   P  G  L  K  P   Q  G  V  I
911  acgttaggaa ctattccgtc catgctgaaa gcagagaagg cgcctggagt tcctagtctt gagccaatga
      T  L  G  T   I  P  C  M  L   K  A  E  K  A   P  G  V  P  S   L  E  P  M
```

Figure 7 cont.

```
 981 ttgatacttt agtgcggcaa caagtatttc aaccaggaac tgactctgag aaggagatca tgaagacgct
      I  D  T   L  V  R  Q   Q  V  F   Q  P  G   T  D  S  E   K  E  I   M  K  T
1051 cggggccacg aaggagcccg aatttctcct ggagaatata tacagcagcc ctgacagatt tttgcaactg
      L  G  A  T   K  E  P   E  F  L   L  E  N  I   Y  S  S   P  D  R   F  L  Q  L
1121 tgccctccat ctcttgaatt tcacttgact tcgcctcctc ctggcttctc gttcgctggt agtgcaccgc
      C  P  P   S  L  E   F  H  L  T   S  P  P   P  G  F   S  F  A  G   S  A  P
1191 atgtaaagtc tgctggatta gcaactccac ctcacctgcc gtcttggtgg cctgatgtgc tgagtgcgaa
      H  V  K   S  A  G  L   A  T  P   P  H  L   P  S  W  W   P  D  V   L  S  A
1261 gcgtctgatt gttgttacac aaggaacagc agccatcaac tatgaagatc tgctcattcc agcattgcag
      K  R  L  I   V  V  T   Q  G  T   A  A  I  N   Y  E  D   L  L  I   P  A  L  Q
1331 gcctttgctg acgaagaaga cactctcgta gttggtatat gggcgtcaa aggggcgtca cttcctgata
      A  F  A   D  E  E   D  T  L  V   V  G  I   L  G  V   K  G  A   S  L  P  D
1401 gcgttaaagt tcctgcaaac gctcgaattg ttgattattt tccttacgat gagctactac cgcatgcctc
      S  V  K   V  P  A  N   A  R  I   V  D  Y   F  P  Y  D   E  L  L   P  H  A
1471 tgttttcata tacaacggtg gatacggagg tctgcagcac agtttgagcc atggcgttcc cgtcatcatc
      S  V  F  I   Y  N  G   G  Y  G   G  L  Q  H   S  L  S   H  G  V   P  V  I  I
1541 ggaggaggaa tgttggtaga caagccagct gttgcttcac gagctgtatg ggctggtgtt ggttatgatc
      G  G  G   M  L  V   D  K  P  A   V  A  S   R  A  V   W  A  G  V   G  Y  D
1611 ttcaaaccct gcaggcaact tctgagctag tctccacggc cgttaaggag gtgttggcta ctccctcgta
      L  Q  T   L  Q  A  T   S  E  L   V  S  T   A  V  K  E   V  L  A   T  P  S
1681 tcacgagaaa gccatggcag tcaagaaaga gcttgaaaaa tacaagtctc ttgatattct agagtcggca
      Y  H  E  K   A  M  A   V  K  K   E  L  E  K   Y  K  S   L  D  I   L  E  S  A
1751 attagtgaat tagcttctta acctggctct ttttctagat atgtctgcgc cctgctcact gcttactggc
      I  S  E   L  A  S   -
1821 ctaagctggt attacggacc ttaatcaagt atcaccccaa ggcaatcgag agtcttatcg agtctctagg
1891 tagatagata cacgttttga ttttcggcc cactttgtag aaaaatctca gtgatttcat ggaattcagt
1961 tacaaatact aatctgataa accaagaact_acactcggtg_ttgagagcag
                                    GTII +239Rev
```

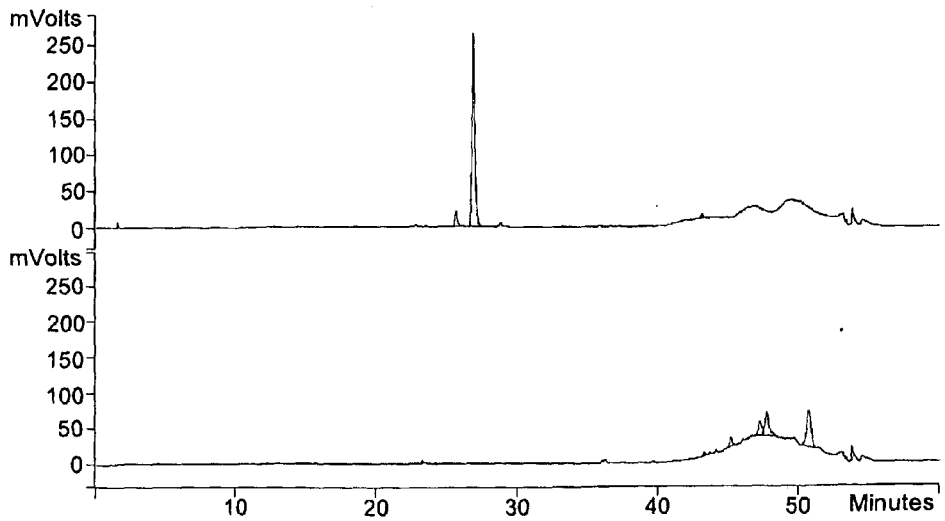

Figure 14

```
   1  gcgcgccgcg aaacggttag tataagcagt acgacgttgt tgctggagtc tcatctgcaa
      >>..............................pGAPD...............................>
  61  ggttgagtac caatccctgc cccaatacga gcaatcgaag ccttggggaa agatgcggcg
      >................................pGAPD...............................>
 121  ggctagcttc agcaataaat agcaggcgac acacaaaaat taggcggcaa gcgcacgctc
      >................................pGAPD...............................>
 181  agcatgccat ctaccagggc aaaaagcaag gcaacctctt tttcgcatcc cgatttagag
      >................................pGAPD...............................>
 241  cctaccgtc attgcaggt gtgcgtctac gatataacac gatcgacatc gcgctgggta
      >................................pGAPD...............................>
 301  tgcttctggg taagggctcg caacgtgtga gttgtcagca ctggccgata cccaaagtat
      >................................pGAPD...............................>
 361  ataatgcgcc gttgaacggt tatagtcggt caagctctta agaaagact taagaacaaa
      >................................pGAPD...............................>
 421  aacaactgta cacatatgcg tttcctagc attttactg ctgttctttt cgctgctagc
                              m   r   f   p   s   i   f   t   a   v   l   f   a   a   s
      >....pGAPD.....><..................sMFaScss..........................>
 481  agcgctcttg ctgctccagt taacactaca acagaggatg agactgctca gattccggct
       s   a   l   a   a   p   v   n   t   t   e   d   e   t   a   q   i   p   a
      >...........................sMFaScss..................................>
 541  gaggctgtta ttggttacag cgatcttgag ggcgatttcg atgttgctgt tcttccattt
       e   a   v   i   g   y   s   d   l   e   g   d   f   d   v   a   v   l   p   f
      >...........................sMFaScss..................................>
 601  agcaacagca caaataacgg ccttcttttt ataaatacta ctattgctag cattgctgct
       s   n   s   t   n   n   g   l   l   f   i   n   t   i   a   s   i   a   a
      >...........................sMFaScss..................................>
 661  aaggaggagg gcgtttctct tgataagcgt gctactcctg ctgactggcg ttcgcagagc
       k   e   e   g   v   s   l   d   k   r   a   t   p   a   d   w   r   s   q   s
      >........sMFaScss..............><..............sAmyAO..................>
 721  atttatttcc ttctcactga tcgttttgct cgtactgatg gctcgactac tgctacttgc
       i   y   f   l   l   t   d   r   f   a   r   t   d   g   s   t   a   t   c
      >...........................sAmyAO....................................>
 781  aatactgctg atcgtaagta ctgcggtgga acatggcagg gcattattga caagcttgac
       n   t   a   d   r   k   y   c   g   g   t   w   q   g   i   i   d   k   l   d
      >...........................sAmyAO....................................>
 841  tatattcagg gaatgggctt cacagctatt tggattaccc ccgttacagc tcagctgccc
       y   i   q   g   m   g   f   t   a   i   w   i   t   p   v   t   a   q   l   p
      >...........................sAmyAO....................................>
 901  cagaccaccg cttatggaga tgcttaccac ggctactggc agcaggatat ttactctctg
       q   t   t   a   y   g   d   a   y   h   g   y   w   q   q   d   i   y   s   l
      >...........................sAmyAO....................................>
 961  aacgagaact acggcactgc tgatgacctt aaggctctct cttcggctct tcacgagcgt
       n   e   n   y   g   t   a   d   d   l   k   a   l   s   s   a   l   h   e   r
      >...........................sAmyAO....................................>
1021  ggcatgtatc ttatggttga tgttgttgct aaccacatgg gctatgatgg agctggtagc
       g   m   y   l   m   v   d   v   v   a   n   h   m   g   y   d   g   a   g   s
      >...........................sAmyAO....................................>
1081  agcgttgatt actctgtttt taagccgttc tctagccagg actacttcca cccgttctgc
       s   v   d   y   s   v   f   k   p   f   s   s   q   d   y   f   h   p   f   c
      >...........................sAmyAO....................................>
1141  ctcattcaga actatgagga tcagactcag gttgaggatt gctggctcgg agataacact
       l   i   q   n   y   e   d   q   t   q   v   e   d   c   w   l   g   d   n   t
      >...........................sAmyAO....................................>
```

Figure 14 cont.

```
1201  gttagccttc ctgatctcga taccaccaag gatgttgtta agaatgagtg gtacgactgg
       v  s  l  p  d  l  d  t  t  k  d  v  v  k  n  e  w  y  d  w
      >..................sAmyAO..............................>
1261  gttggaagcc ttgtttcgaa ctacagcatt gacggcctcc gtattgacac agttaagcac
       v  g  s  l  v  s  n  y  s  i  d  g  l  r  i  d  t  v  k  h
      >..................sAmyAO..............................>
1321  gttcagaagg acttctggcc cggctacaac aaggctgctg gcgtttactg cattggcgag
       v  q  k  d  f  w  p  g  y  n  k  a  a  g  v  y  c  i  g  e
      >..................sAmyAO..............................>
1381  gttctcgacg gtgatccggc ttacacttgc cctaccaga acgttatgga cggcgttctg
       v  l  d  g  d  p  a  y  t  c  p  y  q  n  v  m  d  g  v  l
      >..................sAmyAO..............................>
1441  aactatccca tttactatcc actcctcaac gctttcaaga gcaccagcgg cagcatggac
       n  y  p  i  y  y  p  l  l  n  a  f  k  s  t  s  g  s  m  d
      >..................sAmyAO..............................>
1501  gacctctaca acatgattaa caccgttaag agcgactgcc cagacagcac actcctgggc
       d  l  y  n  m  i  n  t  v  k  s  d  c  p  d  s  t  l  l  g
      >..................sAmyAO..............................>
1561  acattcgttg agaaccacga caacccacgt ttcgcttctt acaccaacga cattgctctc
       t  f  v  e  n  h  d  n  p  r  f  a  s  y  t  n  d  i  a  l
      >..................sAmyAO..............................>
1621  gctaagaacg ttgctgcttt cattattctc aacgacggaa ttcccattat ttacgctggc
       a  k  n  v  a  a  f  i  i  l  n  d  g  i  p  i  i  y  a  g
      >..................sAmyAO..............................>
1681  caggagcagc actacgctgg cggaaacgac cccgctaacc gtgaggctac ctggctctcg
       q  e  q  h  y  a  g  g  n  d  p  a  n  r  e  a  t  w  l  s
      >..................sAmyAO..............................>
1741  ggctacccga ccgacagcga gctgtacaag cttattgcta gcgctaacgc tattcgtaac
       g  y  p  t  d  s  e  l  y  k  l  i  a  s  a  n  a  i  r  n
      >..................sAmyAO..............................>
1801  tatgctatta gcaaggatac aggattcgtt acctacaaga actggcccat ttacaaggac
       y  a  i  s  k  d  t  g  f  v  t  y  k  n  w  p  i  y  k  d
      >..................sAmyAO..............................>
1861  gacacaacta ttgctatgcg taagggcaca gatggctcgc agattgttac tattcttagc
       d  t  t  i  a  m  r  k  g  t  d  g  s  q  i  v  t  i  l  s
      >..................sAmyAO..............................>
1921  aacaagggtg cttcgggtga ttcgtatacc ctcagccttt ctggtgctgg ttacacagct
       n  k  g  a  s  g  d  s  y  t  l  s  l  s  g  a  g  y  t  a
      >..................sAmyAO..............................>
1981  ggccagcagc ttactgaggt tattggctgc actaccgtta ctgttggttc ggatggaaat
       g  q  q  l  t  e  v  i  g  c  t  t  v  t  v  g  s  d  g  n
      >..................sAmyAO..............................>
2041  gttcctgttc ctatggctgg tggcctccct cgtgttcttt atccgactga gaagcttgct
       v  p  v  p  m  a  g  g  l  p  r  v  l  y  p  t  e  k  l  a
      >..................sAmyAO..............................>
2101  ggtagcaaga tttgctctag ctcgtgataa gcccgggcgc cggcgtacga tta(SEQ ID NO 64)
       g  s  k  i  c  s  s  s  -   -(SEQ ID NO 65)
      >..........sAmyAO..........>>
```

USE OF *CANDIDA BOMBICOLA* STRAINS MODIFIED IN THEIR SOPHOROLIPID PRODUCTION

CROSS-REFERENCE TO RELATED APPLICATIONS

This application is the U.S. National Phase under 35 U.S.C. §371 of International Application PCT/EP2011/059683, filed Jun. 10, 2011, which claims priority to GB 1009882.0, filed Jun. 11, 2010.

REFERENCE TO SEQUENCE LISTING

This application incorporates by reference the sequence listing submitted as ASCII text filed via EFS-Web on Jan. 13, 2015. The Sequence Listing is provided as a file entitled "seqlstUSdecle176004apc.txt," created on Jan. 8, 2015, and which is approximately 38 kilobytes in size.

TECHNICAL FIELD OF INVENTION

The present invention relates to yeast species which are normally capable of producing sophorolipids but which are so modified that they become incapable of producing the latter compounds. These sophorolipid-negative strains surprisingly display equal growth characteristics and biomass formation as their wild type counterparts and are hence useful for the production of numerous useful compounds such as recombinant proteins, glycolipids, polyhydroxyalkanoates, special sugars, special fatty acids, squaleen, organic acids, hydrophobic compounds, and carotenoides. In addition, the present invention discloses two glucosyltransferase genes with key-functions in sophorolipid production and their use.

BACKGROUND ART

The non-pathogenic yeast *Candida bombicola* and other yeast species such as *Candida apicola*, *Candida batistae*, *Rhodotorula bogoriensis* and *Wickerhamiella domericqiae* are known for their sophorolipid production during stationary phase (Spencer et al., 1970, Gorin et al., 1961, Tulloch et al., 1968, EP0837140A1, U.S. Pat. No. 6,433,152, U.S. Pat. No. 4,215,213). *C. bombicola* and others are oleaginous yeast species, i.e. they can utilize oleaginous substrates such as alkanes and oils as carbon source, and can handle those substrates in relatively high concentrations. Moreover, *C. bombicola* can produce sophorolipids in high amounts (over 400 g/L), which are excreted in the fermentation medium.

*Candida bombicola* ATCC 22214 is already applied commercially for the production of sophorolipids. These glycolipid biosurfactants are constituted of a sophorose head group (2-O-β-D-glucopyranosyl-β-D-glucopyranose) from which the anomeric C-atom is attached to an (ω) or (ω-1) $C_{16}$ or $C_{18}$ hydroxylated fatty acid. They occur either as open-ring structures (acid form) or as lactones with an intra-esterification between the fatty acid carboxyl group and the 4", 6' or 6" carbon atom of the sophorose head group. In addition, acetyl groups can be attached at the 6' and/or 6" positions (Asmer et al., 1988).

In a typical *Candida bombicola* fermentation with e.g. rapeseed oil as a hydrophobic carbon source, sophorolipids are present as a complex mixture of structurally related molecules with the mono- and di-acetylated lactonic sophorolipids being the most important.

While many research has focused on fermentation conditions to optimize sophorolipid production by *C. bombicola* (Daniel et al., 1998a, Daniel et al., 1998b, Casas et al., 1999, Cavalero et al., 2003, Kim et al., 2009), and sophorolipids have served as substrates for (chemo)-enzymatic modifications (Bisht et al., 1999, Hu et al., 2003, Rau et al., 1999), the biochemical pathway of these economically important bioproducts remains unclear and there is no information available about the genes involved (Ochsner et al., 1994a, Ochsner et al., 1994b). This lack of information hampers implementation of modern techniques such as metabolic engineering to increase sophorolipid yields. The only data about enzymes involved in sophorolipid production by *C. bombicola* suggest the involvement of a cytochrome P450 monooxygenase from the CYP52 family (Van Bogaert et al., 2009). Data about enzymes in other yeasts are limited to protein experiments with *C. bogoriensis* lysates and date from early 1970's and 1980's (Esders et al., 1972, Bucholtz et al., 1976, Breithaupt et al., 1982). Apart from an acetyltransferase, it was assumed that two glucosyltransferases were involved in the stepwise production of sophorolipid by this organism, though separation of the two activities remained unsuccessful (Breithaupt et al., 1982).

Besides the fact that the biochemical pathway of the production of sophorolipids is largely unknown, *C. bombicola* will always produce sophorolipids no matter which carbon source is applied. Hence, the sophorolipids will always form a mixture with other compounds of potential interest and the biosynthetic pathway will compete for the use of substrates. Consequently, it is hardly impossible to combine the (recombinant) production of a compound of interest with the sophorolipid synthesis without substantial loss of efficiency and without additional purification costs. The option to only produce the compound of interest during the exponential growth phase when no or low amounts of sophorolipids are produced, will not only result in lower yields due to the lower amount of available biomass and shorter production time, but will also often result in a low tolerance of the growing cells towards the oleaginous substrates used. These problems are omitted when strains that lack this sophorolipid production are used. However, Ito and Inoue (Ito et al., 1982; Inoue et al., 1982) demonstrated that sophorolipids stimulate the growth on oleaginous substrates whereas a number of synthetic non-ionic surfactants have no effect. They further state that sophorolipids act as specific growth stimulating factors and are needed to emulsify the insoluble oleaginous substrates. Therefore, strains unable to produce sophorolipids show inferior growth as compared to the wild type and are unable to handle oleaginous substrates.

Taken together, it is clear that sophorolipid-producing yeast species might be very useful to produce, in addition to sophorolipids, other numerous useful compounds such as recombinant proteins, glycolipids, polyhydroxyalkanoates, sophorose, rhamnose, special fatty acids, squaleen, organic acids, hydrophobic compounds and oleagenious compounds. However, a lack of understanding of the underlying biochemical pathway of sophorolipid synthesis and the problem of combining the production of a useful compound of interest with the sophorolipid synthesis without substantial loss of efficiency and without additional purification costs seriously hamper the usage of these yeast species.

Description of Tables:
Table 1 Primers used for knocking-out the *C. bombicola* CYP52M1 gene. All primers were obtained from Sigma Genosys.
Table 2 Primers used for isolation of the UGTA1 gene and construction of the knock-out cassette. All primers were obtained from Sigma Genosys.

Table 3 Ten best homology scores for the translated UGTA1 sequence

Table 4 Primers used for isolation of the UGTB1 gene and construction of the knock-out cassette. All primers were obtained from Sigma Genosys.

Table 5 Ten best homology scores for the translated UGTB1 sequence

Table 6 Primers used for creation of the GFP expression cassette. All primers were obtained from Sigma Genosys. Bold characters represent non-binding extensions.

Table 7 Primers used for creating the amylase expression cassette and control of amylase transformants.

Table 8 Primers used for creating the PHA expression cassette. All primers were obtained from Sigma Genosys.

Table 9 Primers used for creation of the UGT1 and CepB expression cassettes. All primers were obtained from Sigma Genosys.

DESCRIPTION OF FIGURES

FIG. 2 Growth of *C. bombicola* wildtype, A113 (ugtA1 deletion mutant) and B11 (ugtB1 deletion mutant) in Lang medium. All cultures were inoculated from a Lang preculture in such a way that all the cultures started with OD 0.2.

FIG. 3 Complete DNA sequence of the UGTA1 gene (GenBank accession number HM440973, SEQ ID N0° 1). Putative promoter and terminator elements are indicated by boxes while a possible GATA-like regulatory motif is shaded in grey. The encoded amino acid sequence (SEQ ID N0° 2) of the Ugta1 glucosyltransferase protein is also depicted.

FIG. 8 Global pairwise alignment of *C. bombicola* UgtA1 (upper; SEQ ID NO: 2) and UgtB1 (lower; SEQ ID NO: 4) protein sequences. Similar amino acids are shaded in grey while identical residues are shaded in black. The 14 conserved residues of the GT1_Gtf_like domain are indicated by arrows down for UgtA1 and arrows up for UgtB1.

FIG. 9 HPLC-ELSD chromatograms from culture extracts, 7 days after incubation of *C. bombicola* ATCC22214 (up) and *C. bombicola* B11 (down) with rapeseed oil. De novo sophorolipids typically elute between 25 and 30 min. SL=sophorolipid, GL=glucolipid.

DETAILED DESCRIPTION OF THE INVENTION

Figure 1:
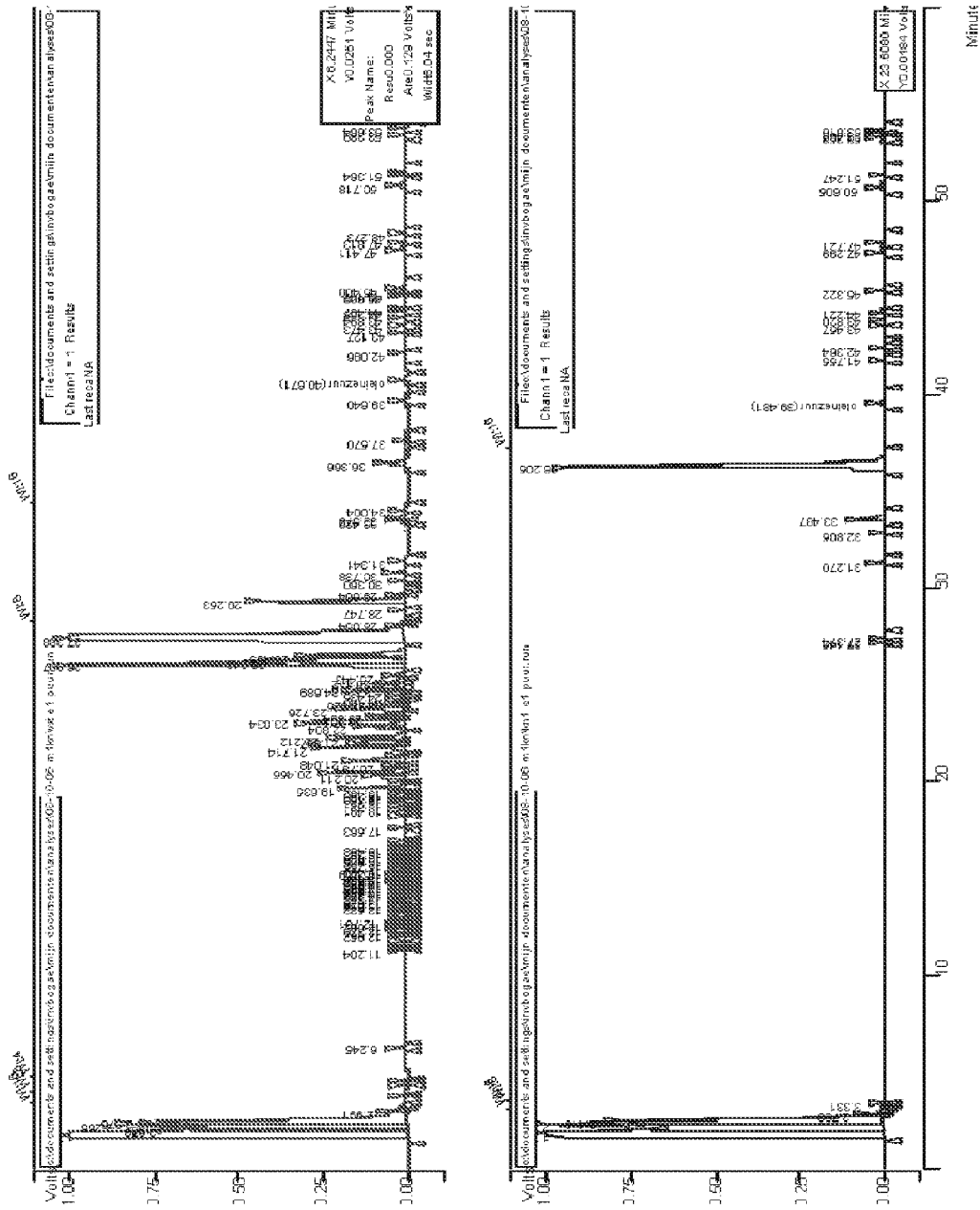
FIG. 1 HPLC-ELSD analysis of the sophorolipid production medium for *Candida bombicola* wild-type (up) and one of the cyp52M1-negative strains (down). Major class sophorolipids are detected between 25 and 30 min. Oleic acid and linoleic acid elute at 33.5 and 36.2 min respectively.

The present invention demonstrates that, surprisingly, sophorolipid-negative strains displayed equal growth characteristics and biomass formation as compared to the wild type and were not inhibited by the presence of oleaginous substrates. The invention further discloses that sophorolipid-negative strains can be used to produce useful compounds. In addition, the present invention also discloses two glucosyltransferase genes with key-functions in sophorolipid production.

Therefore, the invention relates to a modified yeast strain belonging to a yeast species capable of producing sophorolipids characterized in that said yeast strain has, compared to an unmodified wild-type strain: a) at least one mutation in its genome, and b) a reduction in its capability of producing sophorolipids of at least 75%, and wherein said sophorolipids are constituted of the sugar sophorose attached to a $C_{16}$, $C_{18}$, $C_{22}$ or $C_{24}$ hydroxylated fatty acid. The reduction in said capability must be measured by fermentation of said mutant and said wildtype strain under exactly the same fermentation conditions, and similarly, sophorolipid production by said mutant and said wildtype must be measured by exactly the same method. Quantification of said sophorolipid production can—for example—be undertaken after precipitation from the fermentation medium or after extraction with ethylacetate as described by Lang et al. (2000).

The term 'yeast species capable of producing sophorolipids' refers to a phylogenetically diverse group of yeasts (predominantly Ascomycetes and few Basidiomycetes) which spontaneously synthesize sophorolipids constituted of the sugar sophorose attached to a hydroxylated fatty acid. Said phylogenetically diverse group of yeasts comprises the species *Candida apicola* (Gorin et al., 1961) which was initially identified as *C. magnolia*, *C. bombicola* (Spencer et al., 1970), *Wickerhamiella domericqiae* (Chen et al., 2006), *Rhodotorula bogoriensis* (Tulloch et al., 1968), *Pichia anomala* PY1, *Candida batistae* (Konishi et al., 2008), *Candida floricola* (Imura et al., 2010), *Candida riodocensis*, *Candida stellata* and *Candida* sp. NRRL Y-27208 (Kurtzman et al., 2010) and other species of the so-called *Starmerella* clade which encorporates over 40 species. *C. bombicola* has been recently reassigned to the genus *Starmerella* (Rosa & Lachance, 1998).

Therefore, the invention further relates to a modified yeast strain as indicated above wherein said yeast species is selected from the group of sophorolipid producing yeasts, consisting of *Candida bombicola, Candida apicola, Candida batistae, Candida floricola, Candida riodocensis, Candida stellata, Candida* sp. NRRL Y-27208, *Rhodotorula bogoriensis, Pichia anomala* PY1, *Wickerhamiella domericqiae* and sophorolipid-producing species of the *Starmerella* clade. More specifically, the invention relates to a modified yeast strain as indicated above wherein said *Candida bombicola* is the strain *Candida bombicola* ATCC 22214.

The term 'modified yeast strain' indicates that the genetic material of said yeast strain has been altered so that yeast strain is incapable, or is almost incapable of producing sophorolipids. The term 'almost incapable' indicates that said modified yeast strain is solely capable of producing a maximum of 25% of the total production per time unit of sophorolipids by a so called unmodified wild-type strain. Modified yeast strains that are solely capable of producing a maximum of 20%, 15%, 10% or 5% of the total production per time unit of sophorolipids by a so called unmodified wild-type strain are also envisioned by the present invention. Modified yeast strains that are completely incapable (0%) of producing sophorolipids are a preferred embodiment of the present invention. The term 'unmodified wild-type strain' refers to a yeast strain as it occurs in nature and which is fully capable (100%) of producing sophorolipids.

More specifically, the term 'modified yeast strain' refers to a yeast strain containing at least one mutation in its genome. The term mutation refers to a spontaneous mutation and/or to an induced mutation in the genome of said yeast strain. Said mutation can be a point mutation, deletion, insertion or any other type of mutation. The term most specifically refers to knock outs (KO) via insertion of a KO cassette.

Inducing a mutation in the genome of a yeast strain can be undertaken by any method in the art known by a skilled person such as the insertion of a KO cassette into a gene of interest. Similarly, tracing or detecting whether there is a mutation in the genome of a modified gene—compared to a wild type strain—can also be determined by any method known in the art. The term 'sophorolipids' refer to carbohydrate-based, amphiphilic biosurfactants that are constituted of the sugar sophorose attached to a $C_{16}$, $C_{18}$, $C_{22}$ or $C_{24}$ hydroxylated fatty acid, i.e. hydroxylated fatty acids wherein the fatty acid chain is composed of 16, 18, 22 or 24 C-atoms. More specifically the term refers to glycolipid biosurfactants that are constituted of a sophorose head group (2-O-β-D-glucopyranosyl-D-glucopyranose) from which the anomeric C-atom is attached to an (ω) or (ω-1) hydroxylated $C_{16}$, $C_{18}$, fatty acid or to a $C_{22}$ or $C_{24}$ fatty acid hydroxylated at the $C_{13}$ position. With regard to *C. bombicola*—said fatty acid chain is composed of 16 or 18 C-atoms. They occur either as open-ring structures (acid form) or as lactones with an intra-esterification between the fatty acid carboxyl group and the, 4″, 6′ or 6″ carbon atom of the sophorose head group. In addition, acetyl groups can be attached at the 6′ and/or 6″ positions (Asmer et al., 1988). In a typical *Candida bombicola* fermentation with e.g. rapeseed oil as the hydrophobic carbon source, sophorolipids are present as a complex mixture of structurally related molecules with the mono- and di-acetylated lactonic sophorolipids being the most important.

The invention further concerns a modified yeast strain as indicated above, wherein said mutation is a deletion in a gene encoding for a protein, more specifically wherein said protein is an enzyme or a regulatory protein, involved in the sophorolipid biosynthetic pathway. More specifically, the invention relates to mutations in the genes CYP52M1 (Van Bogaert et al., 2009) encoding for a cytochrome P450 monooxygenase, UGTA1 (depicted by SEQ ID No 1) encoding for glucosyltransferase 1 and UGTB1 (depicted by SEQ ID No 3) encoding for glucosyltransferase 2.

Hence, and more specifically the present invention relates to a modified yeast strain as indicated above wherein said gene encodes for a cytochrome P450 monooxygenase or a glucosyltransferase, and more specifically wherein said gene encoding for a cytochrome P450 monooxygenase is the CYP52M1 gene having Genbank accession number EU552419 and wherein said gene encoding for a glucosyltransferase is the UGTA1 gene having a sequence as depicted by SEQ ID No 1 and having Genbank accession number HM440973 or is the UGTB1 gene having a sequence as depicted by SEQ ID No 3 and having Genbank accession number HM440974.

The invention further relates to a nucleic acid sequence as depicted by SEQ ID No 1 encoding for the UDP-glucosyltransferase UgtA1 responsible for the first glucosylation step in the sophorolipid biosynthetic pathway of *Candida bombicola*, or a fragment thereof encoding for a protein retaining said UDP-glucosyltransferase activity, or a variant thereof encoding for a protein having at least 50% sequence identity with SEQ ID No 2 and having said UDP-glucosyltransferase activity. The term 'fragment' refers to a nucleic acid sequence containing fewer nucleotides than the nucleic acid sequence as depicted by SEQ ID No 1 and that encodes for a protein retaining said UDP-glucosyltransferase activity. The term "variant" refers to a nucleic acid encoding for a protein having at least 50% sequence identity, preferably having at least 51-70% sequence identity, more preferably having at least 71-90% sequence identity or most preferably having at least 91, 92, 93, 94, 95, 96, 97, 98 or 99% sequence identity with SEQ ID No 2 or with a fragment thereof, and, that encodes for a protein retaining said UDP-glucosyltransferase activity.

The invention also relates to an amino acid sequence as depicted by SEQ ID No 2 and corresponding to the UDP-glucosyltransferase UgtA1 responsible for the first glucosylation step in the sophorolipid biosynthetic pathway of *Candida bombicola*, or a fragment thereof having said UDP-glucosyltransferase activity or a variant thereof having at least 50% sequence identity with SEQ ID No 2 and having said UDP-glucosyltransferase activity. The term 'fragment' refers to a protein containing fewer amino acids than the amino acid sequence as depicted by SEQ ID No 2 and that retains said UDP-glucosyltransferase activity. Such fragment can for example omit N- and C-termini of the protein leaving a shortened protein of 366 amino acids starting at 110 and ending at A375 without hereby touching the UDP-glucosyltransferase activity. The term "variant" refers to a protein having at least 50% sequence identity, preferably having at least 51-70% sequence identity, more preferably having at least 71-90% sequence identity or most preferably having at least 91, 92, 93, 94, 95, 96, 97, 98 or 99% sequence identity with SEQ ID No 2 or with a fragment thereof, and, that encodes for a protein retaining said UDP-glucosyltransferase activity. The latter may differ from the protein as depicted by SEQ ID No 2 or a fragment thereof only in conservative substitutions and/or modifications, such that the ability of the protein to have UDP-glucosyltransferase activity is retained. A "conservative substitution" is one in which an amino acid is substituted for another amino acid that has similar properties, such that one skilled in the art of protein chemistry would expect the nature of the protein to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be proteins as described herein modified by, for example, by the deletion or addition of amino acids that have minimal influence on the UDP-glucosyltransferase activity, secondary structure and hydropathic nature of the protein. Regions within SEQ ID No 2 which contribute to the proteins' activity are regions determined by the residues I10 to V50, G131 to L155, M180 to H196, W213 to F233, S266 to Y282, V341 to H355, A375 to T386. Hence, the variants as defined above preferably comprise at least one of the latter regions. More preferably, the latter variants comprise at least one of the following residues or amino acids of SEQ ID No 2: G19, H20, M22, N181, L184, E185, F189, S216, T277, N343, G345, G347, G348 or H351.

The invention further relates to a nucleic acid sequence as depicted by SEQ ID No 3 encoding for the UDP-glucosyltransferase UgtB1 responsible for the second glucosylation step in the sophorolipid biosynthetic pathway of *Candida bombicola*, or a fragment thereof encoding for a protein retaining said UDP-glucosyltransferase activity, or a variant thereof encoding for a protein having at least 50% sequence identity with SEQ ID No 4 and having said UDP-glucosyltransferase activity. The term 'fragment' refers to a nucleic acid sequence containing fewer nucleotides than the nucleic acid sequence as depicted by SEQ ID No 3 and that encodes for a protein retaining said UDP-glucosyltransferase activity. The term "variant" refers to a nucleic acid encoding for a protein having at least 50% sequence identity, preferably having at least 51-70% sequence identity, more preferably having at least 71-90% sequence identity or most preferably having at least 91, 92, 93, 94, 95, 96, 97, 98 or 99% sequence identity with SEQ ID No 4 or with a fragment thereof, and, that encodes for a protein retaining said UDP-glucosyltransferase activity.

The invention also relates to an amino acid sequence as depicted by SEQ ID No 4 and corresponding to the UDP-glucosyltransferase UgtB1 responsible for the second glucosylation step in the sophorolipid biosynthetic pathway of *Candida bombicola*, or a fragment thereof having said UDP-glucosyltransferase activity or a variant thereof having at least 50% sequence identity with SEQ ID No 4 and having said UDP-glucosyltransferase activity. The term 'fragment' refers to a protein containing fewer amino acids than the amino acid sequence as depicted by SEQ ID No 4 and that retains said UDP-glucosyltransferase activity. Such fragment can for example omit N- and C-termini of the protein leaving a shortened protein of 351 amino acids starting at 18 and ending at G358 without hereby touching the UDP-glucosyltransferase activity. The term "variant" refers to a protein having at least 50% sequence identity, preferably having at least 51-70% sequence identity, more preferably having at least 71-90% sequence identity or most preferably having at least 91, 92, 93, 94, 95, 96, 97, 98 or 99% sequence identity with SEQ ID No 4 or with a fragment thereof, and, that encodes for a protein retaining said UDP-glucosyltransferase activity. The latter may differ from the protein as depicted by SEQ ID No 4 or a fragment thereof only in conservative substitutions and/or modifications, such that the ability of the protein to have UDP-glucosyltransferase activity is retained. A "conservative substitution" is one in which an amino acid is substituted for another amino acid that has similar properties, such that one skilled in the art of protein chemistry would expect the nature of the protein to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be proteins as described herein modified by, for example, by the deletion or addition of amino acids that have minimal influence on the UDP-glucosyltransferase activity, secondary structure and hydropathic nature of the protein. Regions within SEQ ID No 4 which contribute to the proteins' activity are residues 18 to V48, G129 to C153, I170 to E186, L203 to F223, S261 to Y277, V334 to H350 and A371 to T382. Hence, the variants as defined above preferably comprise at least one of the latter regions. More preferably, the latter variants comprise at least one of the following residues or amino acids of SEQ ID No 4: G17, H18, G20, R175, V178, F179, G182, R212, T272, N338, G340, G342, G343 or H346.

The present invention further relates to the expression of SEQ ID No 1, SEQ ID No 2, SEQ ID No 3 and SEQ ID No 4 or variants thereof in other organisms than the various yeast species capable of producing sophorolipids as specified above. These 'other' organisms can be micro-organisms such as bacteria, yeast and fungi, plants, animals and algae. Expression of the genes in these organisms leads to the production of useful compounds such as glycosylated compounds, glycolipids or sophorolipids.

As specified above, the present invention specifically refers to the use of SEQ ID No 1, SEQ ID No 2, SEQ ID No 3 and SEQ ID No 4 and variants thereof in yeast species capable of producing sophorolipids. These sequences can either be manipulated in the endogenous strain (e.g. in *C. bombicola*) by knocking out the gene or can be subjected to other alterations such as mutation or overexpression. These manipulations can be obtained by various methods known by the person skilled in the art. Alteration of the expression will result in modification of a glycolipid biosynthetic pathway, more in particular the sophorolipid biosynthetic pathway. The invention has further relates to the usage of a modified yeast strain as indicated above for the production of compounds such as recombinant proteins (e.g. GFP and amylase), beta-hydroxy fatty acids and polyhydroxyalkanoates (PHA), dicarboxylic acids, polyunsaturated fatty acids, hydroxylated fatty acids: terminal or subterminal hydroxylated or at any other position, glycolipids such as cellobioselipids, glucolipids, trehalose-lipids rhamnolipids, sophorolipids with a special fatty acid tail, sophorolipids with a fatty acid tail ranging from 10 to 15 carbon atoms, sophorolipids with a fatty acid tail of 17 carbon atoms, sophorolipids with a fatty acid tail ranging from 19 till 25 carbon atoms, sophorolipids with branched fatty acid tail, sophorolipids with multiple hydroxylated fatty acid tail, fully lactonized sophorolipids and fully acidic sophorolipids; rhamnose, sophorose, polyketide antibiotics, lactonic structures (fatty acid based), organic acids such as succinate, adipate and citrate; oleagenious compounds, hydrophobic compounds, sophorose, rhamnose, squaleen, vitamin D, resveratrol, steroids, and carotenoides.

The invention further specifically relates to the usage as indicated above wherein said compounds are glycolipids (such as cellobioselipids and glucolipids), polyhydroxyalkanoates or any other oleaginous compounds and recombinant proteins such as green fluorescent protein and amylase.

The above-indicated usages can be performed using well known techniques of genetic engineering.

The present invention and the above-indicated usages will be illustrated by the following non-limiting examples.

EXAMPLES

Example 1

Cytochrome P450 Monooxygenase CYP52M1 Knock-Out

Introduction

This strain is knocked-out at the CYP52M1 gene (GenBank accession number EU552419), encoding for the enzyme responsible for the hydroxylation of fatty acids with a preferred length of 16 or 18 carbon atoms. The fatty acid is converted to a ω or ω-1 hydroxylated fatty acid. In this strain, hardly any sophorolipid production is detected, while cell growth and viability is comparable to the wild type.

Materials and Methods

Strains, Plasmids and Culture Conditions

*Candida bombicola* ATCC 22214 was used in all experiments. When sophorolipid production was intended, the medium described by Lang et al. (Lang et al., 2000) was used. Yeast cultures were incubated at 30° C. and 200 rpm.

All PCR products intended for sequence analysis were cloned into the pGEM-T® vector (Promega). *Escherichia coli* DH5α was used in all cloning experiments and was transformed as described by Sambrook and Russell (2001). *E. coli* cells were grown in Luria-Bertani (LB) medium (1% trypton, 0.5% yeast extract and 0.5% sodium chloride) supplemented with 100 mg/L ampicillin and 40 mg/L X-gal if necessary. Liquid *E. coli* cultures were incubated at 37° C. and 200 rpm.

DNA Isolation and Sequencing

Yeast genomic DNA was isolated with the GenElute™ Bacterial Genomic DNA Kit (Sigma). Preceding protoplast formation was performed by incubation at 30° C. for 90 minutes with zymolyase (Sigma).

Bacterial plasmid DNA was isolated with the QIAprep Spin Miniprep Kit (Qiagen). All DNA sequences were determined at the VIB Genetic Service Facility (Belgium).

Transformation

*C. bombicola* cells were transformed with the lithium acetate method (Gietz et al., 1995), but 50 mM LiAc was used instead of 100. Transformants were selected on yeast peptone dextrose (YPD) plates (1% yeast extract, 2% peptone, 2% glucose and 2% agar) containing 500 μg/mL hygromycin or on synthetic dextrose (SD) plates [0.67% yeast nitrogen base without amino acids (DIFCO) and 2% glucose]. *E. coli* cells were transformed as described by Sambrook (Sambrook et al., 2001).

Creation of the Knock-Out Cassette

The 1617 bp coding fragment and 218 and 1060 bp upstream and downstream of the CYP52M1 gene were amplified with the primers A21TotFor and A21TotRev (Table 1), yielding a fragment of 2869 bp which was cloned into the pGEM-T® vector (Promega). The created vector was digested with AvaI, cutting the coding sequence of CYP52M1 twice, in this way deleting 308 bp of the CYP52M1 sequence. The *E. coli* hygromycin resistance gene controlled by the *Candida bombicola* GPD promoter (Van Bogaert et al., 2008a) was inserted by means of the In-Fusion™ 2.0 Dry-Down PCR Cloning Kit (Clontech). The primers GHInfA21 For and HygroInfA21Rev were designed according to the guidelines of the manual and used for integration of the hygromycin resistance cassette (1968 bp) into CYP52M1. The primerpair A21KnockHygroCasFor and A21KnockHygroCasRev were used for the amplification of a 4003 bp fragment containing the hygromycin resistance cassette with approximately 1000 bp of the CYP52M1 sequence on each site. The fragments were used to transform the *Candida bombicola* wild type strain.

Sampling

Analytical sophorolipid samples were prepared as follows: 440 μL ethylacetate and 11 μL acetic acid were added to 1 mL culture broth and shaken vigorously for 5 min. After centrifugation at 9 000 g for 5 min, the upper solvent layer was removed and put into a fresh eppendorf tube with 600 μL ethanol. At the end of the incubation period, 3 volumes ethanol were added to the culture broth for total extraction of sophorolipids. Cell debris was removed by centrifugation at 1500 g during 10 min. Samples were analysed by HPLC and Evaporative Light Scattering Detection.

Cell dry weight (CDW) was measured by centrifugation of 2 mL culture broth for 5 min at 9 000 g. Pellets were washed two times with ethanol to remove sophorolipids and hydrophobic substrate and finally dissolved in distilled water. The suspension was transferred to a cellulose nitrate filter with a pore diameter of 0.45 μm (Sartorius) and the dry weight was determined in the XM60 automatic oven from Precisa Instruments Ltd.

Colony forming units (CFU) were determined by plating decimal dilutions on agar plates with 10% glucose, 1% yeast extract and 0.1% urea which were incubated at 30° C. for three days.

HPLC-Analysis of Sophorolipids

Sophorolipid samples were analysed by HPLC on a Varian Prostar HPLC system using a Chromolith® Performance RP-18e 100-4.6 mm column from Merck KGaA at 30° C. and Evaporative Light Scattering Detection (Alltech). A gradient of two eluents, a 0.5% acetic acid aqueous solution and acetonitrile, had to be used to separate the components. The gradient started at 5% acetonitrile and linearly increased till 95% in 40 min. The mixture was kept this way for 10 min and was then brought back to 5% acetonitrile in 5 min. A flow rate of 1 mL/min was applied.

Results and Discussion

The CYP52M1 knock-out cassette was constructed as described in the Materials and Methods section. This linear fragment was used to transform *Candida bombicola* wild type cells. The genotype of 10 transformants was checked by yeast colony PCR with the primer HygroInsertCheckFor, binding on the knock-out cassette and primer A21totRev, binding the genomic CYP52M1 gene (Table 1). All 10 transfromants displayed the right genotype. The effect of the disrupted CYP52M1 gene was tested by evaluating three randomly selected transformants for their production of sophorolipids in liquid medium. CDW and colony forming unit were similar as compared to the wild type strain, indicating that the gene disruption did not affected cell-growth.

However, clear differences were observed regarding glucose consumption. Whereas during the exponentional growth phase no differences were observed, the wild type shows much faster consumption in the stationary growth phase, when sophorolipid synthesis takes place. As sophorolipid production demands a large glucose input, low glucose utilization of the knock-outs suggests the absence of sophorolipid synthesis. Furthermore, during the whole incubation period rapeseed oil staid floating on the culture medium surface of the knock-outs, indicating that also the hydrophobic carbon source required for sophorolipid production is not consumed.

Finally, biosurfactant production was checked by HPLC analysis of samples taken during and at the end of the incubation period. Whereas there was a clear production for the wild type, no sophorolipids could be detected in the medium or the cells of all tree knock-outs (FIG. 1). The peaks observed for the transformant are degradation products of the not consumed rapeseed oil: oleic acid, the major constituent of rapeseed oil fatty acids (60%) is detected at 36.2 minutes and also linoleic acid (23%) is identified (33.5 min).

The above mentioned results demonstrate that CYP52M1 is the cytochrome P450 monooxygenase responsible for the synthesis of hydroxylated fatty acids, which are essential for sophorolipid production. Disabling of the gene inhibits sophorolipid synthesis, but has surprisingly no effect on cell growth or viability. The created strains are unable to produce sophorolipids and can consequently be used as production host. As *C. bombicola* is not intoxicated by oily or hydrophobic substrates and has metabolic pathways to metabolise or convert those, the knock-out strain can be used as a platform strain for the synthesis of other oleaginous products such as polyhydroxyalkanotes. Furthermore, the strains can be used to express heterologous P450 enzymes in order to create sophorolipids with a tailor-made fatty acid tail.

Example 2

Identification of the UDP-Glucosyltransferase Gene UGTA1, Responsible for the First Glucosylation Step in the Sophorolipid Biosynthetic Pathway of *Candida Bombicola* ATCC 22214

Introduction

This strain is knocked-out at the UGTA1 gene (GenBank accession number HM440973), encoding for the enzyme responsible for the first glucosylation step in the sophorolipid biosynthetic pathway. This enzyme transfers glucose from UDP-glucose to a hydroxylated fatty acid resulting in the production of a glucolipid.

In this strain, no sophorolipid production is detected, while cell growth and viability is comparable to the wild type (FIG. 2).

Materials and Methods

Strains, Plasmids and Culture Media

*Candida bombicola* ATCC 22214 was used for isolation of the UGTA1 gene and *C. bombicola* G9 (Van Bogaert et al., 2008b) for creation of the ugtA1 deletion mutant. *Escherichia coli* DH5α F' was used for plasmid maintenance. Yeast cells were grown on YPD medium containing 1% yeast extract, 2% peptone and 2% dextrose, SD medium containing 0.67% yeast nitrogen base without amino acids (Difco) and 2% glucose or 3C medium containing 10% glucose, 1% yeast extract and 0.1% ureum. Liquid media were incubated at 30° C. and 200 rpm. *E. coli* was grown on Luria Bertani medium (0.5% Bacto yeast extract, 1% Bacto Trypton, 0.5% NaCl) containing 0.01% ampicillin and incubated at 37° C. and 200 rpm. Plasmids were isolated from *E. coli* DH5α F' by means of the MiniPrep Plasmid Isolation kit from Qiagen.

Cloning of the *C. Bombicola* UGTA1 Gene

Primer Design and Sequence Analysis

Primer design, sequence analysis and strategy design were performed with the Clone Manager Professional Suite software (Version 8.0). Primers were ordered at Sigma and all plasmids created were sent for sequencing either to VIB (Belgium) or AGOWA (Germany). Homology searches were performed with the BLAST program (Altschul et al., 1997) against databases available at the NCBI website.

Isolation of Genomic DNA

*C. bombicola* ATCC22214 was grown overnight on 3C medium. Minor amounts of sophorolipids were removed by extracting 500 µl culture samples with one volume ethylacetate. Yeast cell wall was removed enzymatically by incubating with 200 units Yeast Lytic Enzyme (Sigma) in SCE buffer (1M sorbitol, 0.1M sodium acetate and 60 mM EDTA, pH 7.0) for 90 min at 37° C. in presence of 3.75 µl mercaptoethanol. Genomic DNA was isolated from the remaining protoplasts by means of the GenElute™ Bacterial Genomic DNA kit (Sigma).

Genome Walking

For isolation of the UGTA1 gene sequence from *C. bombicola* ATCC 22214 genomic DNA, the BD GenomeWalker™ Universal Kit (BD Biosciences) was used. Gene specific primers for primary and nested PCR were designed based on the partial UGTA1 sequence obtained from preliminary genome sequencing data and are given in Table 2. Amplification reactions were performed with the Expand Long Template PCR System (Roche) following the protocol as described in (De Maeseneire et al., 2006). PCR amplification products are purified either from the PCR mix or by gel extraction making use of the Qiaquick PCR purification kit (Qiagen) or Qiaexll gel extraction kit (Qiagen) respectively. Purified fragments were cloned in pGEM-T® using pGEM-T® Vector System (Promega) and resulting plasmids used for transformation of *E. coli* DH5α F' according to Sambrook (Sambrook et al., 2001). Correct colonies were grown in liquid LB for subsequent plasmid isolation and sequencing.

Cloning of the Complete UGTA1 Gene

The complete sequence of the UGTA1 gene was amplified from *C. bombicola* ATCC 22214 genomic DNA by means of the High Fidelity PCR Master Kit (Roche). The obtained 2566 bp fragment was purified and cloned in pGEM-T® as described before. The resulting plasmid was called pGugtA1Tot.

Creation of the UGTA1 Knock-Out Cassette

The procedure leading to the knock-out cassette for the *C. bombicola* UGTA1 gene is based on a restriction enzyme mediated insertion of the URA3 selectable marker (Van Bogaert et al., 2007) between regions of homology to the 5' and 3' ends of the UGTA1 gene. All PCR reactions were performed with the Roche High Fidelity System. In a first step, the 5' (A1P) and 3' (A1T) regions of the UGTA1 gene were amplified from plasmid pGugtA1Tot by means of restriction primers A1P RevNheI and A1T ForNheI in combination with UDPGTA1 TotF and A1T Rev to amplify UGTA1 5' (A1P) and UGTA1 3' (A1T) regions respectively (Table 2). These fragments of 853 bp and 1121 bp respectively were purified and digested with NheI restriction enzyme (New England Biosystems) according to Sambrook (Sambrook et al., 2001). The digested fragments were purified from the restriction mixes and ligated by means of the T4 DNA ligase (Fermentas). The ligation product was amplified again and purified by gel extraction. Subsequently this fragment (A1PT) was cloned in pGEM-T®, plasmid pGA1PT was obtained from *E. coli* and checked by sequencing as described earlier. Since pGEM-T® lacks a NheI restriction site, the obtained plasmid pGA1PT can be linearised solely at the introduced NheI site between A1P and A1T fragments, giving rise to sticky ends at both sites. Accordingly, the URA3 marker is amplified from plasmid pCbura3 (Van Bogaert et al., 2007) making use of restriction primers Ura3 FbisNheI and Ura3 RbisNheI that both contain NheI restriction site extensions at their 5'ends. After purification, the obtained fragment was digested with NheI and ligated into the linearised pGA1 PT vector by means of the T4 DNA ligase (Fermentas). The ligation mixture was used for transformation of *E. coli* DH5α and right transformants were grown in LB for subsequent plasmid isolation. The integration of the URA3 marker was verified by control digestion with restriction enzyme AccI (New England Biolabs). The complete URA3 gene sequence on the obtained plasmid pGKO_A1 was confirmed by sequencing.

Creation of a ugtA1 Deletion Mutant

A linear knock-out cassette was produced from plasmid pGKO_A1 by high fidelity PCR making use of the outer primers UDPGTA1 TotF and A1T Rev since it has been shown that linearisation increases to a large extent the recombination frequency (Van Bogaert et al., 2008b). The obtained fragment was purified and 2.5 μg was used for transformation of the ura3⁻ *C. bombicola* G9. The protocol as described for *Saccharomyces* was used (Gietz et al., 1995) with some slight modifications. A 50 mM LiAc solution was used instead of 100 mM, incubation of cells with the cassette before heat shocking occurred for 90 minutes instead of 30 and no DMSO was added. After transformation, cells were plated on SD agar medium and incubated at 30° C. until transformant colonies appeared.

Characterisation of the ugtA1 Deletion Mutant

Correct integration of the cassette into the genome was checked by means of yeast colony PCR using primers that anneal outside the recombination sites. Transformants with the right genotype were then transferred to 3C agar plates and tested for sophorolipid production. For that, the mutant yeast colony was inoculated in liquid medium as described by Lang (Lang et al., 2000) and grown for 48 hours before addition of rapeseed oil (30 g/L). Wildtype *Candida bombicola* ATCC 22214 was grown the same way and served as a reference. Ten days after addition of the hydrophobic carbon source, sophorolipid production was verified by extracting 1 ml culture medium with 400 μl technical ethylacetate in presence of 10 μl acetic acid. After vortexing for 5 minutes, 300 μl of the solvent phase was diluted in 1.7 ml absolute ethanol and analysed on HPLC-ELSD using a Varian ProStar HPLC (Varian) equipped with a Chromolith® Performance RP-18e column [100 mm (I)×4.6 mm (I.D.)] (Merck) and connected to an Evaporative Light Scattering Detector (Alltech). Compounds were eluted by means of an acetonitrile/acetic acid (0.5% in water) gradient (5/95 to 95/5 in 40 min) under constant flow of 1 ml/min. Column temperature was set at 30° C.

Biocatalytic Function of the UgtA1 Glucosyltransferase

Preparation of Cell Lysates

Wildtype yeast and the ugtA1 deletion mutant A113 were inoculated from 3C agar medium into 5 ml Lang medium and grown overnight at 30° C. and 200 rpm. With this preculture, 50 ml of fresh Lang medium was inoculated with a start OD of 0.2 and incubated the same way until cells were lysed. Cells were harvested by centrifugation at 3000 rpm and 4° C. with a swinging bucket centrifuge and washed with 10 ml distilled water. The pellet was then resuspended in lysis buffer pH 7.7 containing 50 mM $KH_2PO_4$, 5% glycerol, 0.5 mM $MgCl_2$, 0.5 mM DTT and 1 mM PMSF to $OD_{100}$. An equal volume of acid washed glass beads (150-212 μm diameter, Sigma) was added and cells were disrupted by vortexing during 15 minutes with 30 seconds intervals on ice. Soluble protein fractions were used for enzyme assays after centrifugation of the crude lysate at 3000 rpm at 4° C. Protein concentration in the lysate was determined by means of the BCA™ Protein Assay Kit (Pierce). Protein solutions were stored at 4° C.

Enzyme Assays

UDP-glucose was obtained from Sigma, 17-hydroxyl-octadecenoic acid and glucolipid were obtained from sophorolipids as described before (Saerens et al., 2009). All substrate solutions were prepared freshly in 50 mM $KH_2PO_4$, pH 7.7. Enzyme assays contained 2 mM UDP-glucose, 2 mM acceptor and 200 μl fresh protein solution in a total volume of 250 μl. For the blank reactions phosphate buffer replaced either the donor, the acceptor or the protein solution. For each assay also a blank reaction with 200 μl buffer was performed. All enzyme reactions were incubated at 30° C. for 3 hours. Reactions were stopped by addition of 200 μl HCl (2N) and glycolipids were extracted with 800 μl diethylether/ethylacetate (1/1). From the solvent phase, 700 μl was recovered, evaporated to dryness and redissolved in 300 μl absolute ethanol before analysis on HPLC as described above.

Results and Discussion

Isolation of the UGTA1 Gene Sequence

Preliminary genome sequencing data yielded part of a putative glucosyltransferase with homology to glycosyltransferases of the MGT family and other UDP-glucuronosyl/UDP-glucosyltransferases available at the NCBI databases. The alignments illustrated that this partial ORF contained an appropriate start codon but lacked a stop codon. In order to isolate the complete ORF, primers were designed for further genome walking downstream of this putative gene. In this way, another 1600 bp could be obtained that after assembling with the primary sequence resulted in a total raw sequence fragment of 2566 bp. This fragment contained a complete open reading frame of 1392 bp encoding a putative UDP-glucuronosyl/UDP-glucosyltransferase gene of 463 amino acids which we named UgtA1.

Cloning and Sequence Analysis of the Complete UGTA1 Gene

To isolate the complete UGTA1 gene from the *Candida bombicola* genome, the 2566 bp fragment was amplified by high fidelity PCR on freshly isolated genomic DNA. The encoding region with 233 bp and 153 bp of the up- and downstream regions respectively is given in FIG. 3. The open reading frame encodes a putative glycosyltransferase of 463 amino acids with an estimated molecular mass of 50.5 kDa and estimated pI of 5.45.

Though most yeast promoters lack a clear TATA box, an NT rich TATA-like consensus sequence TATA(A/T)A(A/T)(A/G) could be identified 50-200 bp upstream of highly regulated or stress-induced genes from *Saccharomyces* (Basehoar et al., 2004). If comparable regulatory mechanisms would exist for the transcriptional activation of housekeeping and stress-induced genes in *C. bombicola*, and since sophorolipid production is linked to nitrogen limiting conditions (Davila et al., 1992) one might expect a comparable TATA-like consensus in genes involved in sophorolipid production by this yeast. One possible promoter element with high homology to the *Saccharomyces consensus* could be identified 415 bp upstream of the UGTA1 startcodon (results not shown), while a second A/T rich region is found closer to the startcodon (FIG. 3). Also several possible polyadenylation sequences are found but no specific signal elements involved in 3'-end formation of mRNA like described for yeast (Guo et al., 1996) can be distinguished.

Another typical feature for genes regulated by nitrogen metabolism is the presence of GATA-like regulatory sequences in their upstream regions. Such GATA motifs are recognized by GATA-type transcription factors which are strongly activated by depletion of nitrogen (Magasanik et al., 2002). One typical example of such GATA-type transcription factor is the AreA gene of *Aspergillus nidulans* (Marzluf et al., 1997) and several GATA-like elements are recognized in glycolipid synthesizing genes of *Ustilago maydis* [Hewald et al., 2005]. In the 5' upstream region of the UGTA1 encoding region several possible GATA-like elements are found.

Sequence Homology to Other UDP-Glucosyltransferases

Analysis of the UgtA1 protein sequence via the Conserved Domain Database available at the NCBI website (Marchler-Bauer et al., 2009), shows that this protein belongs to the GT1 family of glycosyltransferases (E.C. 2.4.1), a polyspecific family that harbours to date over 3200 different glycosyltransferases of which most are inverting enzymes using nucleotide-activated sugars or sugar phosphates as donor molecules (Campbell et al., 1997, Coutinho et al., 2003). The structures of the GT1 proteins show the typical GT-B type topology, which is reflected in a conserved domain (cl 10013) that is also found in the UgtA1 sequence and therefore this family is taken up in the GT-B type superfamily of glycosyltransferases (Teichmann et al., 2007). Other glycosyltransferases such as the RhlB from *P. aeruginosa* (Ochsner et al., 1994a) and both the Emt1 and Hgt1/Ugt1 proteins from *U. maydis* (Hewald et al., 2005, Teichmann et al., 2007), which catalyze analogous glycosylation reactions in the glycolipid biosynthetic pathways of these organisms, belong to the same GT1 family. Surprisingly, the overall UgtA1 protein sequence shows only low similarity to these proteins (34% similarity to the *Ustilago* Hgt1/Ugt1 and 38% similarity to the *P. aeruginosa* RhlB) as derived from a global pairwise alignment using BioEdit Software (Hall, 1999). Moreover, a Blastp homology search illustrates that the UgtA1 protein shows poor similarity to any other protein sequence. The highest homology is found with bacterial UDP-glucose/UDP-glucuronosyltransferases of which most belong to the MGT subfamily (Table 3), though the sequence identity is still low. Proteins of the MGT subfamily are involved in biosynthesis or inactivation of macrolide antibiotics and show a conserved domain (TIGR01426/cd 03784) which is also found in the UgtA1 sequence, indicating the transfer of a sugar moiety from a nucleotide activated sugar residue to a complex acceptor such as the heptapeptide core of an antibiotic. These findings indicate that the UgtA1 protein is very likely involved in the synthesis of a complex metabolite.

Creation and Characterization of a ugtA1 Deletion Mutant

The knock-out cassette used is a linear fragment based on a restriction enzyme mediated insertion of the URA3 selectable marker between 853 bp and 1024 bp of homology to the 5' and 3' regions of the UGTA1 gene respectively. This cassette is used for transformation of the ura3 deficient strain G9. Only when homologous recombination has occurred and the cassette is integrated in the genome, URA3 functionality will be recovered and transformants will be able to grow on SD medium, lacking uracil. Five days after transformation of the G9 strain, 40 colonies were obtained on the selective plates, of which 17 were subjected to a yeast colony PCR to check their genotype. Only one colony showed the right genotype and is referred to as *C. bombicola* A113. For the other 16 selected transformants, ura3 complementation will have occurred either by recombination between the marker only and the ura3 mutant allele of the G9 strain or by one sided or illegitimate recombination.

Figure 4:
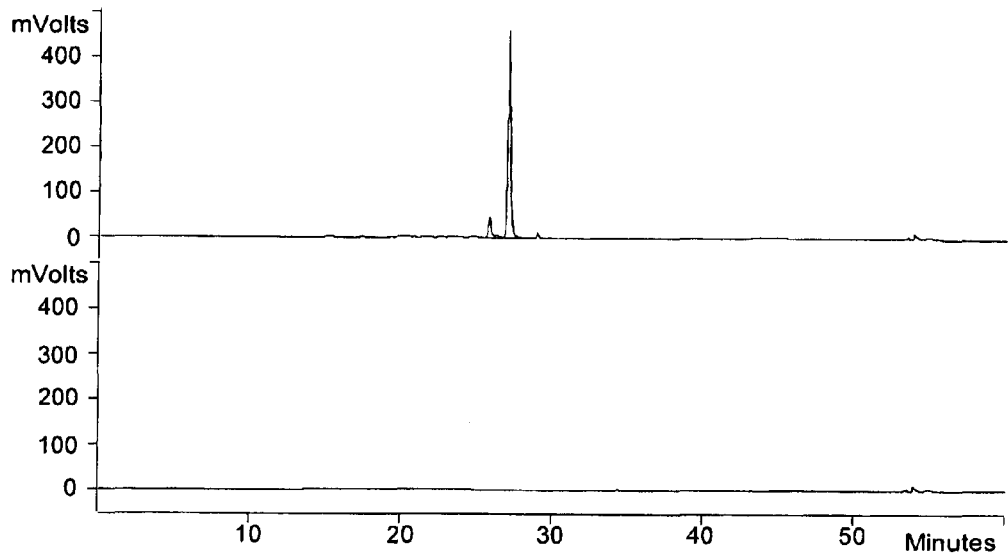
FIG. 4 HPLC-ELSD chromatograms from culture extracts, 10 days after incubation of *C. bombicola* ATCC22214 (up) and *C. bombicola* A113 (down) with rapeseed oil. De novo sophorolipids typically elute between 25 and 30 min.

To control the involvement of the UgtA1 glucosyltransferase in sophorolipid production, the obtained mutant *C. bombicola* A113 was grown in production medium as described before and sophorolipid production was compared to the wildtype yeast. FIG. 4 shows the HPLC chromatograms of culture extracts from both *C. bombicola* A113 and wild type yeast when rapeseed oil was used as hydrophobic carbon source. Only the wild type yeast strain produces sophorolipids while the ugtA1 deletion mutant grew well but completely lost its ability to produce any glycolipid. This clearly indicates that the UgtA1 glucosyltransferase has a key-function in sophorolipid production by the yeast. Since the mutant shows a comparable growth as the wildtype yeast, it is unlikely that the UgtA1 glucosyltransferase has any other function in primary metabolism.

Biocatalytic Function of the UgtA1 Glucosyltransferase

Figure 5:
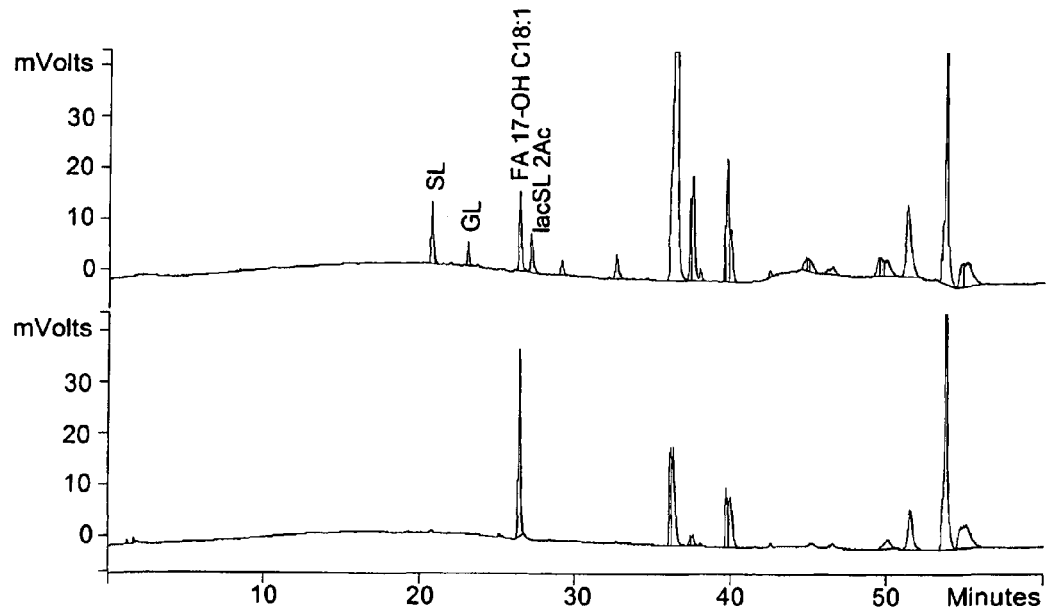
FIG. 5 HPLC-ELSD chromatogram of sample extracts from a glucosyltransferase I assay on soluble protein fractions from wildtype yeast (up) and A113 mutant (down). Peaks at 27 min and 29 min originate from de novo sophorolipid synthesis while peaks eluting after 30 minutes originate from co-extracted apolar cell constituents. FA 17-OH C18:1=17-hydroxyoctadecenoic acid, GL=glucolipid (17-O-(β-D-glucopyranosyl)-octadecenoic acid), SL=diacetylated sophorolipid acid (17-O-(2-O-β-D-glucopyranosyl-glucopyranose)-octadecenoic acid), lacSL 2Ac=diacetylated sophorolipid lactone FIG. 6 HPLC-ELSD chromatogram of sample extracts from a glucosyltransferase II assay on soluble protein fractions from wildtype yeast (up) and A113 mutant (down). Peaks at 27 min and 29 min originate from de novo sophorolipid synthesis while peaks eluting after 30 min originate from co-extracted apolar cell constituents. FA 17-OH C18:1=17-hydroxyoctadecenoic acid, GL=glucolipid (17-O-(β-D-glucopyranosyl)-octadecenoic acid), SL=diacetylated sophorolipid acid (17-O-(2-O-β-D-glucopyranosyl-glucopyranose)-octadecenoic acid), lacSL 2Ac=diacetylated sophorolipid lactone FIG. 7 Complete DNA sequence of the UGTB1 gene (GenBank accession number HM440974, SEQ ID N0° 3). Primer sites are underlined. Putative promoter and terminator elements are indicated by boxes while possible GATA-like regulatory motifs are shaded in grey. The encoded amino acid sequence (SEQ ID N0° 4) of the UgtB1 glucosyltransferase protein is also depicted.

In order to link the UgtA1 glucosyltransferase to a specific step in the sophorolipid biosynthetic pathway, glucosyltransferase activities were measured in cell lysates of the A113 mutant and compared to that of the wildtype yeast. Since sophorolipid production is linked to nitrogen starvation conditions, it is very likely that the expression of genes involved in the biosynthetic pathway only start in early stationary phase. To determine the best time point to harvest cells for protein extraction and subsequent activity tests, wildtype *C. bombicola* was grown in Lang medium and glucosyltransferase activities were determined in 5 ml culture samples taken at different time points. For detection of the first glucosyltransferase activity (GTI), UDP-glucose and 17-hydroxyoctadecenoic acid were used as glucosyl donor and acceptor respectively. For detection of the second activity (GTII), the fatty acid was replaced by the glucolipid. In the wildtype yeast both glucosyltransferase activities were detected from late exponential phase and further increase to a maximum in early stationary phase. Addition of rapeseed oil to the culture medium after 48 hours did not result in increased activities while no significant activity could be detected when cells were grown in standard yeast media such as YPD (results not shown). Therefore the best set up for the enzyme assays is to harvest cells after 42 to 48 hours of incubation in Lang medium without addition of hydrophobic carbon source. Under these conditions, lysates were prepared from both wildtype yeast and the A113 mutant and soluble protein fractions were used for the same glucosyltransferase assays. The results are presented in FIGS. 5 and 6. From FIG. 5 it is clear that both GTI and GTII activities are present in the cell lysate from the wildtype yeast, since both glucolipids (GTI activity) and sophorolipids (GTII activity) are detected as products. None of these activities were observed when either cell lysate, UDP-glucose or fatty acid was omitted from the reaction. In contrast to the wildtype lysate, the cell lysate of the A113 mutant does not show any glucosylation product from the fatty acid what indicates that the UgtA1 protein is at least responsible for the first glucosylation reaction in the sophorolipid biosynthetic pathway. The signals at 27 and 29 minutes in the chromatograms of the wildtype assays, come from de novo synthesis of sophorolipids during growth in Lang medium. These peaks are absent in the chromatograms of the A113 mutant, confirming that de novo synthesis in this mutant is completely blocked. In order to verify if the second glucosylation step (GTII) is affected by the disruption of the UgtA1 protein, the assay was repeated with glucolipid as the acceptor. From FIG. 6 it can be clearly seen that the second glucosylation activity is still present in the A113 lysate and that this activity is comparable to that of the wildtype lysate. We thus provide evidence that sophorolipid production in *C. bombicola* involves two different glucosyltransferases that transfer glucose from UDP-glucose to their respective acceptor substrates in a stepwise but independent manner. We show that the UgtA1 glucosyltransferase isolated here, is responsible for the first glucosylation reaction and disrupting the gene has no influence on the second glucosylation step. This second glucosyltransferase appears to be highly specific towards its own acceptor substrate, since no glucolipid formation is observed when fatty acids are present as acceptor in the A113 assays (FIG. 5). Based on these findings, we believe that sophorolipid production in *C. bogoriensis* relies on a comparable stepwise pathway and that it is doubtful that a multifunctional protein would exist accepting both fatty acid and glucolipid in its catalytic centre.

Conclusion

Here we identified the gene UGTA1 with a clear function in sophorolipid production by *Candida bombicola*. The UGTA1 gene encodes a glucosyltransferase of 463 amino acids and an estimated molecular weight of 50.5 kDa. The protein can be classified within the GT1 family of glycosyltransferases (EC 2.4.1.x). By the creation of a ugtA1 deletion mutant we could identify that this protein has a clear function in sophorolipid production and enzyme assays on cell lysates provided further evidence that the UgtA1 glucosyltransferase is catalyzing the first glucosylation step in the sophorolipid biosynthetic pathway of *C. bombicola*. We further demonstrated that the second glucosylation reaction is catalyzed by another independent glucosyltransferase and that this transferase is highly specific towards glucolipids as a substrate, since disrupting the UgtA1 activity results in a complete loss of sophorolipid production both in vivo and in vitro. The A113 strain created here is thus no longer capable to convert ω or ω-1 hydroxylated fatty acids to glucolipids and is therefore useful in production of hydroxy fatty acid based compounds. The lack of GTI activity will lead to an intracellular pool of hydroxylated fatty acids which can be used as building blocks for other oleaginous compounds.

Example 3

Identification of the UDP-Glucosyltransferase Gene UGTB1 Responsible for the Second Glucosylation Step in the Sophorolipid Biosynthetic Pathway of *Candida Bombicola* ATCC 22214

Introduction

This strain is knocked-out at the UGTB1 gene (GenBank accession number HM440974), encoding for the enzyme responsible for the second glucosylation step in the sophorolipid biosynthetic pathway. The enzyme transfers glucose from UDP-glucose to a glucolipid, resulting in the production of a sophorolipid.

In this strain, no sophorolipid production is detected, while cell growth and viability is comparable to the wild type (FIG. 2).

Materials and Methods

Strains, Plasmids and Culture Media

*Candida bombicola* ATCC 22214 was used for isolation of the UGTB1 gene and *C. bombicola* G9 (derived from ATCC 22214, see Van Bogaert et al., 2008b) for creation of the ΔugtB1 deletion mutant. *Escherichia coli* DH5α F' was used for plasmid maintenance. Yeast cells were grown on YPD medium containing 1% yeast extract, 2% peptone and 2% dextrose, SD medium containing 0.67% yeast nitrogen base without amino acids (Difco) and 2% glucose or 3C medium containing 10% glucose, 1% yeast extract and 0.1% urea. Liquid media were incubated at 30° C. and 200 rpm. *E. coli* was grown on Luria Bertani medium (0.5% Bacto yeast extract, 1% Bacto Trypton, 0.5% NaCl) containing 0.01% ampicillin and incubated at 37° C. and 200 rpm.

Plasmids were isolated from *E. coli* DH5α F' by means of the MiniPrep Plasmid Isolation kit from Qiagen and sequenced at AGOWA (Germany).

Primer Design and Sequence Analysis

Primer design, sequence analysis and strategy design were performed with the Clone Manager Professional Suite software (Version 8.0). Primers were ordered at Sigma.

Cloning of the Complete UG TB 1 Gene

For isolation of genomic DNA, *C. bombicola* ATCC22214 was grown overnight on 3C medium. Minor amounts of sophorolipids were removed by extracting 500 μl culture samples with one volume ethylacetate. Cell wall was removed enzymatically by incubating with 200 units Yeast Lytic Enzyme (Sigma) in SCE buffer (1M sorbitol, 0.1M sodium acetate and 60 mM EDTA, pH 7.0) for 90 min at 37° C. in presence of 0.75% β-mercaptoethanol. Genomic DNA was isolated from the remaining protoplasts by means of the GenElute™ Bacterial Genomic DNA kit (Sigma).

The complete sequence of the UGTB1 gene was amplified from *C. bombicola* ATCC 22214 genomic DNA by means of the High Fidelity PCR Master Kit (Roche) and the primers GTII−472For and GTII+239Rev (Table 4). The obtained fragment was purified by means of the Qiaquick PCR purification kit (Qiagen) and cloned in pGEM-T® making use of the pGEM-T® Vector System (Promega). This led to the plasmid pGugtB1 Tot which was then used for transformation of *E. coli* DH5α F' according to (Sambrook and Russell, 2001). Correct transformants were isolated after colony PCR and grown in liquid LB for subsequent plasmid isolation.

Creation of the UGTB1 Knock-Out Cassette

The knock-out cassette for the *C. bombicola* UGTB1 gene is based on the integration of the URA3 selectable marker between regions of homology to the 5' and 3' termini of the UGTB1 gene. In a first step, plasmid pGugtB1 Tot is linearized by a double digest with single cutting enzymes AvaI and KasI (New England Biolabs) according to Sambrook (Sambrook and Russell, 2001). In this way a fragment of 100 bp (from by 950-1049 of the insert) is removed from the UgtB1 encoding sequence, leaving sticky fragments at both ends of the linearized vector. The URA3 selection marker was obtained after high fidelity PCR with the PfuUltra High Fidelity PCR system (Stratagene) on plasmid pCbura3 (Van Bogaert et al., 2008). Primers used were ura3infugtB1 F and ura3infugtB1 R (Table 4). These primers contain 15 bp of homology to respectively the 3' and 5' end of the linearized plasmid pGugtB1 Tot. The obtained amplicon was used directly for cloning in the linearized plasmid making use of the In-Fusion Dry Down PCR cloning kit (Clontech). This led to the plasmid pGKO_ugtB1 which now contains the complete *C. bombicola* ATCC22214 URA3 gene (2043 bp) flanked by 949 bp and 961 bp of homologous regions to the UGTB1 5' and 3' sequence respectively. Cloning and subsequent transformation of Fusion Blue competent *E. coli* cells, for maintenance of the plasmid, were done as described in the manual of the kit. *E. coli* transformants were tested by colony PCR for insertion of the URA3 marker in the plasmid and subsequently grown in LB for plasmid isolation. The gene sequence of the URA3 gene was confirmed by sequencing.

Creation of a ΔugtB1 Deletion Mutant

A linear knock-out cassette was produced from plasmid pGKO_B1 by PfuUltra High Fidelity PCR (Stratagene) making use of the primers GTII−472F and GTII+239R (Table 4) since recombination frequency is increased strongly by using linear fragments (Van Bogaert et al., 2008). The obtained fragment was column purified and 1 μg was used for transformation of the ura3⁻ *C. bombicola* G9.

For transformation of *C. bombicola* G9 the protocol as described for *Saccharomyces* was used (Gietz and Schiestl, 1995) with some slight modifications. A 50 mM LiAc solution was used instead of 100 mM, incubation of cells with the cassette before heat shocking occurred for 90 minutes instead of 30 and no DMSO was added. After transformation, cells were plated on SD agar medium and incubated at 30° C. until transformant colonies appeared.

Characterisation of the ΔugtB1 Deletion Mutant

The genotype of the obtained mutants was controlled by yeast colony PCR using the primers KOugtB1 CtrlF and KOugtB1 CtrlR (Table 4) annealing upstream the left-sided recombination site and the URA3 marker respectively. To study the phenotype, mutant yeast colonies were grown in liquid medium as described by Lang et al. (2000) for 48 hours before addition of rapeseed oil (37.5 g/L). Wildtype *Candida bombicola* ATCC 22214 served as a reference.

Seven days after addition of the hydrophobic carbon source, sophorolipid production was verified by extracting 1 ml culture medium with 400 μl technical ethylacetate in presence of 10 μl acetic acid.

After vortexing for 5 minutes, 300 μl of the solvent phase was diluted in 1.7 ml absolute ethanol and analyzed on HPLC-ELSD using a Varian ProStar HPLC (Varian) equipped with a Chromolith® Performance RP-18e column [100 mm (I)×4.6 mm (I.D.)] (Merck) and connected to an Evaporative Light Scattering Detector (Alltech). Compounds were eluted by means of an acetonitril/acetic acid (0.5% in water) gradient (5/95 to 95/5 in 40 min) under constant flow of 1 ml/min. Column temperature was set at 30° C. To check the molecular masses of the produced glucolipids, the same samples were analysed under the same conditions on a Shimadzu LC-10-AD HPLC system connected to a quadrupole mass spectrometer (Waters). Molecules were identified by their native molecular masses after ESI (electron spray ionisation) without collision.

Biocatalytic Function of the UgtB1 Glucosyltransferase

*C. bombicola* ATCC 22214 and the ΔugtB1 deletion mutant B11 were inoculated from 3C agar medium into 5 ml Lang medium and grown overnight at 30° C. and 200 rpm. With this preculture, 50 ml of fresh Lang medium was inoculated with a start OD of 0.2 and incubated the same way during 60 hours. Cells were harvested by centrifugation at 5600 g and 4° C. with a swinging bucket centrifuge and washed with 10 ml distilled water. The pellet was then resuspended in lysis buffer pH 7.7 containing 50 mM $KH_2PO_4$, 5% glycerol, 0.5 mM $MgCl_2$, 0.5 mM DTT and 1 mM PMSF to $OD_{100}$. An equal volume of acid washed glass beads (150-212 μm diameter, Sigma) was added and cells were disrupted by vortexing during 15 minutes with 30 seconds intervals on ice. Soluble protein fractions were used for enzyme assays after centrifugation of the crude lysate at 5600 g at 4° C. Protein concentration in the lysate was determined by means of the BCA™ Protein Assay Kit (Pierce).

UDP-glucose was obtained from Sigma, 17-hydroxy-octadecenoic acid and glucolipid were obtained from sophorolipids as described before (Saerens et al., 2009). All substrate solutions were prepared freshly in 50 mM $KH_2PO_4$, pH 7.7. Enzyme assays contained 2 mM UDP-glucose, 2 mM acceptor and 200 μl fresh protein solution in a total volume of 250 μl. For the blank reactions, buffer replaced either UDP-glucose, acceptor or protein solution. All enzyme reactions were incubated at 30° C. for 3 hours. Reactions were stopped by addition of 200 μl HCl (2N) and glycolipids were extracted with 800 μl diethylether/ethylacetate (1/1) according to Breithaupt and Light (1982). From the solvent phase, 700 μl was recovered, evaporated to dryness and redissolved in 300 μl absolute ethanol before analysis on HPLC as described above. Peak areas were converted to product concentrations and enzyme activity was expressed in μM/mg min.

Results and Discussion

Cloning and Sequence Analysis of the Complete UGTB1 Gene

Preliminary genome sequencing data of *Candida bombicola* ATCC 22214 revealed a putative open reading frame (ORF) of 1299 bp with homology to a huge number of mostly hypothetical UDP-glycosyltransferases/glucuronosyltransferases of microbial origin as shown by a BLASTx homology search (Altschul et al., 1997). Primers were designed 472 bp up- and 239 bp downstream of respectively start- and stopcodon of the putative gene and the complete gene sequence was isolated and cloned into the plasmid pGugtB1 Tot. The gene, referred to as UGTB1 (FIG. 7), encodes a putative protein of 432 amino acids with an estimated molecular mass of 46.2 kDa and estimated pI of 4.98.

Though most *Saccharomyces* promoters lack a clear TATA box, an NT rich TATA-like consensus sequence TATA(A/T)A(A/T)(A/G) could be identified 50-200 bp upstream of highly regulated or stress-induced genes (Basehoar et al., 2004). If comparable different regulatory mechanisms would exist for the transcriptional activation of housekeeping and (stress-) induced genes in *C. bombicola*, one might expect a comparable TATA-like consensus in genes involved in sophorolipid production by this yeast as well, since sophorolipid synthesis is observed under nitrogen limiting conditions (Davila et al., 1992). A clear TATA-like element corresponding to the *Saccharomyces* consensus sequence can be identified 50 bp upstream the UGTB1 startcodon (FIG. 7). In contrast, no clear polyadenylation signal or any other signal element that might be involved in 3'-end formation of yeast mRNA can be found (Guo and Sherman, 1996). Since sophorolipid synthesis is strongly linked to nitrogen limitation, one might expect GATA-like regulatory sequences in the upstream regions of genes involved in this pathway. Such GATA motifs are recognized by GATA-type transcription factors which are strongly activated by depletion of nitrogen (Magasanik and Kaiser, 2002). One typical example of such GATA-type transcription factor is the AreA gene of *Aspergillus nidulans* (Marzluf et al., 1997) and several GATA-like elements are recognized in glycolipid synthesizing genes of *Ustilago maydis* (Hewald et al., 2005). In the 5' upstream region of the UGTB1 gene two possible GATA-like elements can be found (FIG. 7). Taken together, it is very likely that expression of the isolated UGTB1 gene is under control of a regulation system linked to nitrogen metabolism.

Sequence Homology to Other UDP-Glucosyltransferases

Analysis of the UgtB1 protein sequence against the Conserved Domain Database (CDD) (Marchler-Bauer et al., 2009) illustrates that the protein belongs to the polyspecific GT1 family of glycosyltransferases (Campbell et al., 1997; Coutinho et al., 2003) which is characterized by a GT1_Gtf_like conserved domain (CDD/cd03784) and which includes amongst others a group of homologous glycosyltransferases involved in the final stages of vancomycin and chloroeremomycin biosynthesis. These proteins transfer sugar moieties from an activated NDP-sugar donor to the heptapeptide core of the antibiotic. All 14 conserved catalytic amino acids are found in the UgtB1 sequence (FIG. 8). From the alignment with other GT1_Gtf_like proteins, residue H18 is supposed to correspond to the only one conserved amino acid of the acceptor substrate binding pocket while residues G17, T272, N338, G340, G342 and G343 are supposed to make up the 6 conserved amino acids from the UDP binding site of the domain.

Because members of the GT1 family all show the GT-B type topology, this family is taken up into the broad GTB-type superfamily of glycosyltransferases (Breton et al., 2006), characterized by another conserved domain (CDD/cl10013) present in the UgtB1 sequence. Sequence homology to antibiotic-related glycosyltransferases is confirmed by the recognition of a MGT (macrolide glycosyltransferase) conserved multidomain (CDD/TIGR01426) and the hits obtained from a BLASTp homology search against all non-redundant protein sequences available at the NCBI databases. Numerous hits with moderate homology appear to be hypothetical glycosyltransferases from both bacterial and fungal origin arising from the huge number of genome sequencing projects. The highest sequence homology of 57% (38% sequence identity) is found for a hypothetical protein from the plant pathogenic fungus *Sclerotinia sclerotiorum* 1980 (gb/EDN94128). While no biochemical function can be ascribed to most of the matching proteins, a limited number is associated with secondary metabolite production and more specifically to the synthesis of antibiotics (Table 5). These findings suggest that the UgtB1 protein is very likely involved in the biosynthesis of a complex secondary metabolite.

Since rhamnosyltransferase RhlB (gb/L28170) from *Pseudomonas aeruginosa* (Ochsner et al., 1994) and both erythritol β-mannosyltransferase Emt1 (gb/XP_400732) and hydroxypalmitate glucosyltransferase Hgt1 (gb/EAK87174) from *Ustilago maydis* (Hewald et al., 2005; Teichmann et al., 2007) catalyze comparable biochemical steps during the synthesis of other glycolipids and because these proteins (all E.C. 2.4.1.-) are classified within the same GT1 family of glycosyltransferases, it was expected that UgtB1 would show significant sequence homology to those. Surprisingly, an optimal global pairwise alignment using BioEdit Software (matrix blosum 62) (Hall et al., 1999) shows 36% sequence similarity (22% identity) to RhlB, 33.5% (18%) to Emt1 and 33% (19%) to Hgt1, values which are even lower as compared to those for antibiotic synthesizing proteins from bacterial origin (Table 5).

With these characteristics, UgtB1 seems to be very comparable to another UDP-glucosyltransferase referred to as UgtA1 (gb/HM440973) we isolated from *C. bombicola* and to which the first glucosylation step in sophorolipid biosynthesis could be ascribed (results not shown). Therefore, sequence homology between these two proteins was verified by means of another optimal global pairwise alignment (matrix blosum 62). Both proteins showed 45.2% sequence identity and 61% sequence similarity (FIG. 8). Apart from the GT1_Gtf_like conserved residues, which are also present in the UgtA1 sequence, several other amino acids are constitutive. Structure homology models that we created for UgtA1 and UgtB1 suggest that these residues are likely situated either in the neighborhood of the catalytic centre or on outer loops and so suggest their involvement in substrate recognition and orientation.

Creation and Characterization of a ΔugtB1 Deletion Mutant

A linear knock-out cassette was used for transformation of the ura3⁻ *Candida bombicola* G9, derived from the wildtype yeast ATCC22214 (Van Bogaert et al., 2008), and transformants were selected by complementation as a result of disruption of the UGTB1 gene by insertion of the URA3 marker. A couple of days after transformation, several transformants were obtained on the selective plates and 28 were subjected to a colony PCR to check their genotype. As a consequence of primer annealing sites, either double cross-over events or left-sided single cross over events will lead to an amplicon. From the 28 transformants, 13 yielded the expected amplicon. The other mutants probably did arise from right-sided single cross-over events, illegitimate recombination or from recombination of the URA3 marker with the G9 ura3 allele.

Three correct transformants (B11, B14 and B19) were subsequently grown in liquid Lang medium to investigate the influence of the knock-out on sophorolipid production. Wildtype *C. bombicola* ATCC 22214 was used as a reference. The growth of the transformants appeared to be comparable to the wildtype yeast indicating that the UGTB1 gene has no contribution to any pathway in primary metabolism. Seven days after addition of rapeseed oil, production of sophorolipids in the culture media was checked. FIG. 9 shows the results for the wildtype yeast and the B11 mutant (B14 and B19 gave identical results).

Figure 10:
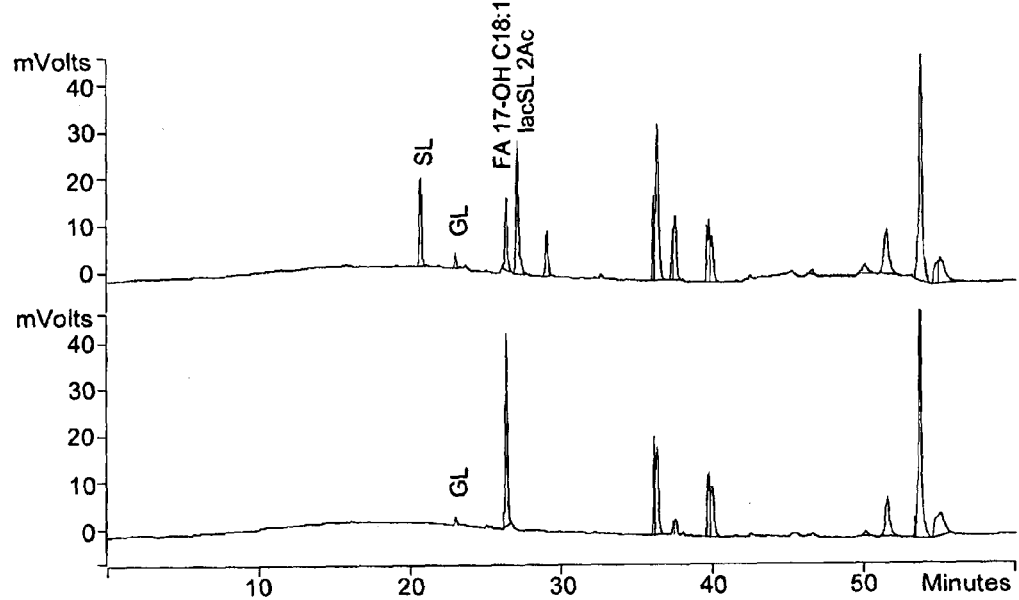
FIG. 10 HPLC-ELSD chromatogram of sample extracts from a glucosyltransferase I assay on soluble protein fractions from wildtype yeast (up) and B11 mutant (down). Peaks at 27 min and 29 min come from de novo sophorolipid synthesis while peaks eluting after 30 min come from co-extracted apolar cell constituents. FA 17-OH C18:1=17-hydroxyoctadecenoic acid, GL=glucolipid (17-O-(β-D-glucopyranosyl)-octadecenoic acid), SL=diacetylated sophorolipid acid (17-O-(2-O-β-D-glucopyranosyl-glucopyranose)-octadecenoic acid), lacSL 2Ac=diacetylated sophorolipid lactone FIG. 11 HPLC-ELSD chromatogram of sample extracts from a glucosyltransferase II activity test on soluble protein fractions from wildtype yeast (up) and B11 mutant (down). Peaks at 27 min and 29 min come from de novo sophorolipid synthesis while peaks eluting after 30 min come from co-extracted apolar cell constituents. FA 17-OH C18:1=17-hydroxyoctadecenoic acid, GL=glucolipid (17-O-(β-D-glucopyranosyl)-octadecenoic acid), SL=diacetylated sophorolipid acid (17-O-(2-O-β-D-glucopyranosyl-glucopyranose)-octadecenoic acid), lacSL 2Ac=diacetylated sophorolipid lactone FIG. 12 Fluorescent signal in function of time for the wild type and the E1 GFP mutant FIG. 13 Molecular map of the amylase synthetic construct, preceded by the partial GAPD promoter FIG. 14 Sequence of the amylase synthetic construct, preceded by part of the GAPD promoter (nucleic acid sequence is SEQ ID NO: 64; amino acid sequence is SEQ ID NO: 65).
Figure 11:
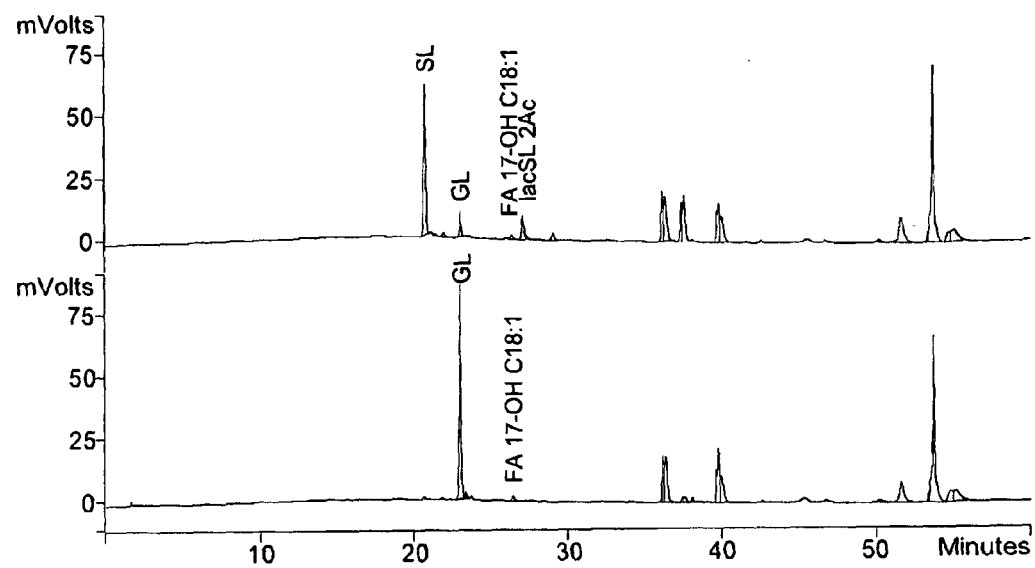

In contrast to the wildtype yeast, no sophorolipids were produced by the ΔugtB1 deletion mutants indicating that UgtB1 has a key-function in sophorolipid production. Instead, the mutants produced glucolipids, indicating that the first glucosylation is still being performed. That UgtB1 is catalyzing the second glucosylation was confirmed by enzyme assays on cell lysates of the wildtype yeast ATCC 22214 and the randomly selected AugtB1 deletion mutant B11. For detection of the glucosyltransferase I activity (GTI), UDP-glucose and 17-hydroxy-octadecenoic acid were used as donor and acceptor respectively. For detection of the glucosyltransferase II activity (GTII), fatty acid was replaced by glucolipid as acceptor. FIG. 10 shows the analyses of sample extracts after a GTI assay on the lysates of wildtype and B11 respectively. In the cell lysate of the wildtype, conversion of the fatty acid to glucolipids by the action of the first glucosyltransferase is followed by a second glucosylation leading to sophorolipids. The peaks at 27 and 29 minutes correspond to diacetylated lactonised sophorolipids from de novo synthesis during incubation in Lang medium. These de novo sophorolipids are absent in the chromatogram of the B11 mutant confirming disruption of the pathway. Since no formation of acidic sophorolipids is observed with the B11 lysate, showing minor formation of glucolipids only, one can conclude that the second glucosylation is blocked in the deletion mutant. This is confirmed by a GTII assay on the same lysates (FIG. 11): where glucolipids are converted to acidic sophorolipids with the lysate of the wildtype, no conversion of glucolipids is observed with the lysate of the B11 mutant. The small peak of fatty acids observed in these chromatograms originates from glucolipid preparation (Saerens et al., 2009).

Conclusion

Knowledge of the genetic mechanisms behind biosurfactant production by different microorganisms is increasing, opening a new way to increase yields by creation of overproducing mutants and in that way make the biosurfactants economically more competitive. The genetics behind sophorolipid production, one of the most promising group of glycolipid biosurfactants, however remains unclear. Here we isolate a gene from the industrially applied C. bombicola with a key-function in this important pathway. The UGTB1 gene encodes the UDP-glucosyltransferase responsible for the second glucosylation step as demonstrated by the creation of a AugtB1 deletion mutant and subsequent in vitro enzyme assays with cell lysates. We demonstrate here that two independent UDP-glucosyltransferases referred to as UgtA1 and UgtB1 act in a stepwise manner. The presence of conserved domains in the UgtB1 protein sequence indicate that the protein belongs to the GT1 family of glycosyltransferases. Surprisingly, sequence homology to bacterial glycosyltransferases involved in antibiotic synthesis is higher than the homology to other glycosyltransferases known so far to be involved in microbial glycolipid biosynthesis. This might be explained by the phylogenetic distance between the different organisms. *Ustilago maydis* for example is a dimorphic Basidiomycete and the clustering of glycolipid synthesizing genes in *Ustilago* suggests that these have arisen from a horizontal gene transfer (Hewald et al., 2006). On the whole however, sequence homology between the UgtB1 and other glycosyltransferases of the GT1 family is low which indicates that the UgtB1 might be considered as a new enzyme within this family.

Example 4

Examples of Produced Components

Example 4.1

Heterologous Protein Expression

A strain derived from *Candida bombicola* ATCC 22214, i.e. a strain knocked-out in the cyp52M1 gene (GenBank accession number EU552419), was used for protein production. In this strain, hardly any sophorolipid production is detected, while cell growth and viability is comparable to the wild type (see example 1).

In order to allow intregration of the heterologous protein gene in the genome and selection for this event, the ura3-negative PT36 strain was used. This strains is derived from the wild type strain *Candida bombicola* ATCC 22214, but only harbors the promotor and terminator of the ura3 gene, while the ura3 coding sequence is removed. This was done by homologous recombination with a cassette containing the ura3 5' upstream non-coding region fused to its 3' noncoding downstream region. The PT36 mutant are auxotrophic for uracil or uridine (ura3⁻) and can be transformed back to prototrophy with a functional ura3 gene. Transformants can be selected on SD medium. The the cyp52M1 gene of the PT36 strain was knocked out as described in Example 1.

Example 4.1.1

Green Fluorescent Protein

Introduction

This strain contains the yEGFP gene which was codon optimised for *Candida albicans* (Cormack et al., 1997). The strong constitutive GAPD promoter from *Candida bombicola* (Van Bogaert et al., 2008a) was used to drive expression of the gene.

Materials and Methods

Strains, Plasmids and Culture Conditions

*Escherichia coli* XL10GOLD ultracompetent cells were used for plasmid maintenance and for all cloning experiments. C. bombicola was cultured on yeast peptone dextrose (YPD) medium (1% yeast extract, 2% peptone, 2% glucose) or on synthetic dextrose (SD) medium (0.67% yeast nitrogen base without amino acids (DIFCO) and 2% glucose). Liquid yeast shake-flask cultures were incubated at 30° C. and 200 rpm. *E. coli* was grown in Luria-Bertani (LB) medium (1% tryptone, 0.5% yeast extract and 0.5% sodium chloride) supplemented with 100 mg/L ampicillin if necessary. Liquid *E. coli* cultures were incubated at 37° C. and 200 rpm. Plasmid pGALyEGFPTU which harbours the yEGFP GFP variant, was obtained from the Laboratory of Molecular Biology, Ghent University (LMBP). This GFP variant contains two mutations (S65G and S72A) relative to the wild type GFP and is additionally codon optimized for the yeast *Candida albicans* (Cormack et al., 1997).

DNA Isolation and Sequencing

The pGEM®-T vector (Promega) was used for all cloning experiments. T4 DNA ligase (Fermentas) and the In Fusion Dry Down PCR cloning Kit (Clontech) were used for cloning and ligation. All restriction nucleases were obtained from New England Biolabs (NEB) and restriction digests were performed as specified by the supplier. Yeast genomic DNA was isolated of overnight yeast cultures grown on YPD. The yeast cell wall was enzymatically removed by incubation of the cell pellet derived from 1 ml of yeast culture with 0.80 g Yeast Lytic Enzyme (Sigma)/g wet cell weight in SCE buffer (1M sorbitol, 0.1M sodium acetate and 60 mM EDTA, pH 7.5) for 90 min at 37° C. in presence of 3.75 µl mercaptoethanol. Genomic DNA was isolated from the remaining protoplasts by means of the DNeasy® Plant Maxi Kit (Qiagen). Plasmid DNA was isolated by using the QIAprep Spin Miniprep Kit (Qiagen). PCR reaction mixtures were purified using the QiAquick PCR Purification Kit (Qiagen) or the column free Sure Clean Plus Kit (Bioline) for PCR fragments larger than 4 kb. The latter was also used for purificationp of restriction mixtures. All DNA sequences were determined at LGC Genomics, Germany.

Primer Design and PCR Reactions

Primer design, sequence analysis and strategy design were performed with the Clone Manager Professional Suite software (Version 8.0). Primers were ordered at Sigma. All high fidelity PCR reactions were performed using the Pfu high fidelity polymerase unless stated otherwise. Colony PCR's both on *E. coli* and *C. bombicola* were performed using Taq polymerase.

Creation of the GFP Expression Cassette

A 'central' vector (pGEM-T_cassette_yEGFP) was created which contained the yEGFP gene flanked at both sides by an approximately 1 kb long sequence for recombination at the genomic P/T ura3 locus in PT mutants of *C. bombicola* ATCC 22214 (described above) and additionally contains the ura3 marker for selection. The vector was constructed in such way that it can be cut open with two unique restriction enzymes of which one (SapI), cuts just before the ATG 'start' codon of the gfp gene. This feature of the vector allows to clone promoter fragments exactly in front of the GFP variant. Hence, a multiple cloning site (MCS3) was constructed of which the sequence was added as a non binding extension to primer P5_FOR_yEGFP_extMCS3 (bold characters in Table 6). This MCS contains 11 unique restriction sites of which two (SapI and AvaI) were used to linearize the vector. The linearized vector was then used for cloning the GAPD promotor in front of the GFP variant using the In Fusion Dry Down PCR cloning kit.

The vector pGEM-T_cassette_yEGFP was constructed in eight steps. First the 5'UTR of the ura3 gene (including the ura3 promotor), the ura3 coding sequence and ura3 3'UTR (including the ura3 terminator) were amplified as one PCR fragment (1970 bp) from genomic DNA of wild type *C. bombicola* ATCC 22214, using primers P1_FOR_URA3v and P2_REV_URA3v. Since the pGEM-T vector was used for cloning the High Fidelity PCR Master Kit (Roche) was used for amplification. This first PCR fragment (PRODUCT 1) provides the final cassette with 1000 base pairs needed for homologous recombination in PT mutants of *C. bombicola*, while at the same time providing the cassette with a selection marker. This resulting vector pGEM-T_ura3* still contained a SapI recognition site, which was originally present in pGEM-T. This recognition site needed to be removed to make SapI a unique restriction enzyme. The latter was done using the Quick Change Site Directed Mutagenesis kit (Stratagene) with the mutagenesis primerpair P7_FOR_QCSapIpGEM-T and P8_REV_QCSapIpGEM-T. The SapI recognition site '5-GCTCTTC-3' was thus transformed into the following sequence: '5-GCTCCTC-3' which will not anymore be recognised by the SapI restriction endonuclease rendering the SapI recognition site of MCS3 unique. The resulting vector was named pGEM-T_ura3.

A second step involved the amplification of the 3' UTR of the ura3 gene from genomic DNA using primers P3_FOR_URA3t_extyEGFP and P4_REV_URA3t_extNotI (PRODUCT 2) and amplification of the yEGFP variant and *Candida albicans* MAL2 terminator from pGALyEGFPTU using primers P5_FOR_yEGFP_extMCS3 and P6_REV_yEGFP_extURA3t. The multi cloning site MCS3 and a NotI restriction site were added to PRODUCT3 and PRODUCT2 respectively by non binding extensions on primers P4_REV_URA3t_extNotI and P5_FOR_yEGFP_extMCS3. PRODUCT3 and PRODUCT2 were subsequently fused together by overlap PCR. The template PCR products already contained the fifteen necessary complementary base pairs for performing overlap PCR which were added as non binding extensions on primers P3_FOR_URA3t_extyEGFP and P6_REV_yEGFP_extURA3t. Template PCR products were cleaned up using the Qiaquick PCR Purification Kit, concentrations were measured and three PCR reactions were set up with different template concentrations; 0.5 ng, 5 ng and 50 ng of PRODUCT2 and PRODUCT3 were added to three separate PCR tubes. Subsequently, fifteen primerless PCR cycles were conducted following the next temperature program; an initial denaturation at 95° C. for 2 min; a 15-fold repeat of the following three steps: 95° C. for 30 sec, a specific annealing at 60° C. for 30 sec and an elongation step at 72° C. for 3 min. These fifteen cycles were followed by a final elongation step at 72° C. for 7 min. After this first primerless PCR, 3 µl of each of the two primers for amplification of the fusion product, P5_FOR_yEGFP_extMCS3 and P4_REV_URA3t_extNotI, was added to each of the PCR tubes. Next, 30 regular PCR cycles were performed. The fusion PCR product, P3_P2 (=2275 bp), was subsequently cut with SpeI and NotI as was the vector pGEM-T_ura3. Vector and insert were subsequently ligated using T4 DNA ligase and the ligation mixture was transformed into XL10Gold competent *E. coli* cells. The resulting vector was named pGEM-T_cassette_yEGFP.

The constructed vector was subsequently used to clone the GAPD promoter in front of the yEGFP start codon. The vector was linearized using the SapI and AvaI restriction nucleases and the In Fusion Dry Down PCR Cloning Kit was used to clone the promoter into the linearized vector. For this purpose the promoter was provided with the fifteen base pairs necessary for cloning linear PCR fragments into a linearized vector. These were added as non binding fragments on the primers P18_REV_GAPDprom and P19_FOR_pGAPD1560 used for promoter amplification from genomical DNA of *C. bombicola* and are depicted bold in Table 6. The constructed vector was named pGEM-T_pGAPD1555_yEGFP.

Transformation

Yeast cells were transformed by standard electroporation. Linear DNA for transformation was obtained by standard PCR with the primers P1_FOR_URA3v and P31_REV_cassette (Table 6). Transformants were selected on SD plates. *E. coli* cells were transformed as described by Sambrook (Sambrook et al., 2001) and selection occurred on LB plates supplemented with ampicillin.

Fluorometry

Fluorescence was measured using a Spectramax Gemini XS device (Molecular Devices, St. Gregoire, France) with black 96-well plates. Fluorescence emission was measured at 511 nm after excitation at 488 nm and was quantified in relative fluorescence units (RFU's). Cultures were grown on SD and before measuring fluorescence. The wild type *C. bombicola* ATCC 22214 was uses as a blank reference.

Results

*C. bombicola* was transformed with the GFP expression cassette as described in the material and method section. After five days of incubation colonies appeared on the selective SD plates. Colony PCR was performed with the primerpair P37_FOR_checkGFP and P35_REVcheckcasIN and one positive colony was obtained. The genomical DNA of mutant E1 (*Candida bombicola*_pGAPD1555_yEGFP) was isolated and several control PCR's were performed to check for the correct genotype. These control PCR's confirmed that the mutants contained the complete integration cassettes.

Three biological replica's of the mutant and WT respectively were grown on 3 mL SD medium in deep 24-well plates at 30° C., 200 rpm. The wells were inoculated to the same OD (0.2) from precultures on SD started from single colonies. Several samples were taken throughout the growth curve. 100 microliter (×2) of each well was put into a black 96 well plate and fluorescence was measured after excitation at 488 nm. Blanc values obtained for the wild type were substracted from the fluorescence values of the mutant and WT respectively (background) and the obtained values were plotted against the incubation time.

Figure 12:
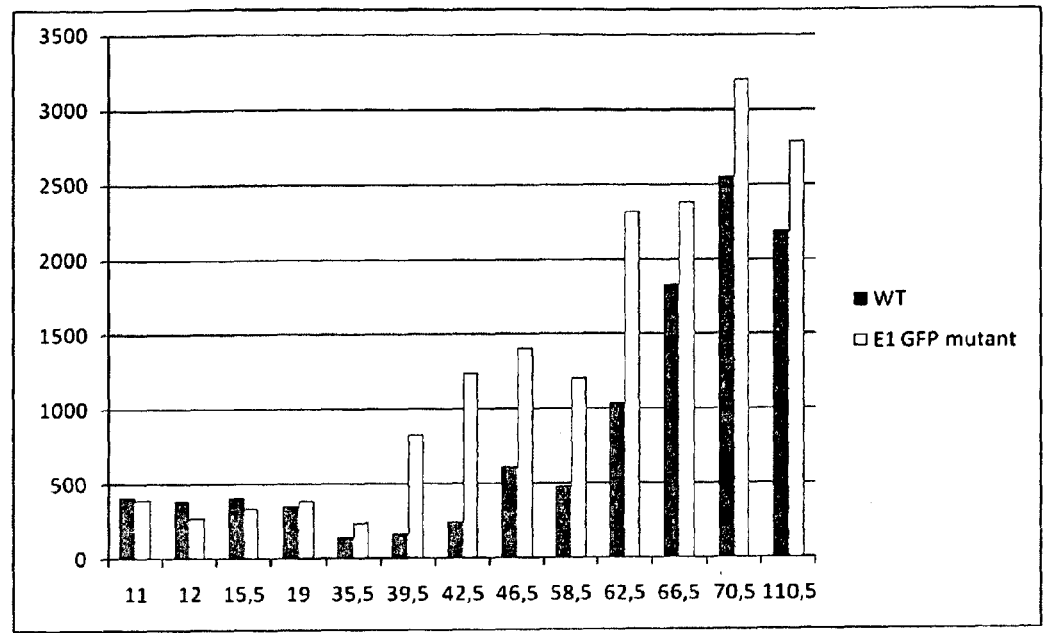

As can be seen in FIG. 12 a significant fluorescent signal was detected between 40 and 63 hours of incubation.

Example 4.1.2

Amylase

Introduction

In order to explore its capabilities to produce (heterologous) enzymes, the sophorolipid negative *Candida bombicola* ATCC 22214 cyp52M1 was tested as to its production of an—amylase.—Amylases constitute an important class of enzymes which find many biotechnological applications in processes which involve, for example, the degradation of starch and the determination of soluble and insoluble dietary fiber in rice and wheat bran. Such applications are found in baking, brewing, detergents and textile industries (Roy et al., 2000). In baking, for example, -amylases are used because they increase the bread volume, because they improve the crumb grain, crust, and crumb color, and for their flavor development promoted in the final product (Rosell et al., 2001). The—amylase is an endo-enzyme that randomly hydrolyses the—1,4 glucosidic linkages in polysaccharides.

For heterologous expression in *Candida bombicola*, the α-amylase from *Aspergillus oryzae* (amy3) has been selected. The strong constitutive GAPD promoter from *Candida bombicola* (GenBank accession number EU315245) was used to drive expression of the gene. In order to get the enzyme secreted, an N-terminal secretion signal has been provided (the *S. cerevisiae* α mating factor secretion signal). Since codon usage of *A. oryzae* significantly differs from that in *C. bombicola*, and *C. bombicola* has no multiple exon-intron genes, a codon optimized cDNA sequence has been designed.

Materials and Methods

Strains, Plasmids and Culture Conditions

*C. bombicola* knocked-out in the cyp52M1 gene and in the ura3 gene (PT36 strain) was used for amylase expression. More specific, the amylase expression cassette was used to transform a sophorolipid negative, auxotrophic ura3⁻ *C. bombicola* 'PT mutant' (described in the introduction of example 4).

*Escherichia coli* DH5α was used in cloning experiments and for plasmid maintenance.

Plasmid pGEM-T_pGAPD1555_yEGFP (as described in Example 4.1.1: production of the protein GFP in *Candida bombicola*) was used as vector backbone. This vector contains a bacterial selection marker (AmpR) and origin of replication, a functional copy of the *C. bombicola* ura3 gene, and the yEGFP gene. Transcription of the yEGFP is controlled by 1560 bp of the *C. bombicola* GAPD promoter region (GenBank accession number EU315245) and the *Candida albicans* MAL2 terminator (GenBank accession number M94674). The promoter-yEGFP-terminator construct is flanked at both sides by an approximately 1 kb long sequence for recombination at the genomic PT ura3 locus in PT mutants of *C. bombicola* ATCC 22214, being the functional copy of the *C. bombicola* ura3 gene at the 5' upstream side.

For routine experiments, yeast cells were grown on YPD medium (1% yeast extract, 2% peptone and 2% dextrose), while selection after transformation was performed on synthetic dextrose (SD) medium (0.67% yeast nitrogen base without amino acids (DIFCO) and 2% glucose) and amylase production was performed on 3C medium with 3% sucrose (10% glucose, 1% yeast extract, 0.1% ureum, 3% sucrose). Yeast cultures were incubated at 30° C. and 200 rpm.

*E. coli* cells were grown in Luria-Bertani (LB) medium (1% trypton, 0.5% yeast extract, 0.5% sodium chloride (and 15% agar for plates)) supplemented with 100 mg/L ampicillin. *E. coli* cultures were incubated at 37° C. and 200 rpm.

Standard DNA Manipulation

Routine recombinant DNA methodology was performed according to Sambrook & Russell (2001) (Sambrook and Russell, 2001). DNA concentrations were measured with the NanoDrop® ND-1000 UV-Vis Spectrophotometer (Nano-Drop Technologies). The 2-Log ladder of Westburg BV was used to control the length of DNA products. PCR reactions were performed with standard Taq-DNA polymerase (Westburg BV) or with the PfuUltra™ High-Fidelity DNA Polymerase AD (Stratagene) according to the procedure described by the manufacturer. Gel fragments were purified with the Qiaexll Gel Purification kit (Qiagen). Ligation was performed with the T₄ DNA ligase of Fermentas, according to the manufacturer's protocol. Plasmid DNA was isolated with the QIAprep Spin Miniprep Kit (Qiagen). Sequencing was performed at AGOWA (LGC genomics). Primer design, sequence analysis and strategy design was done with the Clone Manager Professional Suite Software (Version 8.0). All primers were obtained from Sigma-Aldrich Co. Restriction enzymes were obtained from New England Biolabs (Westburg BV) and were used as indicated by the manufacturer.

Creation of the Amylase Expression Cassette

Figure 13:
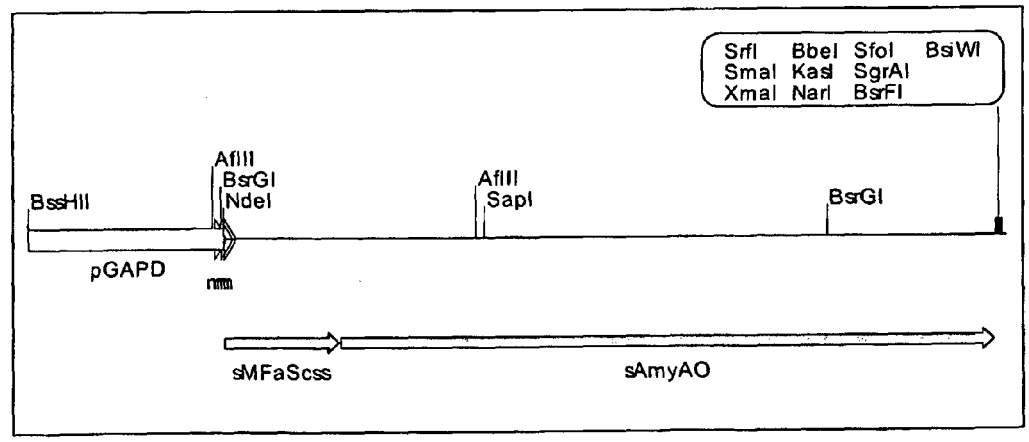

Since codon usage of *A. oryzae* significantly differs from that in *C. bombicola*, and *C. bombicola* has no multiple exon-intron genes, a codon optimized cDNA sequence was designed (FIG. 13). The protein sequence of the mature α-amylase from *Aspergillus oryzae* (TAKA-amylase A, EC 3.2.1.1., encoded by amy3, Genbank accession number CAA31220.1) was back translated using the averaged codon usage of 10 *C. bombicola* genes known to be well expressed. In the synthetic construct, the amylase coding sequence (sAmyAO) is preceded by the sequence coding for 85 amino acids of the *S. cerevisiae* α mating factor secretion signal (GenBank accession number NP_015137), which was also back translated for codon optimization (sMFaScss). Part of the *C. bombicola* GAPD promoter (GenBank accession number EU315245) was placed 5' upstream to the synthetic construct (pGAPD). Finally, some mutations were made to introduce a multi cloning site in front of the ATG start codon and at the 3' end of the coding sequence. The final sequence of the ordered construct is given in FIG. 14. The construct (2153 bp) was ordered as such at GenScript (Piscataway, USA) and obtained cloned at the EcoRI site in plasmid cloning vector pUC57.

Figure 15:
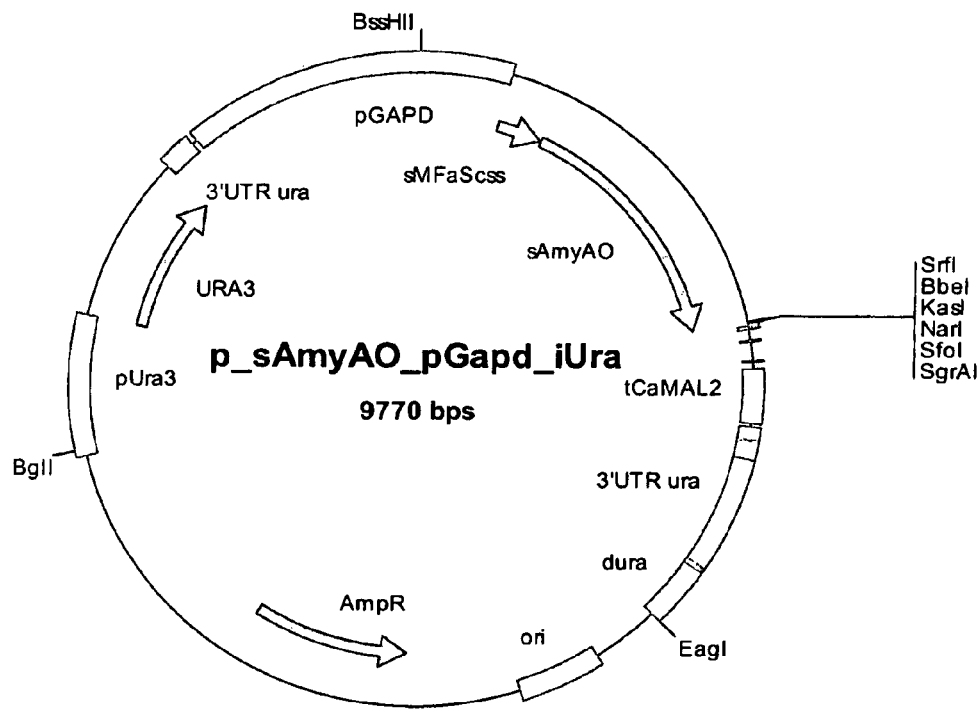
FIG. 15 Vector p_sAmyAO_pGapd_iUra

The synthetic amylase expression cassette was isolated from the pUC57 by restriction with BssHII and BsiWI. The vector backbone pGEM-T_pGAPD1555_yEGFP was cut with BssHII and BsrGI, creating compatible ends. After gel extraction, the amylase expression cassette was ligated in the pGEM-T_pGAPD1555_yEGFP vector backbone, resulting in vector p_sAmyAO_pGapd_iUra (FIG. 15). The ligation mixture was transformed in *E. coli* Dh5, and positive colonies were selected by colony PCR with primers sAmyAOfw and sAmyAOry (Table 7). The sequence of the constructed plasmid was confirmed by sequencing at Agowa (LCG Genomics). Plasmid p_sAmyAO_pGapd_iUra is the same as pGEM-T_pGAPD1555_yEGFP, but the yEGFP coding region has been replaced by the amylase coding region (and secretion signal).

Prior to transformation, the amylase expression cassette together with the ura3 marker (6426 bp) was linearised from the p_sAmyAO_pGapd_iUra plasmid by restriction with BglI and EagI. The linearised cassette contained regions for homologous recombination at the ura3 locus, approximately 1 kb long (FIG. 15).

Yeast Transformation and Verification of Transformants *C. bombicola* cells were transformed with the lithium acetate method (Gietz et al., 1995), but 50 mM LiAc was used instead of 100. Transformants were selected on synthetic dextrose (SD) plates (uracil prototrophy restored with *C. bombicola* ura3).

Yeast colony PCR was performed with Taq DNA polymerase (Westburg BV), according to the manufacturer's protocol, with the exception that initial denaturation was performed for 7 minutes.

Amylase Enzyme Test

Samples of 200 μL were taken from the 3C+3% sucrose cultures. After OD measurement, the samples were pelleted by centrifugation at 12000 rpm during 3 minutes. The supernatant was used for enzyme assays with the amylase test kit AMYL® (Roche Diagnostics).

The enzyme test mixture contained 1 µL sample, 50 µL $R_1$, 10 µL $R_2$, and 139 µL citrate-phosphate buffer, pH 7.0. The mixture is incubated in the spectrophotometer at 37° C. The absorbance is measured every 30 s during 30 minutes.

One unit amylase is defined as the amount of enzyme able to raise the $OD_{405\ nm}$ by 1 during 15 minutes in a reaction mixture consisting of 1 µL sample+50 µL $R_1$+10 µL $R_2$+139 µL buffer incubated at 37° C.

Results

The amylase expression cassette, together with the ura3 marker, was constructed as described in the "Materials and Methods" section. This linear fragment (6426 bp) was used to transform sophorolipid and uracil/uridine negative *Candida bombicola* PT cells. One colony appeared on the selective SD plates after 4-10 days of incubation. The genotype of this transformant was checked by yeast colony PCR with 2 primer pairs. First, primers sAmyAOfw and sAmyAOry (Table 7) were used, both annealing in the amylase encoding region of the cassette. In this way, integrity of the amylase expressing part was ensured. The second primer pair used was sAmyAOfw2 and P35 (Table 7). Primer sAmyAOfw2 binds in the amylase encoding region, while the latter binds outside the homologous regions of the cassette, on genomic DNA. Thus, correct integration of the cassette at the ura3 locus is checked. The colony showed the correct genotype and is further referred to as 'SL⁻Amy⁺'.

Figure 16:
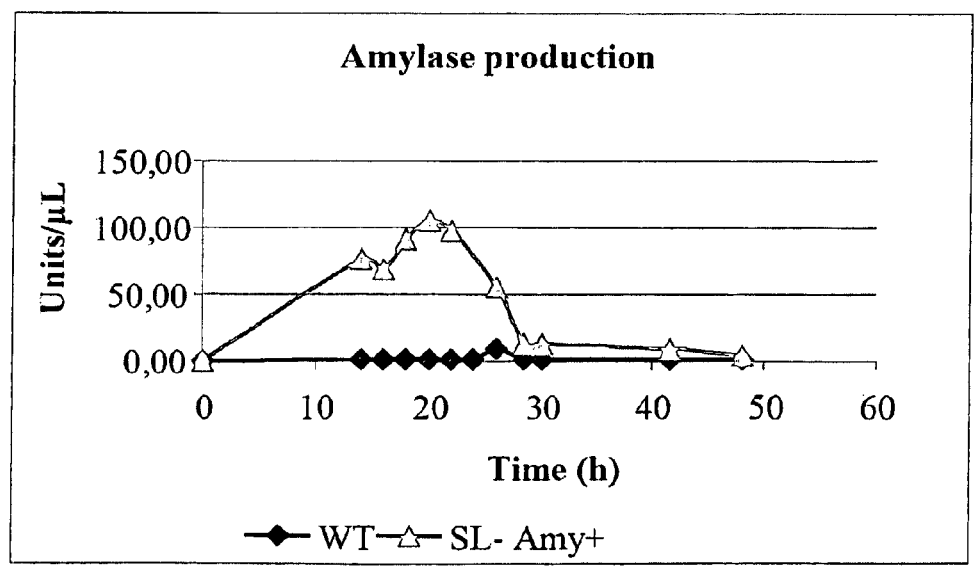
FIG. 16 Amylase production by the sophorolipid negative amylase transformant (SL– Amy+) and the wild type (WT) of *C. bombicola*
Figure 17:
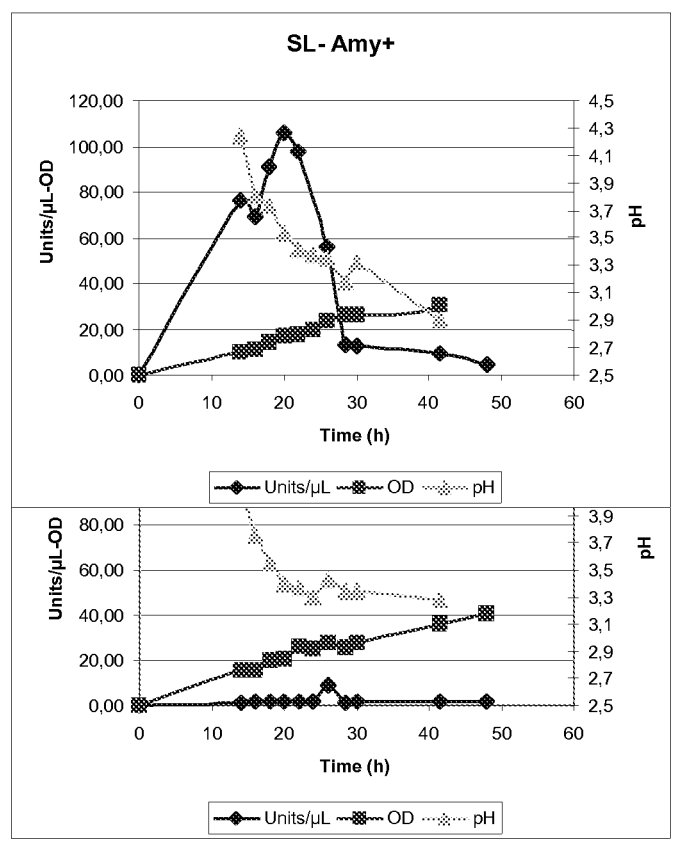
FIG. 17 Metabolic profile of the sophorolipid negative amylase transformant (SL– Amy+, left) and the wild type (WT, right) of *C. bombicola*

The 'SL⁻Amy⁺' transformant and the wild type were subsequently grown on 3C medium with 3% sucrose. The amylase production, cell growth (OD 600 nm) and pH of the cultures were followed during 48 h, taking samples approximately every 2 hours. Amylase enzyme tests were performed as explained in the "Materials and Methods" section. The results of this growth and production test are depicted in FIGS. 16 and 17. From FIG. 16, it is clear that the 'SL⁻Amy⁺' transformant produces amylase, up to 106 units/µL culture supernatant, while the wild type strain does not produce any amylase (9 units/µL maximum, background). The growth and pH curves (FIG. 17) are similar for both strains, though the pH drops lower in the 'SL⁻Amy⁺' transformant culture at the very end of the test. Amylase production has no negative effect on the growth of *C. bombicola*. In conclusion, an amylase expression transformant was created which is knocked out in sophorolipid production but instead produces -amylase, up to 106 units/µL culture supernatant when grown on 3C medium with 3% sucrose. The wild type strain did not produce any amylase. This is the first time (extracellular) enzyme production is described for a sophorolipid negative strain of *C. bombicola*.

Example 4.2

Creation of a Strain Synthesising Polyhydroxyalkanoates

Introduction

This strain is knocked-out in the cyp52M1 gene (GenBank accession number EU552419) mentioned above and instead carries a PHA synthase (phaC1) gene of which expression depends on the up- and downstream regulatory sequences of the cyp52M1 gene. The protein sequence of $PHAC1_{pr}$ (ENA accession number AAD26365.2) from *Pseudomonas resinovorans* was backtranslated using the averaged codon usage of the genes of the sophorolipid pathway. The resultant strain does not produce sophorolipids anymore but instead produces MCL-polyhydroxyalkanoates (PHA) when grown on glucose with addition of rapeseed oil. Cell growth and viability of said strain is comparable to the wild type.

Materials and Methods

Strains, Plasmids and Culture Conditions

*Candida bombicola* ATCC 22214 was used for isolation of the ura3 gene with up- and downstream regulatory sequences and for isolation of the downstream region of the cyp52M1 gene (downCYP). The auxotrophic ura3⁻ *Candida bombicola* PT36 strain (which is described under Example 4.1.1) was used for insertion of the PHA expression cassette. Yeast cells were grown on YPD medium (1% yeast extract, 2% peptone and 2% dextrose), SD medium (0.67% yeast nitrogen base without amino acids (Difco), 2% glucose), 3C medium (10% glucose, 1% yeast extract, 0.1% ureum and 15% agar) or the medium described by Lang (Lang et al., 2000) to which rapeseed oil (Sigma) was added after 48 h when mentioned. Yeast cultures were incubated at 30° C. and 200 rpm.

*Escherichia coli* DH5α or XL1 OGOLD were used in the cloning experiments and transformation occurred as described by Sambrook and Russell (2001). *E. coli* cells were grown in Luria-Bertani (LB) medium (1% trypton, 0.5% yeast extract, 0.5% sodium chloride (and 15% agar for plates)) supplemented with 100 mg/L ampicillin. Liquid *E. coli* cultures were incubated at 37° C. and 200 rpm.

DNA Isolation and Sequencing

Yeast genomic DNA was isolated with the GenElute™ Bacterial Genomic DNA Kit (Sigma) of overnight yeast cultures grown on YPD. The yeast cell wall was enzymatically removed by incubation of the cell pellet derived from 1 ml of yeast culture with 0.80 g Yeast Lytic Enzyme (Sigma)/g wet cell weight in SCE buffer (1M sorbitol, 0.1M sodium acetate and 60 mM EDTA, pH 7.5) for 90 min at 37° C. in presence of 3.75 µl mercaptoethanol. Genomic DNA was isolated from the remaining protoplasts by means of the GenElute™ Bacterial Genomic DNA kit (Sigma).

Bacterial plasmid DNA was isolated with the QIAprep Spin Miniprep Kit (Qiagen). All PCR products were cloned into the pGEM-T® vector (Promega) or derivatives of it and send as such to AGOWA (LGC genomics) for sequence analysis. The pGEM-T® vector was the backbone of all constructed vectors. When necessary DNA was isolated from gel using the QIAquick Gel Extraction Kit (Qiagen).

Primer Design and PCR Reactions

Primer design, sequence analysis and strategy design were performed with the Clone Manager Professional Suite software (Version 8.0). Primers were ordered at Sigma. All high fidelity PCR reactions were performed using the Pfu high fidelity polymerase. Colony PCR's both on *E. coli* and *C. bombicola* were performed using Taq polymerase.

Transformation

*C. bombicola* cells were transformed using a standard electroporation protocol. Transformants were selected on SD plates. *E. coli* cells were transformed as described by Sambrook (Sambrook et al., 2001) and selection occurred on LB plates supplemented with ampicillin.

Synthetic Construct

The PHAC1 protein sequence from *Pseudomonas resinovorans* (ENA accession number AAD26365.2) was backtranslated using the average codon usage of the genes of the SL-pathway which was determined using an online tool (Stothard, 2000). An SKL (TCTAAGCTG) peroxisomal target sequence (PTS) was added at the 3' terminus of the gene as well as the up- and downstream regulatory regions of the cyp52M1 gene respectively at the 5' (488 bp) and 3' (190 bp) side of the codonoptimised phac1 sequence. The 5' UTR regio was extended to 1098 bp to obtain enough homology for homologous recombination at the cyp52M1 locus. The construct was ordered as such at GenScript (Piscataway, USA) and obtained cloned in a vector. The construct was amplified with the primers P55_FOR_upCYP_extNheI and P58_REV_PHAC1+tCYP_extEcorI (Table 8) yielding a fragment of 2986 bp. The primers respectively contained NheI and EcorI extensions so that the fragment could be subsequently digested with said restriction enzymes for further subcloning of the synthetic construct.

Creation of the PHA Expression Cassette

Figure 18:
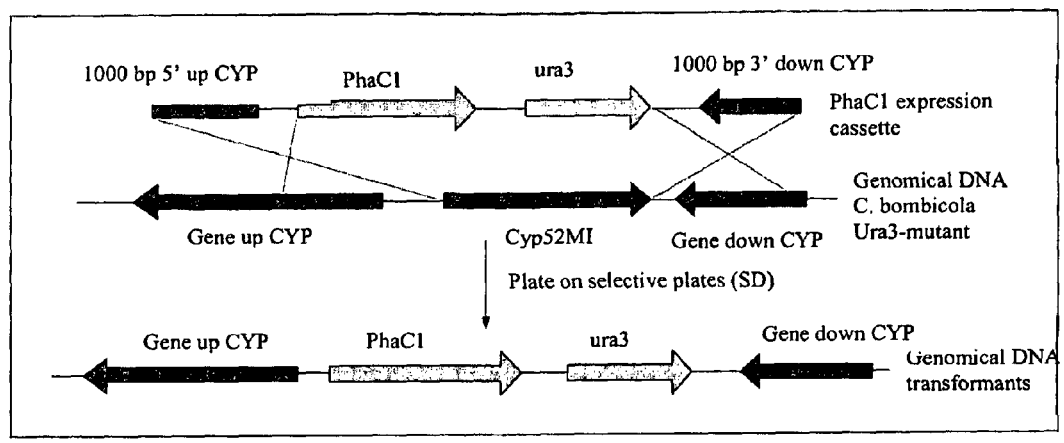
FIG. 18 PHA expression cassette and its integration at the cyp52m1 locus

The expression cassette contained the codon optimised phaC1 gene and ura3 marker and was constructed in such way that it contained the up- and downstream regio's of the cyp52M1 gene for homologous recombination at the cyp52M1 locus in the genomic DNA of an auxotrophic C. bombicola PT36 strain. Construction of the cassette occurred in three steps. First the region for homologous recombination at the 3' end of the cyp52M1 gene (downcyp) was amplified from genomic DNA of C. bombicola using primers P53_FOR_downCYP_extSpeI and P54_REV_downCYP_extNotI (Table 8). The resulting amplicon and the pGEM-T®_ura3 vector (cfr. Example 4.1.1) were digested with the unique cutters SpeI and NotI and subsequently ligated using T4 ligase (NEB). Secondly the resulting vector was digested using the unique cutters NheI and EcorI. This double restriction yielded two fragments (5644 bp and 358 bp) of which the largest one was gel purified and subsequently ligated with the amplified synthetic construct which was first subjected to restriction with the same restriction enzymes. In a third and last step the expression cassette was amplified using primers P63_FOR_cassPHAC1 and P64_REV_cassPHAC1 and the linear PCR fragment was purified and used for transformation of the C. bombicola PT36 strain (FIG. 18). Transformants were selected on SD plates.

Sampling

Analytical sophorolipid samples were prepared as follows: 440 μL ethylacetate and 11 μL acetic acid were added to 1 mL culture broth and shaken vigorously for 5 min. After centrifugation at 12000 rpm for 5 min, the upper solvent layer was removed and put into a fresh eppendorf tube with 700 μL ethanol. Samples were analysed by HPLC and Evaporative Light Scattering Detection.

Cell dry weight (CDW) was measured by transferring 2 mL culture broth to a cellulose nitrate filter with a pore diameter of 0.45 μm (Sartorius) and the dry weight was determined in the XM60 automatic oven from Precisa Instruments Ltd.

PHA hydrolysis and fatty acid methyl ester (FAME) formation was performed by performing acid methanolysis of 30 mg of freeze-dried cell material in a 4 ml 1:1 chloroform/methanol+3% $H_2SO_4$ mixture at 95° C. for 4 h. Before methanolysis cells were harvested (4000 rpm, 4° C.) from flask cultures after which the cell pellets were frozen at −80° C. and lyophilised for 24 h. 30 mg of the resulting freeze-dried material was washed several times with 25 ml of hot methanol (65° C.) to remove oil and free fatty acids. After methanolysis 4 ml 0.9% (wt/vol) NaCl was added to the tubes and the organic phase was collected for analysis on GC-MS. 1 mg of internal standard (2-hydroxyhexanoic acid) was added before methanolysis and 1 mg of external standard (12-hydroxydodecanoic acid) was added just before injection of the samples.

HPLC-Analysis of Sophorolipids

Sophorolipid samples were analysed by HPLC on a Varian Prostar HPLC system using a Chromolith® Performance RP-18e 100-4.6 mm column from Merck KGaA at 30° C. and Evaporative Light Scattering Detection (Alltech). A gradient of two eluents, a 0.5% acetic acid aqueous solution and acetonitril, had to be used to separate the components. The gradient started at 5% acetonitril and linearly increased to 95% in 40 min. The mixture was kept this way for 10 min and was then brought back to 5% acetonitrile in 5 min. A flow rate of 1 mL/min was applied.

GC-MS Analysis of FAMES

The GC (TraceGC ultra, Interscience) contains a 0.25 mm Rxi®-1 ml column (Restek) which is coated with dimethyl polysiloxane. The used carrier gas was helium. The following temperature profile was used: 2 minutes at 64° C. followed by a linear increase of 30° C./min to 200° C. When the column reached 200° C. a second linear increase of 50° C./min to 310° C. took place. De eluting compounds were subsequently injected into the MS (DSQ, Interscience) where they were ionized and detected for further identification. The latter was done using the Xcalibur software which was coupled to the NIST MS Search 2.0 bibliotheca. Only compounds between 40 en 650 g/mol were detected.

Results

The PHA expression cassette was constructed as described in the "Materials and Methods" section. This linear fragment was used to transform Candida bombicola PT36 cells (FIG. 18). 16 colonies appeared on the selective SD plates after 4-11 days incubation. The genotype of these 16 transformants was checked by yeast colony PCR with the primer pair P9_FOR_seqQCSapI_URA3down binding on the expression cassette and A21totRev, binding on the genomic DNA downstream of the right recombination site (Table 8). Ten of the colonies showed the correct genotype. Two other colony PCR's were performed on the positive colonies to control for correct insertion of the cassette. Genomical DNA of one mutant (A8) was subsequently isolated and a PCR reaction was performed with primer pair UDPGTA1R and A21TotRev binding on the genomic DNA of C. bombicola just up- and downstream of the left and right recombination sites respectively. This PCR fragment was sent for sequencing and analysis revealed that the PHA expression cassette was correctly and completely integrated at the cyp52M1 locus of C. bombicola and contained no errors.

The A8 mutant was subsequently grown on the medium described by Lang. Three biological replicas were supplemented with rapeseed oil after 48 h of incubation, three others weren't. Each shake flask was inoculated from a different preculture from overnight grown cultures on Lang medium (5 mL) inoculated from one colony of a 3C plate. The wild type was grown in parallel as a control. Samples for SL extraction were taken throughout the growth curve as were samples for glucose consumption and CDW determination. Thirteen days after addition of the oil the cells were harvested and PHA hydrolysis and conversion to FAMES was performed as described in the "Material and Methods" section.

The effect of the disruption of the cyp52M1 gene was similar as this described in Example 1. CDW and growth were similar for the PHAC1 expression mutant and the wild type and glucose consumption in stationary phase was slower for the PHAC1 expression mutant. Whereas there clearly was sophorolipid production for the wild type, no sophorolipids could be detected in the medium for the PHA expression mutant with or without addition of oil.

Figure 19:
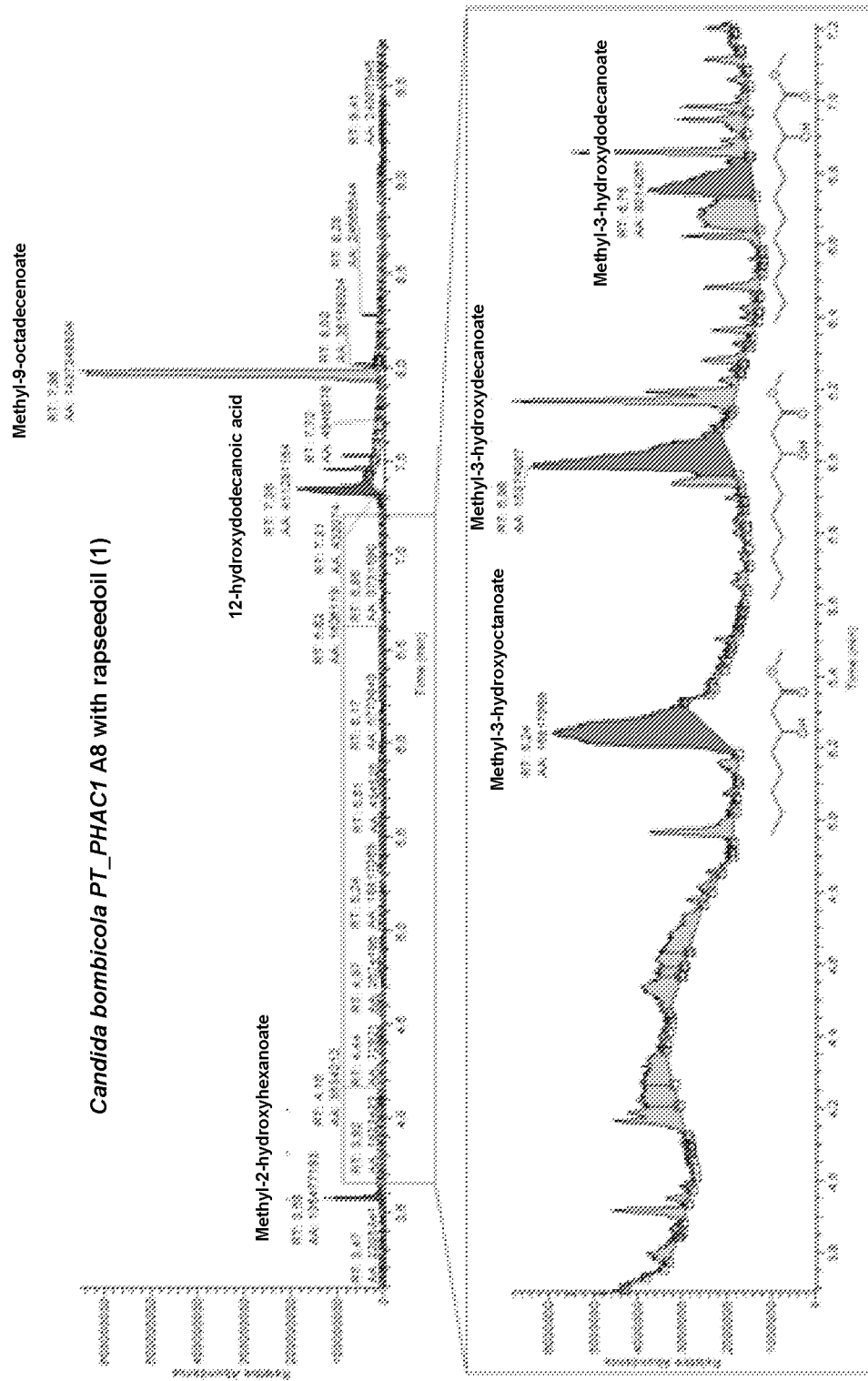
FIG. 19 GC-MS analysis of the FAMES derived from end samples of the *Candida bombicola* PHAC1 A8 mutant grown on Lang medium with addition of rapeseed oil after 48 h of cultivation FIG. 20 Mass spectra of the three predominant glucolipids as found in a B11 culture extract 14 days after cultivation on rapeseed oil (37.5 g/L).
Figure 19:
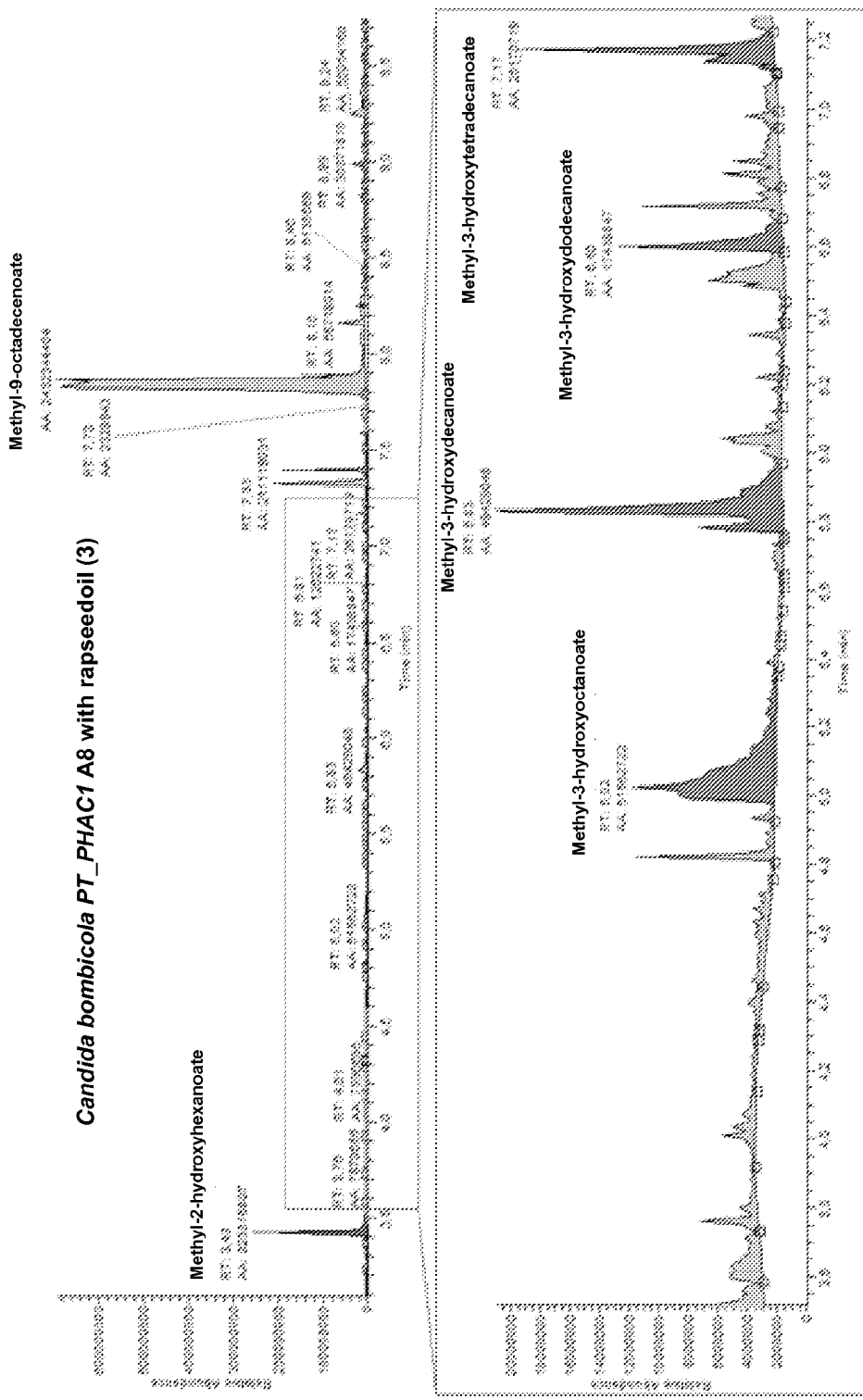

GC-MS analysis of the FAMES derived from end samples of the growth experiment of the PHAC1 A8 mutant (see materials and methods) to which rapeseed oil was added led to identification of compounds derived from MCL-PHA produced in the Candida bombicola PHAC1 A8 mutant (FIG. 19). Three compounds derived from PHA were detected in two of the three biological replicas: 3-methylhydroxyoctanoate (0.50% wt/dwt), 3-methylhydroxydecanoate (0.54% wt/dwt) and 3-methylhydroxydodecanoate (0.32% wt/dwt) with a total of 1.36 wt/dwt PHA. In the third biological replica 3-methylhydroxytetradecanoate was additionally detected (0.50% wt/dwt) and the amounts of the other PHA-monomers were slightly higher for this flask: 3-methylhydroxyoctanoate (0.64% wt/dwt), 3-methylhydroxydecanoate (0.73% wt/dwt) and 3-methylhydroxydodecanoate (0.29% wt/dwt) with a total amount of 2.16% wt/dwt PHA. These peaks were not detected for the samples derived from the wild type cultures (with and without addition of rapeseed oil) nor for the samples from the PHAC1 A8 mutant to which no rapeseed oil was added. Hence the peaks were not derived from intermediates of the beta-oxidation which were converted to FAMES during methanolysis. The rapeseed oil was needed as a lipogenic source to produce the PHA (in substantial amount). The amount of produced PHA was quantified using an internal standard (2-hydroxyhexanoic acid)) which was added to the samples before methanolysis.

The cyp52M1 regulatory sequences drove expression of the PHAC1 gene in this experiment. It was further found that a substantial glucose concentration, in combination with N or P starvation, is needed to activate this promoter. Glucose on the other hand represses expression of the genes of the beta-oxidation. To obtain higher PHA production the catalase (pCTA) and isocitrate lyase (pICL) promoters are isolated from the genome and PHAC1 expression is derived from these promoters which are repressed by high glucose concentrations. Disruption of the beta-oxidation and feeding with substrates with long (C16 and C18) chain length leads to the production of PHA composed only of C18 and/or C16 monomers.

In conclusion, a PHAC1 expression mutant was created which is knocked out in sophorolipid production but instead produces MCL-PHA up to 0.99 wt/dwt when grown on glucose with addition of rapeseed oil.

Example 4.3

Production of Glycolipids

Example 4.3.1

Glucolipids

Figure 20:
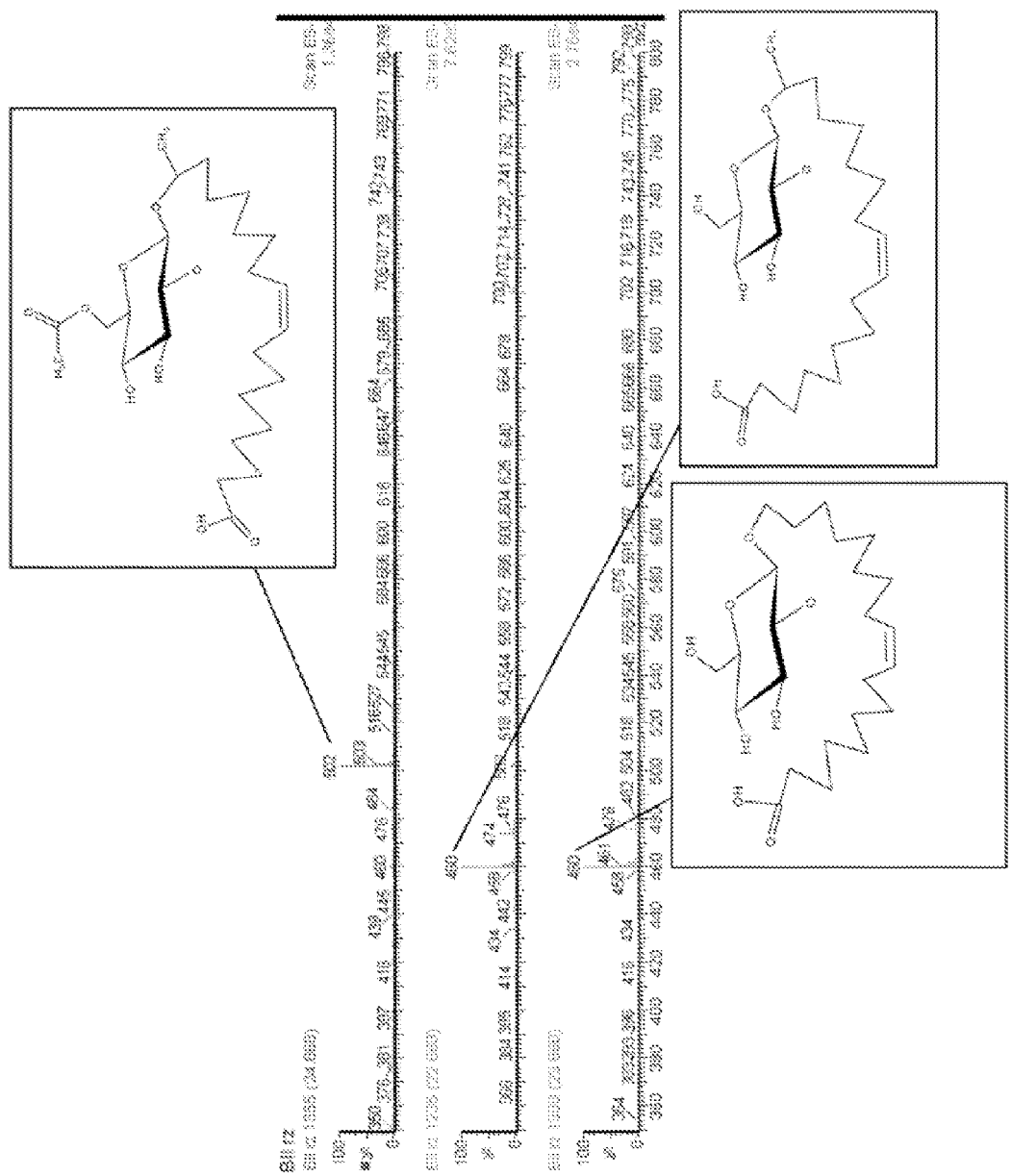

Due to the free carboxyl group, an unsaturated carbon chain and the presence of a carbohydrate head group, glucolipids are interesting intermediates for several kinds of biocatalytic or chemical conversion reactions. Since small structural variations can have a significant influence on biological activity or physico-chemical properties of a glycolipid, enzymatic or chemo-enzymatic synthesis of sophorolipid derivatives has been subject of some research papers (Bisht et al., 1999; Carr and Bisht, 2003; Rau et al., 2001) and patent applications (WO2004/044216 and US05/0164955). To date, glucolipids with a free carboxylic end are only produced by enzymatic conversion of acidic (open-ring) sophorolipids which are on their turn obtained after alkaline hydrolysis of the crude C. bombicola bioproduct (Rau et al., 1999; Saerens et al., 2009). On the other hand, alkyl glucosides could be obtained by microbial conversion of secondary alcohols (Brakemeier et al., 1998) or branched fatty alcohols (Palme et al., 2010). Acidic glucolipids (and sophorolipids) especially attract attention because they are asymmetrical bolaamphiphiles that, in addition to the supramolecular structures they typically form, also have increased chemical versatility as compared to the chemically synthesized symmetrical ones (Zhou et al., 2004). The ΔugtB1 deletion mutant created in Example 3 is an interesting strain that now offers time-saving in vivo production of these biomolecules starting from cheap renewable substrates. When we repeated the flask fermentation with the B11 mutant but prolonged the incubation on rapeseed oil to 14 days, the produced glucolipids were identified to be a mixture of structurally related molecules as revealed by mass spectrometric analysis of culture extracts (see material and method section Example 3 and FIG. 20). In addition to the most predominant mono-acetylated acidic glucolipids (m/z=502), minor amounts of unacetylated (sub-) terminally hydroxylated glucolipids could be identified (m/z=460) (FIG. 20). So far, no lactonization of glucolipids was observed. The appearance of acetylated glucolipids illustrates that the acetyltransferase, which normally decorates de novo sophorolipids at their 6' and/or 6" positions with acetyl-groups, shows activity towards glucolipids as well. In this respect it is possible that acetylation of glucolipids occurs before addition of the second glucosyl unit during de novo sophorolipid synthesis without being necessary for this second glucosylation reaction.

After 14 days incubation on rapeseed oil, residual oil still floats on top of the B11 culture while a wildtype fermentation after this time completely utilized rapeseed oil for sophorolipid production with a common yield around 50 g/L, indicating less efficient substrate conversion to glucolipids as compared to sophorolipids.

The production of glucolipids by the ΔugtB1 deletion mutant now creates a time efficient in vivo production process of these interesting glycolipid intermediates and this by conventional fermentation on cheap substrates.

Example 4.3.2

Cellobioselipids

Introduction

Cellobioselipids are produced in nature by several yeasts such as Cryptococcus (Puchkov et al., 2002), Pseudozyma (Kulakovskaya et al. 2005) and Sympodiomycopsis (Kulakovskaya et al., 2004), and the dimorphic fungus Ustilago maydis (Spoeckner et al., 1999, Teichmann et al., 2007). Their overall structure is comparable to sophorolipids, however the two glucose units are linked by a β-1,4 linkage, the fatty acid tail can show multiple hydroxylations (α-, ω- and ω-1) and the cellobiose molecule is acetylated and/or acylated with short chain (C6/C8) β-hydroxy fatty acids. Though cellobioselipids are promising antimicrobial agents, there is to date no industrial production due to the overall very low yields. We here create a C. bombicola mutant producing cellobioselipids instead of sophorolipids by changing the wildtype UGTB1 gene (see example 3) by either U. maydis UGT1 or Clostridium stercorarium CepB gene (Reichenbecher et al., 1997). The Ugt1 glucosyltransferase from U. maydis acts in a very comparable way to the UgtB1 glucosyltransferase from C. bombicola, using the same UDP-glucose as a glucosyl donor and a comparable glucolipid as an acceptor, linking both by a β-1,4 linkage instead of the β-1,2 formed by the UgtB1 glucosyltransferase (Teichmann et al., 2007). The bidirectional cellodextrin phosphorylase (CepB) from the cellulolytic thermophile bacterium Clostridium stercorarium is involved in cellulose degradation but the synthetic direction of the enzyme can use (17-O-β-D-glucopyranosyl)-octadecenoic acid obtained from C. bombicola sophorolipids (Saerens et al., 2009) as an acceptor for cellobioselipid formation, using glucose-1-Pi as a glucosyl donor.

Materials and Methods

Strains and Plasmids

C. bombicola G9 (derived from ATCC 22214, see Van Bogaert et al., 2008) was used for creation of the cellobioselipid producing mutant. Yeast cells were grown on YPD medium containing 1% yeast extract, 2% peptone and 2% dextrose, SD medium containing 0.67% yeast nitrogen base without amino acids (Difco) and 2% glucose or 3C medium containing 10% glucose, 1% yeast extract and 0.1% urea. Liquid media were incubated at 30° C. and 200 rpm. *E. coli* was grown on Luria Bertani medium (0.5% Bacto yeast extract, 1% Bacto Trypton, 0.5% NaCl) containing 0.01% ampicillin and incubated at 37° C. and 200 rpm. Plasmids were isolated from *E. coli* by means of the MiniPrep Plasmid Isolation kit from Qiagen and sequenced at LGC genomics (Germany).

Creation of the UGT1 and CepB Expression Cassettes

Both UGT1 and CepB expression cassettes were created by restriction enzyme mediated coupling of the wildtype *C. bombicola* UGTB1 promotor and a suitable terminator to the UGT1 and CepB genes respectively, followed by coupling of the promoter-gene-terminator sequence to the URA3 selectable marker. As a terminator, both the wildtype *C. bombicola* UGTB1 terminator as well as the tyrosine kinase (TK) terminator were used. All PCR reactions were performed with the PfuUltra High Fidelity PCR system (Stratagene) unless stated otherwise. As a first step, the UGTB1 promotor (P) in front of the UGT1 or CepB gene was amplified from plasmids pG_PUgt1T and PG_PCepBT respectively, pGEM_T® derived plasmids harboring the gene of interest in between the native UGTB1 promoter and terminator sequences. Primer pairs were MDR505Rev and Ugt1 1737Rev_SalI for the 2736 bp PUgt1 fragment and MDR505Rev and CepB 2355Rev_SalI for the 3354 bp PCepB fragment (Table 9). The 134 bp TK terminator was amplified from a plasmid containing the hygromycin resistance marker in between tyrosine kinase (TK) terminator and *C. bombicola* GAPD promoter (Van Bogaert et al., 2008) making use of primers TK F_SalI and TK R_MluI (Table 9). All obtained fragments were purified by means of the Qiaquick PCR purification kit (Qiagen) and subjected to an overnight SalI digest (New England Biolabs) according to Sambrook (Sambrook and Russell, 2001) but with a secondary addition of 20U restriction enzyme after 2 hours of incubation. After purification of the digested fragments by means of the MinElute reaction clean-up kit from Qiagen, both PCepB and PUgt1 fragments were ligated to the digested TK terminator. For that, 2U T4 DNA ligase from fermentas was added to 100 ng of the PCepB and PUgt1 fragments and a suitable amount of purified TK fragment was added such that a gene:terminator ratio of 3:1 was obtained. The mixture was incubated overnight at 22° C. Subsequently, the ligation products were amplified from the reaction mixtures by means of primers MDR505Rev and TKR_MluI yielding the 2856 bp PUgt1TK and 3474 bp PCepBTK fragment respectively. After purification, the fragments were cloned into the pJET1.2/blunt Cloning Vector using the CloneJet™ PCR Cloning kit from Fermentas and resulting plasmids pJ_PUgt1TK and pJ_PCepBTK were used for transformation of *E. coli* Fusion Blue and XL10Gold competent cells respectively, according to Sambrook (Sambrook and Russell, 2001). Correct transformants were identified by colony PCR and the derived plasmids were sent for sequencing. To couple the URA3 selectable marker, the inserts of plasmids pJ_PUgt1TK and pJ_PCepBTK were amplified again by means of the primers MDR505Rev and TKR_MluI, purified and subjected to an overnight MluI digest (New England Biolabs) according to Sambrook (Sambrook and Russell, 2001) but with a secondary addition of 20U restriction enzyme after 2 hours incubation. Accordingly, the URA3 selectable marker in addition to the *C. bombicola* UGTB1 3' end was amplified from plasmid pG_K-OugtB1 (see Example 3) by means of primers URA3 677F_MluI (Table 9) and GTII +239Rev (Table 4), purified and subjected to the same overnight MluI digest. After purification of the digested PUgt1TK, PCepBTK and URA3GT2T fragments, the genes of interest were coupled to the selection marker. For that, 100 ng of the PUgt1TK and PCepBTK fragment respectively was added to an appropriate amount of URA3GT2T fragment such that a gene:marker ratio of 3:1 was obtained and ligation was performed overnight at 22° C. with 2U of T4 DNA ligase (Fermentas). The final ligation products PUgt1TK_URA3GT2T (5856 bp) and PCepBTK_URA3GT2T (6474 bp) were amplified from the ligation mixtures by means of the Expand Long Template PCR System from Roche and primers MDR505Rev and GTII +239 Rev.

Alternatively, to create expression cassettes were the gene of interest is followed by the native *C. bombicola* UGTB1 terminator instead of the TK terminator, the complete inserts of plasmids pG_PUgt1T and PG_PCepBT were amplified by means of primer pair MDR505Rev/PCepBT214 R_MluI yielding the 2967 bp PUgt1T and the 3595 bp PCepBT fragments respectively. The URA3 selectable marker followed by the UGTB1 3' end but without terminator sequence, was amplified from plasmid pG_KOugtB1 with primers URA3677 F_MluI and GTII+1296Rev (Table 9). PCR products were purified, digested overnight with MluI and ligated as described above. Expression cassettes PUgt1T_URA3GT2 and PCepBT_URA3GT2 were amplified from the ligation mixtures by means of the Expand Long Template PCR System from Roche using primers MDR505Rev and GTII+1296Rev. All four obtained expression cassettes were gel purified using the Qiaquick Gelextraction kit from Qiagen and are cloned in pGEM-T® making use of the pGEM-T® Vector System (Promega). Plasmids are used for transformation of *E. coli* ultracompetent cells and correct transformants are identified by means of colony PCR. The derived plasmids are sent for sequencing.

Creation of the Cellobioselipid Producing Mutant

Linear expression cassettes PUgt1TK_URA3GT2T, PCepBTK_URA3GT2T, PUgt1T_URA3GT2 and PCepBT_URA3GT2 are amplified from the pGEM-T® derived plasmids making use of the primer MDR505Rev in combination with GTII +239Rev or GTII+1296Rev, depending of the presence or absence of the UGTB1 terminator at the 3' end of the cassette. The cassettes are purified and used for transformation of the ura3 deficient *C. bombicola* G9 strain by electroporation. For that, *C. bombicola* G9 is grown overnight in 100 mL YPD and when OD reaches 1, cells are harvested from 50 mL by centrifugation during 5 min at 4° C. and 4300 g. After washing twice with cold and sterile mQ water, cells are resuspended in 2 mL sterile sorbitol solution (1 M). After centrifugation at 4° C. and 4300 g, cells are resuspended in 2 mL sterile lithiumacetate (0.1 M) in presence of 2.5 mM DTT and left to rest at room temperature for 10 to 15 min. Cells are then harvested again and washed with 2 mL sorbitol (1M) before resuspending in 250 µl sorbitol (1M). From this suspension, 50 µl is carried over into a sterile eppendorf tube, 500 ng-1 µg of the linear expression cassette is added and the mixture is incubated on ice for 2 min before transfer to a 2 mm electroporation cuvette. A pulse of 1.5 kV (200 Ohm) is given during 5 milliseconds and 1 mL of cold and sterile YPD is added immediately. The cells are incubated for 1 h at 30° C. and 200 rpm and harvested by centrifugation at room temperature during 5 min at 1500 g. Cells are then resuspended in 1 mL sorbitol (1M) and aliquots of 200 µl are spread on selective SD plates. Plates are incubated at 30° C. until transformant colonies appear.

Characterization of Cellobioselipid Producing Mutants

Mutant colonies are first checked for correct integration of the expression cassette at the UGTB1 locus of the genome by means of yeast colony PCR. Correct transformants, appearing from double cross-over events, are transferred to 3C medium containing 10% glucose, 1% yeast extract, 0.1% urea and 2% agarose before inoculation to liquid production medium described by Lang et al. (2000) in order to check for glycolipid production. Liquid media are incubated at 30° C. and 200 rpm for two days before addition of rapeseed oil (37.5 g/L). Wildtype *C. bombicola* ATCC 22214 serves as a reference. One week after addition of rapeseed oil, glycolipids are extracted from 1 ml culture samples by means of 400 µl ethylacetate in presence of 10 µl acetic acid. Ethylacetate fractions are analysed on HPLC-ELSD and LC-MS as described in example 3. To verify the molecular structure of the produced cellobioselipids, the extracts of the mutants are scanned for compounds with molecular mass in the range of 600-800 (m/z).

TABLE 1

Primers used for knocking-out the *C. bombicola* CYP52M1 gene. All primers were obtained from Sigma Genosys.

| Name | Feature | Sequence | Seq ID NO: |
|---|---|---|---|
| A21TotFor | cloning CYP52M1 | CTGAGTGATAGGTTGAGCATTAG | 5 |
| A21TotRev | cloning CYP52M1 | GCTCTTGTTCGGTACTCTTATTG | 6 |
| GH1nfA21For | ligating selection marker into CYP52M1 | GCTAAAGTTACCCGA-CCAATGGCAGTGGCTTACCACTC | 7 |
| Hygro1nfA21Rev | ligating selection marker into CYP52M1 | GATCCTTCTGCTCGG-CCCGCGTTTATGAACAAACGACCC | 8 |
| A21KnockHygroCasFor | amplification knock-out fragment | GAGTCGGGCGTTATTTCTCC | 9 |
| A21KnockHygroCasRev | amplification knock-out fragment | AATCCCATAAACGACTACTC | 10 |
| HygroInsertCheckFor | checking knock-out genotype | TTCGACAGCGTCTCCGACCT | 11 |
| Ura3outEndfor | checking Cm2 genotype | TAAAGAAACGAAGGGCCCAGCAGTC | 12 |
| ATqRev | checking Cm2 genotype | CACCACAGTACGAGGAGGAACA | 13 |

TABLE 2

Primers used for isolation of the UGTA1 gene and construction of the knock-out cassette. All primers were obtained from Sigma Genosys.

| Name | Feature | Sequence | Seq ID No. |
|---|---|---|---|
| UDPGTA1 DS GSP1 | 3' primary GSP primer | 5' CAGCAGAGACCATCTGCCTACAACTTC 3' | 14 |
| UDPGTA1 DS GSP2 | 3' nested GSP primer | 5' CAACGCCCAAGCACCGAACTCAATTCAC 3' | 15 |
| UDPGTA1 TotF | High fidelity forward primer | 5' GAAGATACGTCCGTGCTTTG 3' | 16 |
| A1P RevNheI | High fidelity reverse primer | 5' CATGGCTAGCCGGGCATTATATGGCCTG 3' | 17 |
| A1T ForNheI | High fidelity forward primer | 5' CATGGCTAGCCGCTATGAACCACGCTCTTG 3' | 18 |
| A1T Rev | High fidelity reverse primer | 5' CATGACAGCCTTTTCTTCTT 3' | 19 |
| Ura3 FbisNheI | High fidelity forward primer | 5' CATGGCTAGCCTGACGGGCGGATAGTACAG 3' | 20 |

TABLE 2-continued

Primers used for isolation of the UGTA1 gene and construction of the knock-out cassette. All primers were obtained from Sigma Genosys.

| Name | Feature | Sequence | Seq ID No. |
|---|---|---|---|
| Ura3 RbisNheI | High fidelity reverse primer | 5' CATGGCTAGCGTCATCAACTCCATGGCGTGAGG 3' | 21 |

TABLE 3

Ten best homology scores for the translated UGTA1 sequence

| Gene | Organism | NCBI Acc. N° | % Id | E-score |
|---|---|---|---|---|
| Glycosyltransferase family protein | Mycobacterium vanbaalenii | YP_954817 | 35 | 8e-55 |
| UDP-glucuronosyl/glucosyltransferase | Mycobacterium radiotolerans | YP_001754776 | 35 | 2e-54 |
| Glycosyltransferase family protein | Mycobacterium gilvum | YP_001133857 | 33 | 2e-53 |
| Glycosyltransferase MGT family | Mycobacterium sp. | YP_640736 | 32 | 2e-52 |
| Glycosyltransferase MGT family | Mycobacterium sp. | YP_001071846 | 32 | 3e-52 |
| UDP-glucuronosyl/glucosyltransferase | Mycobacterium vanbaalenii | YP_955665 | 34 | 4e-52 |
| UDP-glucuronosyl/glucosyltransferase | Acidovorax avenae | YP_972968 | 31 | 3e-50 |
| UDP-glucuronosyl/glucosyltransferase | Burkholderia ambifaria | YP7_78119 | 31 | 3e-47 |
| UDP-glucuronosyl/glucosyltransferase | Methylocella silverstris | YP_002364149 | 31 | 1e-46 |
| UDP-glucuronosyl/glucosyltransferase | Mycobacterium gilvum | YP_001133117 | 32 | 2 |

TABLE 5

Ten best homology scores for the translated UGTB1 sequence

| Gene | Organism | NCBI Acc. N° | % Id | E-score |
|---|---|---|---|---|
| UDP-glucuronosyl/glucosyltransferase | Mycobacterium radiotolerans | YP_001754776 | 32 | 1e-15 |
| UDP-glucuronosyl/glucosyltransferase | Burkholderia ambifaria | YP_778119 | 31 | 5e-15 |
| Glycosyltransferase family protein | Mycobacterium vanbaalenii | YP_954817 | 32 | 2e-14 |
| UDP-glucuronosyl/glucosyltransferase | Acidovorax avenae | YP_972968 | 28 | 1e-13 |
| UDP-glucuronosyl/glucosyltransferase | Methylocella silverstris | YP_002364149 | 28 | 2e-13 |
| Glycosyltransferase MGT family | Pectobacterium wasabiae | YP_003258 26 | 29 | 1e-12 |
| Glycosyltransferase family protein | Mycobacterium gilvum | YP_001133857 | 31 | 2e-11 |
| Glycosyltransferase family 28 | Methylobacterium nodulans | YP_002500506 | 28 | 1e-10 |
| Glycosyltransferase MGT family | Pectobacterium carotovorum | YP_003018782 | 28 | 2e-10 |
| Glycosyltransferase MGT family | Mycobacterium sp. | YP_001071846 | 26 | 7e-10 |

TABLE 4

Primers used for isolation of the UGTB1 gene and construction of the knock-out cassette. All primers were obtained from Sigma Genosys.

| Name | Feature | Sequence | Seq ID No. |
|---|---|---|---|
| GTII-472For | High Fidelity forward primer | 5' GAGAGTGGGACCTGATTC 3' | 22 |
| GTII+239Rev | High Fidelity reverse primer | 5' CTGCTCTCAACACCGAGTGTAG 3' | 23 |
| Ura3inf ugtB1 F | High Fidelity forward primer | 5' AAGCAGAGAAGGCGCGATAGTACAGGCTTTGCC 3' | 24 |
| Ura3inf ugtB1 R | High Fidelity reverse primer | 5' CCTTCGTGGCCCCGATCATCGTCACTATACACATCG 3' | 25 |
| KOugtB1 Ctrl F | Control forward primer | 5' AAGCCAAAATCAGAGAGTG 3' | 26 |
| KOugtB1 Ctrl R | Control reverse primer | 5' GGTTCTGCGAAACTGGTATG 3' | 27 |

TABLE 6

Primers used for creating pGEM-T_cassette_yEGFP.

| Name | Feature | Sequence | Seq ID No. |
|---|---|---|---|
| P1_FOR_URA3v | Pick up ura3 gene +5' UTR | AGAACAAGGCCGAGTATGTC | |
| P2_REV_URA3v | Pick up ura3 gene +3' UTR | TGCCAGCAGATCATCATCAC | 29 |
| P3_FOR_URA3t_extyEGFP | Overlap primer ura3-yEGFP | GGATCCCCGCAGGGCATGCAACTTGCACATGAATACC | 30 |
| P4_REV_URA3t_extNOTI | Amplification ura3-yEGFP | TAGCGGCCGCGTCAGATTAGCCTCCGACATAG | 31 |
| P5_FOR_yEGFP_extMCS3 | Amplification ura3-yEGFP | GCACTAGTATACCCGGGCGCCT-CAGCTCTTCGATGTCTAAAGGTGAAGAAT | 32 |
| P6_REV_yEGFP_extURA3t | Overlap primer ura3-yEGFP | TATTCATGTGCAAGTTGCATGCCCTGCGGGGATCCATACG | 33 |
| P7_FOR_QCSaplpGEM-t | Mutagenesis primer ACTC | CGTATTGGGCGCTCCTCCGCTTCCTCGCTCACTG | 34 |
| P8_REV_QCSaplpGEM-t | Mutagenesis primer | GAGTCAGTGAGCGAGGAAGCGGAGGAGCGCCCAATACG | 35 |
| P18_REV_GAPDprom | Pick up pGAPD | TTCACCTTTAGACATTTGTGTAGAGTTGTTTTG | 36 |
| P19_FOR_pGAPD1560 | Pick up pGAPD | CACTAGTATACCCGGGACATCCGATGTGTAGTTA | 37 |
| P37_FOR_checkGFP | Colony PCR primer | GGTTGAATTAGATGGTGATGTTAATG | 38 |
| P35_REV_checkcasIN | Colony PCR primer | GAGCTCAAGACGCGTTTACTCAATGC | 39 |
| P31_REV_cassette | Amplification cassette | GCGTCAGATTAGCCTCCGACATAG | 40 |

Bold characters represent non-binding extensions.

TABLE 7

Primers used for creating the amylase expression cassette and control of amylase transformants.

| Name | Feature | Sequence | Seq ID No. |
|---|---|---|---|
| sAmyAOfw | Control cassette construction | GGTAGCAGCGTTGATTACTC | 41 |
| sAmyAOrv | Control cassette construction | ATCTGTGCCCTTACGCATAG | 42 |
| sAmyAOfw | checking amy coding region integrity | GGTAGCAGCGTTGATTACTC | 43 |
| sAmyAOrv | checking amy coding region integrity | ATCTGTGCCCTTACGCATAG | 44 |
| sAmyAOfw2 | checking integration cassette | CCGACAGCGAGCTGTACAAG | 45 |
| P35 | checking integration cassette | GAGCTCAAGACGCGTTTACT-CAATGC | 46 |

TABLE 8

Primers used for creating the PHA expression cassette. All primers were obtained from Sigma Genosys.

| Name | Feature | Sequence | Seq ID No. |
|---|---|---|---|
| P53_FOR_downCYP_extSpeI2 | cloning downstream region cyp52M1 | TTACTAGTGTTTCTTAGCCTCCCATG GAAGAAACG | 47 |
| P54_REV_downCYP_extNotI2 | cloning downstream region cyp52M1 | AATTGGCCTTGCGGCCGCGGTGTC GACTCGCCAAATTCCATC | 48 |
| P55_FOR_upCYP_extNheI | Amplification synthetic construct | GTTGCTAGCTCTCGGCAGATTTCCT TG | 49 |
| P58_REV_PHAC1 + tCYP_ext-EcoRI | amplification synthetic construct | AGAATTCGTCGGTTAAACGCACTCC TTCA | 50 |
| P63_FOR_cassPHAC1 | amplification PHA expression cassette | CTCTCGGCAGATTTCCTTGTG | 51 |
| P64_REV_cassPHAC1 | Amplification PHA expression cassette | GGTGTCGACTCGCCAAATTC | 52 |
| P9_FOR_seqQCSapI_URA3down | checking integration cassette | GCACACTTCAACCTTCCTAC | 53 |
| A21TotRev | checking integration cassette | GCTCTTGTTCGGTACTCTTATTG | 54 |
| UDPGTA1R | Sequencing primer | CCTACCTCTCTTCCCTGATCT | 55 |

TABLE 9

Primers used for creation of the UGT1 and CepB expression cassettes. All primers were obtained from Sigma Genosys

| Name | Feature | Sequence | Seq ID No. |
|---|---|---|---|
| MDR 505Rev | High fidelity forward primer | 5' CCTCGCCACCACCTAGTTTG 3' | 56 |
| Ugt1 1737Rev_SalI | High fidelity reverse primer | 5' GATCGTCGACTCAAAAGAGGCGGACTTCTGCC 3' | 57 |
| CepB 2355Rev_SalI | High fidelity reverse primer | 5' GATCGTCGACTCATCCCATTATAACAACAC 3' | 58 |
| TK F_SalI | High fidelity forward primer | 5' AATTGTCGACGGGAGATGGGGGAGGCTAAC 3' | 59 |
| TK R_SalI | High fidelity reverse primer | 5' GAGTACGCGTTGAACAAACGACCCAACACC 3' | 60 |
| URA3 677F_MluI | High fidelity forward primer | 5' GAGAACGCGTGATAGTACAGGCTTTGC 3' | 61 |
| PCepBT214 R_MluI | High fidelity reverse primer | 5' CATAACGCGTTTCTGCTCTCAACACCGAG 3' | 62 |

TABLE 9-continued

Primers used for creation of the UGT1 and CepB expression cassettes.
All primers were obtained from Sigma Genosys

| Name | Feature | Sequence | Seq ID No. |
|---|---|---|---|
| GTII +1296Rev | High fidelity reverse primer | 5' AGAAGCTAATTCACTAATTGCCGAC 3' | 63 |

REFERENCES

Asmer H. J., Lang S., Wagner F., Wray V. (1988). Microbial-Production, Structure Elucidation and Bioconversion of Sophorose Lipids. J. Am. Oil Chem. Soc., 65: p. 1460-1466.

Basehoar A. D., Zanton S. J., Pugh F. (2004). Identification and Distinct Regulation of Yeast TATA Box-Containg Genes. Cell, 116: p. 699-709.

Bisht K. S., Gross R. A., Kaplan D. L. (1999). Enzyme-mediated regioselective acylations of sophorolipids. J. Org. Chem., 64: p. 780-789.

Brakemeier A., Wullbrandt D., Lang S. (1998). Candida bombicola: production of novel alkyl glycosides based on glucose/2-dodecanol. Appl. Microbiol. Biotechnol., 50: p. 161-166.

Breithaupt T. B., Light R. J. (1982). Affinity chromatography and further characterization of the glucosyltrnasferases involved in hydroxydocosanoic acid sophoroside production in Candida bogoriensis. J. Biol. Chem., 257: p. 9622-9628.

Bucholtz, M. L., Light R. J. (1976). Acetylation of 13-sophorosyloxydocosanoic Acid by an Acetyltransferase Purified from Candida bogoriensis. J. Biol. Chem., 251: p. 424-430.

Campbell J. A., Davies G. J., Vulone V., Henrissat B. (1997). A classification of nucleotide-diphospho-sugar glycosyltransferases based on amino acid sequence similarities. Biochem. J, 326: p. 929-942.

Carr J. A., Bisht K. S. (2003). Enzyme-catalyzed regioselective transesterification of peracylated sophorolipids. Tetrahedron, 59: p. 7713-7724.

Casas J. A., Garcia-Ochoa F. (1999). Sophorolipid production by Candida bombicola: Medium composition and culture methods. J. Biosci. Bioeng., 88: p. 488-494.

Cavalero D. A., Cooper D. G. (2003). The effect of medium composition on the structure and physical state of sophorolipids produced by Candida bombicola ATCC 22214. J. Biotechnol., 103: p. 31-41.

Chen J., Song X., Zhang H., Qu Y. B., Miao J. Y. (2006). Production, structure elucidation and anticancer properties of sophorolipid from Wickerhamiella domercqiae. Enzyme Microb. Technol., 39: p. 501-506.

Cormack B. P., Bertram G., Egerton M., Gow N. A., Falkow S., Brown A. J. (1997a). Yeast-enhanced green fluorescent protein (yEGFP): A reporter of gene expression in Candida albicans. Microbiol-UK, 143: p. 303-311.

Coutinho P. M., Deleury E., Davies G. J., Henrissat B. (2003). An evolving hierarchical family classification for glycosyltransferases. J. Mol. Biol., 328: p. 307-317.

Daniel H. J., Otto R. T., Reuss M., Syldatk C. (1998a). Sophorolipid production with high yields on whey concentrate and rapeseed oil without consumption of lactose. Biotechnol. Lett, 20: p. 805-807.

Daniel H. J., Reuss M., Syldatk C. (1998b). Production of sophorolipids in high concentration from deproteinized whey and rapeseed oil in a two stage fed batch process using Candida bombicola ATCC 22214 and Cryptococcus curvatus ATCC 20509. Biotechnol. Lett, 20: p. 1153-1156.

Davila A. M., Marchal R., Vandecasteele J. P. (1992). Kinetics and balance of a fermentation free from product inhibition-sophorose lipid production by Candida bombicola. Appl. Microbiol. Biotechnol., 38: p. 6-11.

De Maeseneire S. L., De Groeve M. R. M., Dauvrin T., De Mey M., Soetaert W. K., Vandamme E. J. (2006). Cloning, sequence analysis and heterologous expression of the Myrothecium gramineum orotidine-5'-phosphate decarboxylase gene. FEMS Microbiol. Lett. 261: p. 262-271.

Esders T. W., Light R. J. (1972). Glucosyl- and acetyltransferases involved in the biosynthesis of glycolipids from Candida bogoriensis. J. Biol. Chem., 247: p. 1375-1386.

Gietz R. D., Schiestl R. H. (1995). Transforming yeast with DNA. Methods Mol. Cell Biol., 5: p. 255-269.

Gorin P. A. J., Spencer J. F. T., Tulloch A. P. (1961). Hydroxy fatty acid glycosides of sophorose from Torulopsis magnoliae. Can. J. Chem., 39: p. 846-855.

Gross R., Shah V. (2004). Antimicrobial properties of various forms of sophorolipids. International Patent WO 2004/044216 A1.

Gross R., Shah V. (2005). Antifungal properties of various forms of sophorolipids US Patent US 2005/0164955 A1.

Guo Z., Sherman F. (1996). Signals sufficient for 3'-End Formation of Yeast mRNA. Mol. Cell. Biol., 16: p. 2772-2776.

Hall T. A. (1999). BioEdit: a user-friendly biological sequence alignment editor and analysis program for windows 95/98/NT. Nucl. Acids. Symp. Ser. 41: p. 95-98.

Hewald S., Josephs K., Balker M. (2005). Genetic Analysis of Biosurfactant Production in Ustilago maydis. Appl. Environ. Microbiol., 71: p. 3033-3040.

Hewald S., Linne U., Scherer M., Marahiel M. A., Kamper J., Balker M. (2006). Identification of a Gene Cluster for Biosynthesis of Mannosylerythritol Lipids in the Basidiomycetous Fungus Ustilago maydis. Appl. Environ. Microbiol., 72: p. 5469-5477.

Hu Y., Ju L. K. (2003). Lipase-mediated deacetylation and oligomerization of lactonic sophorolipids. Biotechnol. Progr., 19: p. 303-311.

Imura T., Masuda Y., Minamikawa H., Fukuoka T., Konishi M., Morita T., Sakai H., Abe M., Kitamoto D. (2010). Enzymatic Conversion of Diacetylated Sophoroselipid into Acetylated Glucoselipid: Surface-Active Properties of Novel Bolaform Biosurfactants. J Oleo Sci. 59: p. 495-501.

Inoue S., Ito S. (1982). Sophorolipids from Torulopsis bombicola as microbial surfactants in alkane fermentations. Biotechnol. Lett, 4: p. 3-8.

Ito S., Inoue S. (1982). Sophorolipids from Torulopsis bombicola—Possible relation to alkane uptake. Appl. Environ. Microbiol., 43: p. 1278-1283.

Kim Y-B, Yun H. S., Kim E-K (2009). Enhanced sophorolipid production by feeding-rate-controlled fed-batch culture. Bioresour. Technol., 100: p. 6028-6032.

Kulakovskaya T. V., Shashkov A. S., Kulakovskaya E. V., Golubev W. I. (2004). Characterisation of an antifungal glycolipid secreted by the yeast *Sympodiomycopsis paphiopedili*. FEMS Yeast Res., 5: p. 247-252.

Kulakovskaya T. V., Shashkov A. S., Kulakovskaya E. V., Golubev, W. I. (2005). Ustilagoc acid secretion by *Pseudozyma fusiformata* strains. FEMS Yeast Res., 5: p. 919-923.

Kurtzman C. P., Price N. P. J., Ray K. J., Kuo T. M. (2010) Production of sophorolipid biosurfactants by multiple species of the *Starmerella (Candida) bombicola* yeast clade. FEMS Microbiol. Lett., 311: p. 140-146.

Lang S., Brakemeier A., Heckmann R., Spockner S., Rau U. (2000). Production of native and modified sophorose lipids. Chim Oggi-Chem Today, 18: p. 76-79.

Marchler-Bauer A. et al. (2009). CDD: Specific functional annotation with the Conserved Domain Database. Nucleic Acids Res., 37 (D): p. 205-210.

Marzluf G. A. (1997). Genetic Regulation of Nitrogen Metabolism in the Fungi. Microbiol. Mol. Biol. Rev., 61: p. 17-32.

Magasanik B., Kaiser C. A. (2002). Nitrogen regulation in *Saccharomyces cerevisiae*. Gene, 290: p. 1-18.

Ochsner U. A., Fiechter A., Reiser J. (1994a). Isolation, characterization, and expression in *Escherichia coli* of the *Pseudomonas aeruginosa* rhlAB genes encoding a rhamnosyltransferase involved in rhamnolipid biosurfactant synthesis. J. Biol. Chem., 269(31): p. 19787-19795.

Ochsner U. A., Koch A. K., Fiechter A., Reiser J. (1994b). Isolation and characterisation of a regulatory gene affecting rhamnolipid biosurfactant synthesis in *Pseudomonas aeruginosa*. J. Bacterial., 176: p. 2044-2054.

Palme O., Comanescu G., Stoineva I., Radel S., Benes E., Develter D., Wray V., Lang S. (2010). Sophorolipids from *Candida bombicola*: Cell separation by ultrasonic particle manipulation. Eur. J. Lipid Sci. Technol., 112: p. 663-673.

Puchkov E. O., Zahringer U., Lindner B., Kulakovskaya T. V., Seydel U., Wiese A. (2002). The mycocidal, membrane-active complex of *Cryptococcus humicola* is a new type of cellobiose lipid with detergent features. Biochim. Biophys. Acta, 1558: p. 161-170.

Rau U., Heckmann R., Wray V., Lang, S. (1999). Enzymatic conversion of a sophorolipid into a glucose lipid. Biotechnol. Lett, 21: p. 973-977.

Rau U., Hammen S., Heckmann R., Wray V., Lang S. (2001). Sophorolipids: a source for novel compounds. Ind. Crop Prod., 13: p. 85-92.

Reichenbecher M., Lottspeich F., Bronnenmeier K. (1997). Purification and properties of a cellobiose phosphorylase (CepA) and a cellodextrin phosphorylase (CepB) from the cellulolytic thermophile *Clostridium stercorarium*. Eur. J. Biochem., 247: p. 262-267.

Rosa C., Lachance M. (1998). The yeast genus *Starmerella* gen. nov. and *Starmerella bombicola* sp. nov., the teleomorph of *Candida bombicola* (Spencer, Gorin & Tullock) Meyer & Yarrow. Int. J. Syst. Bacteriol., 48: p. 1413-1417.

Rosell C. M., Haros M., Escriva C., de Barber C. B. (2001) Experimental approach to optimize the use of α-amylases in breadmaking. J. Agric. Food Chem., 49: p. 2973-2977.

Roy I., Sastry M. S. R., Johri B. N., Gupta, M. N. (2000) Purification of alpha-amylase isoenzymes from *Scytalidium thermophilum* on a fluidized bed of alginate beads followed by concanavalin A-agarose column chromatography. Protein Expr. Purif. 20: p. 162-168.

Saerens K., Van Bogaert I., Soetaert W. (2009). Production of glucolipids and specialty fatty acids from sophorolipids by *Penicillium decumbens* naringinase: Optimization and kinetics. Biotechnol. J., 4: p. 517-524.

Sambrook J., Russell D. W. (2001). Molecular Cloning: A Laboratory Manual. 3rd ed. Cold Spring Harbour Laboratory Press, Cold Spring Harbour, New York.

Spencer J. F. T., Gorin P. A. J., Tulloch A. P. (1970). *Torulopsis bombicola* sp.n. Antonie Van Leeuwenhoek 36: p. 129-133.

Spoeckner S., Wray V., Nimtz M., Lang S. (1999). Glycolipids of the smut fungus *Ustilago maydis* from cultivation on renewable resources. Appl. Microbiol. Biotechnol., 51: p. 33-39.

Stothard P. (2000). The Sequence Manipulation Suite: JavaScript programs for analyzing and formatting protein and DNA sequences. Biotechniques, 28: p. 1102-1104.

Teichmann B., Linne U., Hewald S., Marahiel M. A., Balker M. (2007). A biosynthetic gene cluster for a secreted cellobiose lipid with antifungal activity from *Ustilago maydis*. Mol. Microbiol., 66: p. 525-533.

Thaniyavarn J., Chianguthai T., Sangvanich P., Roongsawang N., Washio K., Morikawa M., Thaniyavarn S. (2008). Production of sophorolipid biosurfactant by *Pichia anomala*. Biosci. Biotechnol. Biochem., 72: p. 2061-2068.

Tulloch A. P., Spencer J. F. T., Deinema M. H. (1968). A new hydroxy fatty acid sophoroside from *Candida bogoriensis*. Can. J. Chem., 46: p. 345-348.

Van Bogaert I. N. A., De Maeseneire S. L., De Schamphelaire W., Develter D., Soetaert W., Vandamme E. J. (2007). Cloning, characterization and functionality of the orotidine-5'-phosphate decarboxylase gene (URA3) of the glycolipid-producing yeast *Candida bombicola*. Yeast, 24: p. 201-208.

Van Bogaert I. N. A., De Maeseneire S. L., Develter D., Soetaert W., Vandamme E. J. (2008a). Cloning and characterisation of the glyceraldehyde 3-phosphate dehydrogenase gene of *Candida bombicola* and use of its promoter. J. Ind. Microbiol. Biotechnol., 35: p. 1085-1092.

Van Bogaert I. N. A., De Maeseneire S. L., Develter D., Soetaert W., Vandamme E. J. (2008b). Development of a transformation and selection system for the glycolipid producing yeast *Candida bombicola*. Yeast, 25: p. 272-278.

Van Bogaert I. N. A., De Mey M., Develter D., Soetaert W., Vandamme E. J. (2009). Importance of the cytochrome P450 monooxygenase CYP52 family for the sophorolipid-producing yeast *Candida bombicola*. FEMS Yeast Res., 9: p. 87-94.

Zhou S. Q., Xu C., Wang J., Gao W., Akhverdiyeva R., Shah V., Gross R. (2004). Supramolecular assemblies of a naturally derived sophorolipid. Langmuir, 20: p. 7926-7932.

SEQUENCE LISTING

<160> NUMBER OF SEQ ID NOS: 67

<210> SEQ ID NO 1
<211> LENGTH: 1778
<212> TYPE: DNA

<213> ORGANISM: Candida bombicola

<400> SEQUENCE: 1

| | |
|---|---|
| cagatatgca tcaggggcac agactaaaag ctgctctcag cgagtaccct tacctcttga | 60 |
| gaaccctcaa aatttaccca gcctgcagca tatcatgcac catggttaaa ttcggaaatg | 120 |
| aatttaccgg tggccttgaa ccacgttcct ccaattattt aaggcaataa cctgccactc | 180 |
| tcttgatttg attaagaaag actttcaatt tagcttctcc ctacgaatat tcaatgagcc | 240 |
| cttcatcaca caaaccctg attctcgctt gcggcttgcc tctttcaggc catataatgc | 300 |
| ccgttttgag tctggtacac ggccttacgg acgacggata cgaagctact gttgtgacag | 360 |
| gcagagcgtt tgaacaaaaa gttcgagatg tgggtgcaga cttttgttcct ttagaaggga | 420 |
| acgcagattt tgatgaccac accttagacg atctggtccc gggccgtaaa gacatggccc | 480 |
| caagcttcga tcgtacagtt caagatgtgg agcacatgat ggtagctact cttcctgagc | 540 |
| agtttgccgc tattcagagg gctttcaaaa agctcagcgc aagcggccgc cctgtcgttc | 600 |
| ttgtcagtga agtgctgttt ttcggtgcac acccctatcag cctcggtgct cctggtttca | 660 |
| aacccgctgg ctggatttgt ttaggggttt tgcctctttt gatccgcagt gatcatacct | 720 |
| taggacttga caacgacagg agccccgaag cacatgcaaa gaaactcgct atgaaccacg | 780 |
| ctcttgagca ccaaattttc gttaaagcca ctgctaagca aaggaaaatc tgccgagagt | 840 |
| taggttgcac tgaagatccc aaatttatct gggagcacag ttacattgct gcagacaagt | 900 |
| tcctgcagct gtgcccgcct tctcttgagt tcagcagaga ccatctgcct agcaacttca | 960 |
| aattcgccgg ctcaacgccc aagcaccgaa ctcaattcac ccctccttcc tggtgggggg | 1020 |
| atgttctgag tgccaagcga gtcatcatgg tcactcaagg aacttttgct gtcagttaca | 1080 |
| agcatcttat tgtgcctact cttgaggcct gaaggacga gcctgacact ttaacagtag | 1140 |
| ccatattggg ccgccgcggt gccaagctac cggatgatgt tgtggttcct gagaatgctc | 1200 |
| gcgtgatcga ctacttcaac tacgatgctc tacttcctca cgttgatgct cttgtctaca | 1260 |
| atggtggata tggcggactt cagcacagct taagccactc tgttccagtt gttattgctg | 1320 |
| gtgactctga agacaagcca atggtggcat cgagagctga ggccgctggc gtggcaattg | 1380 |
| atttgaaaac tggcttgcct acagtggagc aaatcaaaga agctgttgat tcgataattg | 1440 |
| gaaatccgaa attccacgaa gcctcgaaga aggttcaaat ggagttggaa agccacaact | 1500 |
| ccttgaaaat tcttgaggaa agcatcgagg aaatcgccag ccatgacttt ggtctttgta | 1560 |
| ccaagagtga cgaggaaact gaagatatac ctgtcaaagg gccggcctta gcggtgagtt | 1620 |
| cttagaatcg tacgatcaaa tcagatcagg gaagagaggt agggttttt ttatttatgt | 1680 |
| ctttgttttt attgattgaa atttacaata caacaaccat caaattaatt tgaacaaaca | 1740 |
| acaacacaca cacactgcaa ctttcaaaaa aataagta | 1778 |

<210> SEQ ID NO 2
<211> LENGTH: 463
<212> TYPE: PRT
<213> ORGANISM: Candida bombicola

<400> SEQUENCE: 2

Met Ser Pro Ser Ser His Lys Pro Leu Ile Leu Ala Cys Gly Leu Pro
1               5                   10                  15

Leu Ser Gly His Ile Met Pro Val Leu Ser Leu Val His Gly Leu Thr
            20                  25                  30

Asp Asp Gly Tyr Glu Ala Thr Val Val Thr Gly Arg Ala Phe Glu Gln

-continued

```
                35                  40                  45
Lys Val Arg Asp Val Gly Ala Asp Phe Val Pro Leu Glu Gly Asn Ala
 50                  55                  60

Asp Phe Asp Asp His Thr Leu Asp Asp Leu Val Pro Gly Arg Lys Asp
 65                  70                  75                  80

Met Ala Pro Ser Phe Asp Arg Thr Val Gln Asp Val Glu His Met Met
                 85                  90                  95

Val Ala Thr Leu Pro Glu Gln Phe Ala Ala Ile Gln Arg Ala Phe Lys
                100                 105                 110

Lys Leu Ser Ala Ser Gly Arg Pro Val Leu Val Ser Glu Val Leu
                115                 120                 125

Phe Phe Gly Ala His Pro Ile Ser Leu Gly Ala Pro Gly Phe Lys Pro
                130                 135                 140

Ala Gly Trp Ile Cys Leu Gly Val Leu Pro Leu Ile Arg Ser Asp
145                 150                 155                 160

His Thr Leu Gly Leu Asp Asn Asp Arg Ser Pro Glu Ala His Ala Lys
                165                 170                 175

Lys Leu Ala Met Asn His Ala Leu Glu His Gln Ile Phe Val Lys Ala
                180                 185                 190

Thr Ala Lys His Lys Glu Ile Cys Arg Glu Leu Gly Cys Thr Glu Asp
                195                 200                 205

Pro Lys Phe Ile Trp Glu His Ser Tyr Ile Ala Ala Asp Lys Phe Leu
                210                 215                 220

Gln Leu Cys Pro Pro Ser Leu Glu Phe Ser Arg Asp His Leu Pro Ser
225                 230                 235                 240

Asn Phe Lys Phe Ala Gly Ser Thr Pro Lys His Arg Thr Gln Phe Thr
                245                 250                 255

Pro Pro Ser Trp Trp Gly Asp Val Leu Ser Ala Lys Arg Val Ile Met
                260                 265                 270

Val Thr Gln Gly Thr Phe Ala Val Ser Tyr Lys His Leu Ile Val Pro
                275                 280                 285

Thr Leu Glu Ala Leu Lys Asp Glu Pro Asp Thr Leu Thr Val Ala Ile
                290                 295                 300

Leu Gly Arg Arg Gly Ala Lys Leu Pro Asp Asp Val Val Pro Glu
305                 310                 315                 320

Asn Ala Arg Val Ile Asp Tyr Phe Asn Tyr Asp Ala Leu Leu Pro His
                325                 330                 335

Val Asp Ala Leu Val Tyr Asn Gly Gly Tyr Gly Gly Leu Gln His Ser
                340                 345                 350

Leu Ser His Ser Val Pro Val Ile Ala Gly Asp Ser Glu Asp Lys
                355                 360                 365

Pro Met Val Ala Ser Arg Ala Glu Ala Ala Gly Val Ala Ile Asp Leu
                370                 375                 380

Lys Thr Gly Leu Pro Thr Val Glu Gln Ile Lys Glu Ala Val Asp Ser
385                 390                 395                 400

Ile Ile Gly Asn Pro Lys Phe His Glu Ala Lys Lys Val Gln Met
                405                 410                 415

Glu Leu Glu Ser His Asn Ser Leu Lys Ile Leu Glu Glu Ser Ile Glu
                420                 425                 430

Glu Ile Ala Ser His Asp Phe Gly Leu Leu Thr Lys Ser Asp Glu Glu
                435                 440                 445

Thr Glu Asp Ile Pro Val Lys Gly Pro Ala Leu Ala Val Ser Ser
450                 455                 460
```

<210> SEQ ID NO 3
<211> LENGTH: 2010
<212> TYPE: DNA
<213> ORGANISM: Candida bombicola

<400> SEQUENCE: 3

```
gagagtggga cctgattcag aatcacacgg acccgtatat ataacaatca ctttccaaca      60
atatagcgag tattaatata tttccgggta agggttgttc cggacttatg catttaatca     120
caggttgcat cagctaaata tgtcagggcc gacggcgtaa atttagaagg ttaggtcaag     180
atccatcggt caggccaatg gagctctact atgataggca gctgaagcga gacaagatat     240
acttcagttg cgctctctga aaaaattatt ttgtgattct cactcagtgg atgtggcgac     300
acacggaacc aataatctcg ccggaaaggc ggctgaacat cagtcttgca taagtgtgca     360
agtggcctga gcacagcgtg cattacccct accatacatt cggggcaagt aaatccagc     420
attatataaa cttgattgac acaaatgggc ataaaacaat aaagtctcct atatggccat     480
cgagaaacca gtgatagttg cttgtgcctg cccactagcg gggcacgtgg gcccagtgct     540
cagcctggtc cgcggtctac tcaatagagg atatgaggtg actttcgtaa cagggaacgc     600
attcaaggag aaagttattg aggcaggatg cactttcgtc cctctccaag gacgagctga     660
ctaccatgaa tacaatctcc ctgaaatcgc tccaggattg ctcacgattc ctccaggcct     720
tgagcagacc ggttactcaa tgaatgagat ttttgtgaag gcgattcctg agcagtacga     780
tgcacttcaa actgctctaa aacaggttga ggctgaaaat aaatcagctg tggtgattgg     840
cgagaccatg tttctagggg tgcatccgat atcactgggt gccccaggtc tcaagcccca     900
aggcgtaatc acgttaggaa ctattccgtg catgctgaaa gcagagaagg cgcctggagt     960
tcctagtctt gagccaatga ttgatacttt agtgcggcaa caagtatttc aaccaggaac    1020
tgactctgag aaggagatca tgaagacgct cggggccacg aaggagcccg aatttctcct    1080
ggagaatata tacagcagcc ctgacagatt tttgcaactg tgccctccat ctcttgaatt    1140
tcacttgact tcgcctcctc ctggcttctc gttcgctggt agtgcaccgc atgtaaagtc    1200
tgctggatta gcaactccac ctcacctgcc gtcttggtgg cctgatgtgc tgagtgcgaa    1260
gcgtctgatt gttgttacac aaggaacagc agccatcaac tatgaagatc tgctcattcc    1320
agcattgcag gcctttgctg acgaagaaga cactctcgta gttggtatat gggcgtcaa    1380
aggggcgtca cttcctgata gcgttaaagt tcctgcaaac gctcgaattg ttgattattt    1440
tccttacgat gagctactac cgcatgcctc tgttttcata taacaacggtg gatacggagg    1500
tctgcagcac agtttgagcc atggcgttcc cgtcatcatc ggaggaggaa tgttggtaga    1560
caagccagct gttgcttcac gagctgtatg ggctggtgtt ggttatgatc ttcaaacctt    1620
gcaggcaact tctgagctag tctccacggc cgttaaggag gtgttggcta ctccctcgta    1680
tcacgagaaa gccatggcag tcaagaaaga gcttgaaaaa tacaagtctc ttgatattct    1740
agagtcggca attagtgaat tagcttctta acctggctct ttttctagat atgtctgcgc    1800
cctgctcact gcttactggc ctaagctggt attacggacc ttaatcaagt atcaccccaa    1860
ggcaatcgag agtcttatcg agtctctagg tagatagata cacgttttga ttttcggcc    1920
cactttgtag aaaaatctca gtgatttcat ggaattcagt tacaaatact aatctgataa    1980
accaagaact acactcggtg ttgagagcag                                      2010
```

<210> SEQ ID NO 4

<211> LENGTH: 408
<212> TYPE: PRT
<213> ORGANISM: Candida bombicola

<400> SEQUENCE: 4

| Met | Ala | Ile | Glu | Lys | Pro | Val | Ile | Val | Ala | Cys | Ala | Cys | Pro | Leu | Ala |
|---|---|---|---|---|---|---|---|---|---|---|---|---|---|---|---|
| 1 | | | | 5 | | | | | 10 | | | | | 15 | |

Gly His Val Gly Pro Val Leu Ser Leu Val Arg Gly Leu Leu Asn Arg
            20                  25                  30

Gly Tyr Glu Val Thr Phe Val Thr Gly Asn Ala Phe Lys Glu Lys Val
        35                  40                  45

Ile Glu Ala Gly Cys Thr Phe Val Pro Leu Gln Gly Arg Ala Asp Tyr
 50                  55                  60

His Glu Tyr Asn Leu Pro Glu Ile Ala Pro Gly Leu Leu Thr Ile Pro
65                  70                  75                  80

Pro Gly Leu Glu Gln Thr Gly Tyr Ser Met Asn Glu Ile Phe Val Lys
                85                  90                  95

Ala Ile Pro Glu Gln Tyr Asp Ala Leu Gln Thr Ala Leu Lys Gln Val
            100                 105                 110

Glu Ala Glu Asn Lys Ser Ala Val Val Ile Gly Glu Thr Met Phe Leu
        115                 120                 125

Gly Val His Pro Ile Ser Leu Gly Ala Pro Gly Leu Lys Pro Gln Gly
130                 135                 140

Val Ile Thr Leu Gly Thr Ile Pro Cys Met Leu Lys Ala Glu Lys Ala
145                 150                 155                 160

Pro Gly Val Pro Ser Leu Glu Pro Met Ile Asp Thr Leu Val Arg Gln
                165                 170                 175

Gln Val Phe Gln Pro Gly Thr Asp Ser Glu Lys Glu Ile Met Lys Thr
            180                 185                 190

Leu Gly Ala Thr Lys Glu Pro Glu Phe Leu Leu Glu Asn Ile Tyr Ser
        195                 200                 205

Ser Pro Asp Arg Phe Leu Gln Leu Cys Pro Pro Ser Leu Glu Phe His
210                 215                 220

Leu Thr Ser Pro Pro Gly Phe Ser Phe Ala Gly Ser Ala Pro His
225                 230                 235                 240

Val Lys Ser Ala Gly Leu Ala Thr Pro Pro His Leu Pro Ser Trp Trp
                245                 250                 255

Pro Asp Val Leu Ser Ala Lys Arg Leu Ile Val Val Thr Gln Gly Thr
            260                 265                 270

Ala Ala Ile Asn Tyr Glu Asp Leu Leu Ile Pro Ala Leu Gln Ala Phe
        275                 280                 285

Ala Asp Glu Glu Asp Thr Leu Val Val Gly Ile Leu Gly Val Lys Gly
290                 295                 300

Ala Ser Leu Pro Asp Ser Val Lys Val Pro Ala Asn Ala Arg Ile Val
305                 310                 315                 320

Asp Tyr Phe Pro Tyr Asp Glu Leu Leu Pro His Ala Ser Val Phe Ile
                325                 330                 335

Tyr Asn Gly Gly Tyr Gly Gly Leu Gln His Ser Leu Ser His Gly Val
            340                 345                 350

Pro Val Ile Ile Gly Gly Met Leu Val Asp Lys Pro Ala Val Ala
        355                 360                 365

Ser Arg Ala Val Trp Ala Gly Val Gly Tyr Asp Leu Gln Thr Leu Gln
370                 375                 380

Ala Thr Ser Glu Leu Val Ser Thr Ala Val Lys Glu Val Leu Ala Thr

```
385             390             395             400
Pro Ser Ile Ser Glu Leu Ala Ser
                405
```

<210> SEQ ID NO 5
<211> LENGTH: 23
<212> TYPE: DNA
<213> ORGANISM: Artificial sequence
<220> FEATURE:
<223> OTHER INFORMATION: Primer

<400> SEQUENCE: 5
ctgagtgata ggttgagcat tag                                    23

<210> SEQ ID NO 6
<211> LENGTH: 23
<212> TYPE: DNA
<213> ORGANISM: Artificial sequence
<220> FEATURE:
<223> OTHER INFORMATION: Primer

<400> SEQUENCE: 6
gctcttgttc ggtactctta ttg                                    23

<210> SEQ ID NO 7
<211> LENGTH: 38
<212> TYPE: DNA
<213> ORGANISM: Artificial sequence
<220> FEATURE:
<223> OTHER INFORMATION: Primer

<400> SEQUENCE: 7
gctaaagtta cccgaccaat ggcagtggct taccactc                    38

<210> SEQ ID NO 8
<211> LENGTH: 39
<212> TYPE: DNA
<213> ORGANISM: Artificial sequence
<220> FEATURE:
<223> OTHER INFORMATION: Primer

<400> SEQUENCE: 8
gatccttctg ctcggcccgc gtttatgaac aaacgaccc                   39

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gagtcgggcg ttatttctcc                                        20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
aatcccataa acgactactc                                        20

<210> SEQ ID NO 11

```
<211> LENGTH: 20
<212> TYPE: DNA
<213> ORGANISM: Artificial sequence
<220> FEATURE:
<223> OTHER INFORMATION: Primer

<400> SEQUENCE: 11
ttcgacagcg tctccgacct                                                    20

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12
taaagaaacg aagggcccag cagtc                                              25

<210> SEQ ID NO 13
<211> LENGTH: 22
<212> TYPE: DNA
<213> ORGANISM: Artificial sequence
<220> FEATURE:
<223> OTHER INFORMATION: Primer

<400> SEQUENCE: 13
caccacagta cgaggaggaa ca                                                 22

<210> SEQ ID NO 14
<211> LENGTH: 27
<212> TYPE: DNA
<213> ORGANISM: Artificial sequence
<220> FEATURE:
<223> OTHER INFORMATION: Primer

<400> SEQUENCE: 14
cagcagagac catctgccta caacttc                                            27

<210> SEQ ID NO 15
<211> LENGTH: 28
<212> TYPE: DNA
<213> ORGANISM: Artificial sequence
<220> FEATURE:
<223> OTHER INFORMATION: Primer

<400> SEQUENCE: 15
caacgcccaa gcaccgaact caattcac                                           28

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
gaagatacgt ccgtgctttg                                                    20

<210> SEQ ID NO 17
<211> LENGTH: 28
<212> TYPE: DNA
<213> ORGANISM: Artificial sequence
<220> FEATURE:
<223> OTHER INFORMATION: Primer

<400> SEQUENCE: 17
```

-continued catggctagc cgggcattat atggcctg                                  28

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
catggctagc cgctatgaac cacgctcttg                                30

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
catgacagcc ttttcttctt                                           20

<210> SEQ ID NO 20
<211> LENGTH: 30
<212> TYPE: DNA
<213> ORGANISM: Artificial sequence
<220> FEATURE:
<223> OTHER INFORMATION: Primer

<400> SEQUENCE: 20
catggctagc ctgacgggcg gatagtacag                                30

<210> SEQ ID NO 21
<211> LENGTH: 33
<212> TYPE: DNA
<213> ORGANISM: Artificial sequence
<220> FEATURE:
<223> OTHER INFORMATION: Primer

<400> SEQUENCE: 21
catggctagc gtcatcaact ccatggcgtg agg                            33

<210> SEQ ID NO 22
<211> LENGTH: 18
<212> TYPE: DNA
<213> ORGANISM: Artificial sequence
<220> FEATURE:
<223> OTHER INFORMATION: Primer

<400> SEQUENCE: 22
gagagtggga cctgattc                                             18

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
ctgctctcaa caccgagtgt ag                                        22

<210> SEQ ID NO 24
<211> LENGTH: 33
<212> TYPE: DNA

```
<213> ORGANISM: Artificial sequence
<220> FEATURE:
<223> OTHER INFORMATION: Primer

<400> SEQUENCE: 24
aagcagagaa ggcgcgatag tacaggcttt gcc                                    33

<210> SEQ ID NO 25
<211> LENGTH: 36
<212> TYPE: DNA
<213> ORGANISM: Artificial sequence
<220> FEATURE:
<223> OTHER INFORMATION: Primer

<400> SEQUENCE: 25
ccttcgtggc cccgatcatc gtcactatac acatcg                                 36

<210> SEQ ID NO 26
<211> LENGTH: 19
<212> TYPE: DNA
<213> ORGANISM: Artificial sequence
<220> FEATURE:
<223> OTHER INFORMATION: Primer

<400> SEQUENCE: 26
aagccaaaat cagagagtg                                                    19

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
ggttctgcga aactggtatg                                                   20

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
agaacaaggc cgagtatgtc                                                   20

<210> SEQ ID NO 29
<211> LENGTH: 20
<212> TYPE: DNA
<213> ORGANISM: Artificial sequence
<220> FEATURE:
<223> OTHER INFORMATION: Primer

<400> SEQUENCE: 29
tgccagcaga tcatcatcac                                                   20

<210> SEQ ID NO 30
<211> LENGTH: 37
<212> TYPE: DNA
<213> ORGANISM: Artificial sequence
<220> FEATURE:
<223> OTHER INFORMATION: Primer

<400> SEQUENCE: 30
ggatccccgc agggcatgca acttgcacat gaatacc                                37
```

<210> SEQ ID NO 31
<211> LENGTH: 32
<212> TYPE: DNA
<213> ORGANISM: Artificial sequence
<220> FEATURE:
<223> OTHER INFORMATION: Primer

<400> SEQUENCE: 31
tagcggccgc gtcagattag cctccgacat ag                        32

<210> SEQ ID NO 32
<211> LENGTH: 51
<212> TYPE: DNA
<213> ORGANISM: Artificial sequence
<220> FEATURE:
<223> OTHER INFORMATION: Primer

<400> SEQUENCE: 32
gcactagtat acccgggcgc ctcagctctt cgatgtctaa aggtgaagaa t    51

<210> SEQ ID NO 33
<211> LENGTH: 40
<212> TYPE: DNA
<213> ORGANISM: Artificial sequence
<220> FEATURE:
<223> OTHER INFORMATION: Primer

<400> SEQUENCE: 33
tattcatgtg caagttgcat gccctgcggg gatccatacg                 40

<210> SEQ ID NO 34
<211> LENGTH: 38
<212> TYPE: DNA
<213> ORGANISM: Artificial sequence
<220> FEATURE:
<223> OTHER INFORMATION: Primer

<400> SEQUENCE: 34
cgtattgggc gctcctccgc ttcctcgctc actgactc                   38

<210> SEQ ID NO 35
<211> LENGTH: 38
<212> TYPE: DNA
<213> ORGANISM: Artificial sequence
<220> FEATURE:
<223> OTHER INFORMATION: Primer

<400> SEQUENCE: 35
gagtcagtga gcgaggaagc ggaggagcgc ccaatacg                   38

<210> SEQ ID NO 36
<211> LENGTH: 34
<212> TYPE: DNA
<213> ORGANISM: Artificial sequence
<220> FEATURE:
<223> OTHER INFORMATION: Primer

<400> SEQUENCE: 36 ttcacccttta gacatttgtg tagagttgtt tttg                      34

<210> SEQ ID NO 37
<211> LENGTH: 34
<212> TYPE: DNA
<213> ORGANISM: Artificial sequence
<220> FEATURE:

-continued

<223> OTHER INFORMATION: Primer

<400> SEQUENCE: 37
cactagtata cccgggacat ccgatgtgta gtta                                 34

<210> SEQ ID NO 38
<211> LENGTH: 26
<212> TYPE: DNA
<213> ORGANISM: Artificial sequence
<220> FEATURE:
<223> OTHER INFORMATION: Primer

<400> SEQUENCE: 38
ggttgaatta gatggtgatg ttaatg                                          26

<210> SEQ ID NO 39
<211> LENGTH: 26
<212> TYPE: DNA
<213> ORGANISM: Artificial sequence
<220> FEATURE:
<223> OTHER INFORMATION: Primer

<400> SEQUENCE: 39
gagctcaaga cgcgtttact caatgc                                          26

<210> SEQ ID NO 40
<211> LENGTH: 24
<212> TYPE: DNA
<213> ORGANISM: Artificial sequence
<220> FEATURE:
<223> OTHER INFORMATION: Primer

<400> SEQUENCE: 40
gcgtcagatt agcctccgac atag                                            24

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
ggtagcagcg ttgattactc                                                 20

<210> SEQ ID NO 42
<211> LENGTH: 20
<212> TYPE: DNA
<213> ORGANISM: Artificial sequence
<220> FEATURE:
<223> OTHER INFORMATION: Primer

<400> SEQUENCE: 42
atctgtgccc ttacgcatag                                                 20

<210> SEQ ID NO 43
<211> LENGTH: 20
<212> TYPE: DNA
<213> ORGANISM: Artificial sequence
<220> FEATURE:
<223> OTHER INFORMATION: Primer

<400> SEQUENCE: 43
ggtagcagcg ttgattactc                                                 20

```
<210> SEQ ID NO 44
<211> LENGTH: 20
<212> TYPE: DNA
<213> ORGANISM: Artificial sequence
<220> FEATURE:
<223> OTHER INFORMATION: Primer

<400> SEQUENCE: 44
atctgtgccc ttacgcatag                                              20

<210> SEQ ID NO 45
<211> LENGTH: 20
<212> TYPE: DNA
<213> ORGANISM: Artificial sequence
<220> FEATURE:
<223> OTHER INFORMATION: Primer

<400> SEQUENCE: 45
ccgacagcga gctgtacaag                                              20

<210> SEQ ID NO 46
<211> LENGTH: 20
<212> TYPE: DNA
<213> ORGANISM: Artificial sequence
<220> FEATURE:
<223> OTHER INFORMATION: Primer

<400> SEQUENCE: 46
ccgacagcga gctgtacaag                                              20

<210> SEQ ID NO 47
<211> LENGTH: 35
<212> TYPE: DNA
<213> ORGANISM: Artificial sequence
<220> FEATURE:
<223> OTHER INFORMATION: Primer

<400> SEQUENCE: 47
ttactagtgt ttcttagcct cccatggaag aaacg                             35

<210> SEQ ID NO 48
<211> LENGTH: 42
<212> TYPE: DNA
<213> ORGANISM: Artificial sequence
<220> FEATURE:
<223> OTHER INFORMATION: Primer

<400> SEQUENCE: 48
aattggcctt gcggccgcgg tgtcgactcg ccaaattcca tc                     42

<210> SEQ ID NO 49
<211> LENGTH: 27
<212> TYPE: DNA
<213> ORGANISM: Artificial sequence
<220> FEATURE:
<223> OTHER INFORMATION: Primer

<400> SEQUENCE: 49
gttgctagct ctcggcagat ttccttg                                      27

<210> SEQ ID NO 50
<211> LENGTH: 29
<212> TYPE: DNA
<213> ORGANISM: Artificial sequence
<220> FEATURE:
<223> OTHER INFORMATION: Primer
```

```
<400> SEQUENCE: 50
agaattcgtc ggttaaacgc actccttca                                    29

<210> SEQ ID NO 51
<211> LENGTH: 21
<212> TYPE: DNA
<213> ORGANISM: Artificial sequence
<220> FEATURE:
<223> OTHER INFORMATION: Primer

<400> SEQUENCE: 51
ctctcggcag atttccttgt g                                            21

<210> SEQ ID NO 52
<211> LENGTH: 20
<212> TYPE: DNA
<213> ORGANISM: Artificial sequence
<220> FEATURE:
<223> OTHER INFORMATION: Primer

<400> SEQUENCE: 52
ggtgtcgact cgccaaattc                                              20

<210> SEQ ID NO 53
<211> LENGTH: 20
<212> TYPE: DNA
<213> ORGANISM: Artificial sequence
<220> FEATURE:
<223> OTHER INFORMATION: Primer

<400> SEQUENCE: 53
gcacacttca accttcctac                                              20

<210> SEQ ID NO 54
<211> LENGTH: 23
<212> TYPE: DNA
<213> ORGANISM: Artificial sequence
<220> FEATURE:
<223> OTHER INFORMATION: Primer

<400> SEQUENCE: 54
gctcttgttc ggtactctta ttg                                          23

<210> SEQ ID NO 55
<211> LENGTH: 21
<212> TYPE: DNA
<213> ORGANISM: Artificial sequence
<220> FEATURE:
<223> OTHER INFORMATION: Primer

<400> SEQUENCE: 55
cctacctctc ttccctgatc t                                            21

<210> SEQ ID NO 56
<211> LENGTH: 20
<212> TYPE: DNA
<213> ORGANISM: Artificial sequence
<220> FEATURE:
<223> OTHER INFORMATION: Primer

<400> SEQUENCE: 56
cctcgccacc acctagtttg                                              20

<210> SEQ ID NO 57
<211> LENGTH: 32
```

<212> TYPE: DNA
<213> ORGANISM: Artificial sequence
<220> FEATURE:
<223> OTHER INFORMATION: Primer

<400> SEQUENCE: 57
gatcgtcgac tcaaaagagg cggacttctg cc                                32

<210> SEQ ID NO 58
<211> LENGTH: 30
<212> TYPE: DNA
<213> ORGANISM: Artificial sequence
<220> FEATURE:
<223> OTHER INFORMATION: Primer

<400> SEQUENCE: 58
gatcgtcgac tcatcccatt ataacaacac                                   30

<210> SEQ ID NO 59
<211> LENGTH: 30
<212> TYPE: DNA
<213> ORGANISM: Artificial sequence
<220> FEATURE:
<223> OTHER INFORMATION: Primer

<400> SEQUENCE: 59
aattgtcgac gggagatggg ggaggctaac                                   30

<210> SEQ ID NO 60
<211> LENGTH: 30
<212> TYPE: DNA
<213> ORGANISM: Artificial sequence
<220> FEATURE:
<223> OTHER INFORMATION: Primer

<400> SEQUENCE: 60
gagtacgcgt tgaacaaacg acccaacacc                                   30

<210> SEQ ID NO 61
<211> LENGTH: 27
<212> TYPE: DNA
<213> ORGANISM: Artificial sequence
<220> FEATURE:
<223> OTHER INFORMATION: Primer

<400> SEQUENCE: 61
gagaacgcgt gatagtacag gctttgc                                      27

<210> SEQ ID NO 62
<211> LENGTH: 29
<212> TYPE: DNA
<213> ORGANISM: Artificial sequence
<220> FEATURE:
<223> OTHER INFORMATION: Primer

<400> SEQUENCE: 62
cataacgcgt ttctgctctc aacaccgag                                    29

<210> SEQ ID NO 63
<211> LENGTH: 25
<212> TYPE: DNA
<213> ORGANISM: Artificial sequence
<220> FEATURE:
<223> OTHER INFORMATION: Primer

<400> SEQUENCE: 63
agaagctaat tcactaattg ccgac                                      25

<210> SEQ ID NO 64
<211> LENGTH: 2153
<212> TYPE: DNA
<213> ORGANISM: Artificial sequence
<220> FEATURE:
<223> OTHER INFORMATION: Amylase synthetic construct

<400> SEQUENCE: 64

```
gcgcgccgcg aaacggttag tataagcagt acgacgttgt tgctggagtc tcatctgcaa      60
ggttgagtac caatccctgc cccaatacga gcaatcgaag ccttggggaa agatgcggcg     120
ggctagcttc agcaataaat agcaggcgac acacaaaaat taggcggcaa gcgcacgctc     180
agcatgccat ctaccagggc aaaaagcaag gcaacctctt tttcgcatcc cgatttagag     240
cctacccgtc attgcagggt gtgcgtctac gatataacac gatcgacatc gcgctgggta     300
tgcttctggg taaggggtcg caacgtgtga gttgtcagca ctggccgata cccaaagtat     360
ataatgcgcc gttgaacggt tatagtcggt caagctctta agaaaagact taagaacaaa     420
aacaactgta cacatatgcg ttttcctagc attttttactg ctgttctttt cgctgctagc     480
agcgctcttg ctgctccagt taacactaca acagaggatg agactgctca gattccggct     540
gaggctgtta ttggttacag cgatcttgag ggcgatttcg atgttgctgt tcttccattt     600
agcaacagca caaataacgg ccttcttttt ataaatacta ctattgctag cattgctgct     660
aaggaggagg gcgtttctct tgataagcgt gctactcctg ctgactggcg ttcgcagagc     720
atttatttcc ttctcactga tcgttttgct cgtactgatg ctcgactac tgctacttgc     780
aatactgctg atcgtaagta ctgcggtgga acatggcagg gcattattga caagcttgac     840
tatattcagg gaatgggctt cacagctatt tggattaccc ccgttacagc tcagctgccc     900
cagaccaccg cttatggaga tgcttaccac ggctactggc agcaggatat ttactctctg     960
aacgagaact acggcactgc tgatgacctt aaggctctct cttcggctct tcacgagcgt    1020
ggcatgtatc ttatggttga tgttgttgct aaccacatgg gctatgatgg agctggtagc    1080
agcgttgatt actctgtttt taagccgttc tctagccagg actacttcca cccgttctgc    1140
ctcattcaga actatgagga tcagactcag gttgaggatt gctggctcgg agataacact    1200
gttagccttc ctgatctcga taccaccaag gatgttgtta agaatgagtg gtacgactgg    1260
gttggaagcc ttgtttcgaa ctacagcatt gacggcctcc gtattgacac agttaagcac    1320
gttcagaagg acttctggcc cggctacaac aaggctgctg gcgtttactg cattggcgag    1380
gttctcgacg gtgatccggc ttacacttgc ccctaccaga acgttatgga cggcgttctg    1440
aactatccca tttactatcc actcctcaac gcttttcaaga gcaccagcgg cagcatggac    1500
gacctctaca acatgattaa caccgttaag agcgactgcc cagacagcac actcctgggc    1560
acattcgttg agaaccacga caacccacgt ttcgcttctt acaccaacga cattgctctc    1620
gctaagaacg ttgctgcttt cattattctc aacgacggaa ttcccattat ttacgctggc    1680
caggagcagc actacgctgg cggaaacgac cccgctaacc gtgaggctac ctggctctcg    1740
ggctacccga ccgacagcga gctgtacaag cttattgcta cgctaacgc tattcgtaac    1800
tatgctatta gcaaggatac aggattcgtt acctacaaga actggcccat ttacaaggac    1860
gacacaacta ttgctatgcg taagggcaca gatggctcgc agattgttac tattcttagc    1920
aacaagggtg cttcgggtga ttcgtatacc ctcagccttt ctggtgctgg ttacacagct    1980
ggccagcagc ttactgaggt tattggctgc actaccgtta ctgttggttc ggatggaaat    2040
```

```
gttcctgttc ctatggctgg tggcctccct cgtgttcttt atccgactga gaagcttgct    2100
ggtagcaaga tttgctctag ctcgtgataa gcccgggcgc cggcgtacga tta           2153

<210> SEQ ID NO 65
<211> LENGTH: 563
<212> TYPE: PRT
<213> ORGANISM: Artificial sequence
<220> FEATURE:
<223> OTHER INFORMATION: Amylase synthetic construct

<400> SEQUENCE: 65

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Ala Thr Pro Ala Asp Trp Arg Ser Gln Ser Ile
                85                  90                  95

Tyr Phe Leu Leu Thr Asp Arg Phe Ala Arg Thr Asp Gly Ser Thr Thr
            100                 105                 110

Ala Thr Cys Asn Thr Ala Asp Arg Lys Tyr Cys Gly Gly Thr Trp Gln
        115                 120                 125

Gly Ile Ile Asp Lys Leu Asp Tyr Ile Gln Gly Met Gly Phe Thr Ala
130                 135                 140

Ile Trp Ile Thr Pro Val Thr Ala Gln Leu Pro Gln Thr Thr Ala Tyr
145                 150                 155                 160

Gly Asp Ala Tyr His Gly Tyr Trp Gln Gln Asp Ile Tyr Ser Leu Asn
                165                 170                 175

Glu Asn Tyr Gly Thr Ala Asp Asp Leu Lys Ala Leu Ser Ser Ala Leu
            180                 185                 190

His Glu Arg Gly Met Tyr Leu Met Val Asp Val Val Ala Asn His Met
        195                 200                 205

Gly Tyr Asp Gly Ala Gly Ser Ser Val Asp Tyr Ser Val Phe Lys Pro
    210                 215                 220

Phe Ser Ser Gln Asp Tyr Phe His Pro Phe Cys Leu Ile Gln Asn Tyr
225                 230                 235                 240

Glu Asp Gln Thr Gln Val Glu Asp Cys Trp Leu Gly Asp Asn Thr Val
                245                 250                 255

Ser Leu Pro Asp Leu Asp Thr Thr Lys Asp Val Val Lys Asn Glu Trp
            260                 265                 270

Tyr Asp Trp Val Gly Ser Leu Val Ser Asn Tyr Ser Ile Asp Gly Leu
        275                 280                 285

Arg Ile Asp Thr Val Lys His Val Gln Lys Asp Phe Trp Pro Gly Tyr
    290                 295                 300

Asn Lys Ala Ala Gly Val Tyr Cys Ile Gly Glu Val Leu Asp Gly Asp
305                 310                 315                 320

Pro Ala Tyr Thr Cys Pro Tyr Gln Asn Val Met Asp Gly Val Leu Asn
                325                 330                 335

Tyr Pro Ile Tyr Tyr Pro Leu Leu Asn Ala Phe Lys Ser Thr Ser Gly
```

```
                    340             345             350
Ser Met Asp Asp Leu Tyr Asn Met Ile Asn Thr Val Lys Ser Asp Cys
            355                 360                 365

Pro Asp Ser Thr Leu Leu Gly Thr Phe Val Glu Asn His Asp Asn Pro
        370                 375                 380

Arg Phe Ala Ser Tyr Thr Asn Asp Ile Ala Leu Ala Lys Asn Val Ala
385                 390                 395                 400

Ala Phe Ile Ile Leu Asn Asp Gly Ile Pro Ile Ile Tyr Ala Gly Gln
                405                 410                 415

Glu Gln His Tyr Ala Gly Gly Asn Asp Pro Ala Asn Arg Glu Ala Thr
            420                 425                 430

Trp Leu Ser Gly Tyr Pro Thr Asp Ser Glu Leu Tyr Lys Leu Ile Ala
            435                 440                 445

Ser Ala Asn Ala Ile Arg Asn Tyr Ala Ile Ser Lys Asp Thr Gly Phe
        450                 455                 460

Val Thr Tyr Lys Asn Trp Pro Ile Tyr Lys Asp Asp Thr Thr Ile Ala
465                 470                 475                 480

Met Arg Lys Gly Thr Asp Gly Ser Gln Ile Val Thr Ile Leu Ser Asn
                485                 490                 495

Lys Gly Ala Ser Gly Asp Ser Tyr Thr Leu Ser Leu Ser Gly Ala Gly
            500                 505                 510

Tyr Thr Ala Gly Gln Gln Leu Thr Glu Val Ile Gly Cys Thr Thr Val
            515                 520                 525

Thr Val Gly Ser Asp Gly Asn Val Pro Val Pro Met Ala Gly Gly Leu
        530                 535                 540

Pro Arg Val Leu Tyr Pro Thr Glu Lys Leu Ala Gly Ser Lys Ile Cys
545                 550                 555                 560

Ser Ser Ser

<210> SEQ ID NO 66
<211> LENGTH: 3043
<212> TYPE: DNA
<213> ORGANISM: Candida bombicola

<400> SEQUENCE: 66
ktttctcaac agacttagat gattcaatct aaattctgag tgataggttg agcattagca      60
cagtttggtt tagatagtaa ctgagttttcc cagtgacgaa actctaccta tggtgtaaga    120
gtcttgaggc tgaggttaca gcgactcaaa ctacagcgtg catgagaaac tcgctaatat    180
atattagggt tgatgcagct tgcatataga gtcgggcgtt atttctccgt ttatcatatt    240
gaaaagtaca tatatgttaa tcaaagacat tattctaact ccaatgagtt tatccgctgt    300
tgctggcttg ttgccactgc tcttcgtagc tttcttagtt ctacacgagc ctatctggct    360
cctatggtac cgctatgcag cacgtaggca caagtgtagt atgcctcgct tcattgagaa    420
atcgttccca ctgggaatac aaagaaccat ggacatgatc aagacggcca agtcatacac    480
cttactggaa gttcaatacg acagagtctt caataagttc aaagcacgga cgtatcttcg    540
acaagctccc cttcaatacc aaatcttcac aatcgagcca gaaaacatta agacaatcct    600
ggcaaccaaa ttcaatgatt ttggtcttgg agcacgtttc cacacagtgg aaaagtgtt    660
tggccaaggg atatttacac tcagcggaaa tggatggaaa cagtctcgat cgatgttgag    720
acctcagttc actaaagatc aggtttgcag aattgatcag atttccagtc atgctgcgga    780
gttaataaag gagatgaacc gtgcaatgaa agtggaccaa tttattgatg ttcaacatta    840
```

| | |
|---|---|
| tttccacaaa cttacgctgg atacagcgac tgaattccta tttggggagt cctgcgagag | 900 |
| cttgaaccct gagaatcagt catgtattgt agcccgtgat ggttcggaga ttactgccga | 960 |
| acaattcgtg gagtcctaca actttctact gaattacgct ttcaaacgga ccctatcaag | 1020 |
| caaagtctac tggttgttca actctaagga attccgagat cacaagaaac gtgctcagtc | 1080 |
| ctatattgac tactacgttg ataaggctct ttacgccaca tctttcgctg ctgagaactc | 1140 |
| tattgcagag aaggatgctg ctgcagagtc tagtggcatc tatgtgttct cgcttgagat | 1200 |
| ggctaaagtt acccgagacc cagtgacgat acgtgatcaa attttcaaca ttctcattgc | 1260 |
| tggtagagat acaacagctg ctacgttgag cttcgctatt catttccttg ccagaaatcc | 1320 |
| tgacgtattc aacaaactac gtgaggaggt cctcgatcat tttggaacca aggaggagca | 1380 |
| aaggccttta tcattcgaac ttctgaagca agcaccttat ttgaagcaag ttataaatga | 1440 |
| agtcttgcgt cttgcgccgg tattgccatt gaacttccgt actgctgtga gagatacaac | 1500 |
| tctacccata ggtggtggtc ccgagcgaaa ggatccgatc ttcgttccta agggcaccgc | 1560 |
| agtttactat tcaatttaca tggtccacag ggacatcaag tattggggtc ctgacgccca | 1620 |
| cgaattcaat cccaatcgat gggagaactt gaagctagat aatgtgtggg cattcttgcc | 1680 |
| cttcaatggc ggtccccgaa tttgtctcgg ccaacaattc gccctgacag gctttcgct | 1740 |
| aactctggtg agactcttac aggagtattc caagattgag atgggtcccg acttcccaga | 1800 |
| gtcccctcgt ttctcaacaa cgcttacagc tcaacacgct cctcccggtg tggttgtgcg | 1860 |
| gttttcttaa gtttcttagc ctcccatgga agaaacgttc cctccttaat tggttcaatc | 1920 |
| aacccatgtt aactcaacct gtggcaacct ttttattatt ctgagcactc tactcaagaa | 1980 |
| tggctgcagt tctttatttta tgctctttat gaagaatcat gtaaatcatg taaatcttga | 2040 |
| aggagtgcgt ttaaccgact attcttgaca tagaagcgac atctttacag ctcgaagtat | 2100 |
| acctcaatcc agaacaattg atggattatt cccacatgaa atcatttgat aggacaggat | 2160 |
| cgggccctcg ctccaatgaa taacagaacg cgcaagatac gtttgatcag gggtatacac | 2220 |
| ccgtgaattt gcgtgtggag atgcaccggc gatttgagag gccggcgaga gcaccaggtc | 2280 |
| ccatgtgagc gccgtcttct gttagaagaa tatggcatca gtcccgaaga tgagcagaaa | 2340 |
| ttattcgccc ataatggaat ggtgccagtt cctgagaaca aagggagcat cttattcaag | 2400 |
| gatgaggacc aatttgtcgt cacccacgac aacatacttg tccaatgtcg agacctgcga | 2460 |
| aaggacatga aagtgttctg cccggcctgt gagacgggcc attataccga caaattcagt | 2520 |
| ttcactatcc ccagggcgtc tgtcggtgtg tccagtggag tagtcgttta tgggattcgt | 2580 |
| catggtgaac tctcaatcag atgcttctct tcagacgatt ttggtaaata tactgcaatc | 2640 |
| gttgtgtgtg agttttttcga ccgtgaaatg aatgtaacta aactacaaaa agttgatctc | 2700 |
| gactttccag atcaactacg ggtaaatgca cccgtaggtt ttttgactcg cggtcgtttg | 2760 |
| gatccggggt ccatcctaca ccccattgaa acaaagtttt gattgtcaga ggagcttcac | 2820 |
| gcttttcgta tcatgatggg acagactcca aagctatcca tcgaacaatt ttytccgatg | 2880 |
| gaatttggcg agtcgacacc cttgtttcaa taagagtacc gaacaagagc gcaacaaatt | 2940 |
| tgtaactaat cgcaaacttg ctattagata cctctcggat gacaaaaata caagtttaca | 3000 |
| cacttggkgg tttaaatacc aattaacaaa agaaggaaa aag | 3043 |

<210> SEQ ID NO 67
<211> LENGTH: 538
<212> TYPE: PRT
<213> ORGANISM: Candida bombicola

<400> SEQUENCE: 67

Met Leu Ile Lys Asp Ile Ile Leu Thr Pro Met Ser Leu Ser Ala Val
1               5                   10                  15

Ala Gly Leu Leu Pro Leu Leu Phe Val Ala Phe Leu Val Leu His Glu
            20                  25                  30

Pro Ile Trp Leu Leu Trp Tyr Arg Tyr Ala Ala Arg Arg His Lys Cys
            35                  40                  45

Ser Met Pro Arg Phe Ile Glu Lys Ser Phe Pro Leu Gly Ile Gln Arg
    50                  55                  60

Thr Met Asp Met Ile Lys Thr Ala Lys Ser Tyr Thr Leu Leu Glu Val
65                  70                  75                  80

Gln Tyr Asp Arg Val Phe Asn Lys Phe Lys Ala Arg Thr Tyr Leu Arg
                85                  90                  95

Gln Ala Pro Leu Gln Tyr Gln Ile Phe Thr Ile Glu Pro Glu Asn Ile
            100                 105                 110

Lys Thr Ile Leu Ala Thr Lys Phe Asn Asp Phe Gly Leu Gly Ala Arg
            115                 120                 125

Phe His Thr Val Gly Lys Val Phe Gly Gln Gly Ile Phe Thr Leu Ser
        130                 135                 140

Gly Asn Gly Trp Lys Gln Ser Arg Ser Met Leu Arg Pro Gln Phe Thr
145                 150                 155                 160

Lys Asp Gln Val Cys Arg Ile Asp Gln Ile Ser Ser His Ala Ala Glu
                165                 170                 175

Leu Ile Lys Glu Met Asn Arg Ala Met Lys Val Asp Gln Phe Ile Asp
            180                 185                 190

Val Gln His Tyr Phe His Lys Leu Thr Leu Asp Thr Ala Thr Glu Phe
        195                 200                 205

Leu Phe Gly Glu Ser Cys Glu Ser Leu Asn Pro Glu Asn Gln Ser Cys
210                 215                 220

Ile Val Ala Arg Asp Gly Ser Glu Ile Thr Ala Glu Gln Phe Val Glu
225                 230                 235                 240

Ser Tyr Asn Phe Leu Leu Asn Tyr Ala Phe Lys Arg Thr Leu Ser Ser
                245                 250                 255

Lys Val Tyr Trp Leu Phe Asn Ser Lys Glu Phe Arg Asp His Lys Lys
            260                 265                 270

Arg Ala Gln Ser Tyr Ile Asp Tyr Val Asp Lys Ala Leu Tyr Ala
        275                 280                 285

Thr Ser Phe Ala Ala Glu Asn Ser Ile Ala Glu Lys Asp Ala Ala
        290                 295                 300

Glu Ser Ser Gly Ile Tyr Val Phe Ser Leu Glu Met Ala Lys Val Thr
305                 310                 315                 320

Arg Asp Pro Val Thr Ile Arg Asp Gln Ile Phe Asn Ile Leu Ile Ala
                325                 330                 335

Gly Arg Asp Thr Thr Ala Ala Thr Leu Ser Phe Ala Ile His Phe Leu
            340                 345                 350

Ala Arg Asn Pro Asp Val Phe Asn Lys Leu Arg Glu Val Leu Asp
        355                 360                 365

His Phe Gly Thr Lys Glu Glu Gln Arg Pro Leu Ser Phe Glu Leu Leu
        370                 375                 380

Lys Gln Ala Pro Tyr Leu Lys Gln Val Ile Asn Glu Val Leu Arg Leu
385                 390                 395                 400

Ala Pro Val Leu Pro Leu Asn Phe Arg Thr Ala Val Arg Asp Thr Thr

|   |   |   |   |   |   |   | 405 |   |   |   |   |   | 410 |   |   |   |   |   | 415 |   |
|---|---|---|---|---|---|---|---|---|---|---|---|---|---|---|---|---|---|---|---|---|
| Leu | Pro | Ile | Gly<br>420 | Gly | Gly | Pro | Glu | Gln<br>425 | Lys | Asp | Pro | Ile | Phe<br>430 | Val | Pro |
| Lys | Gly | Thr<br>435 | Ala | Val | Tyr | Tyr | Ser<br>440 | Ile | Tyr | Met | Val | His<br>445 | Arg | Asp | Ile |
| Lys | Tyr<br>450 | Trp | Gly | Pro | Asp | Ala<br>455 | His | Glu | Phe | Asn | Pro<br>460 | Asn | Arg | Trp | Glu |
| Asn<br>465 | Leu | Lys | Leu | Asp | Asn<br>470 | Val | Trp | Ala | Phe | Leu<br>475 | Pro | Phe | Asn | Gly | Gly<br>480 |
| Pro | Arg | Ile | Cys | Leu<br>485 | Gly | Gln | Gln | Phe | Ala<br>490 | Leu | Thr | Glu | Leu | Ser<br>495 | Leu |
| Thr | Leu | Val | Arg<br>500 | Leu | Leu | Gln | Glu | Tyr<br>505 | Ser | Lys | Ile | Glu | Met<br>510 | Gly | Pro |
| Asp | Phe | Pro<br>515 | Glu | Ser | Pro | Arg | Phe<br>520 | Ser | Thr | Thr | Leu | Thr<br>525 | Ala | Gln | His |
| Ala | Pro<br>530 | Pro | Gly | Val | Val<br>535 | Val | Arg | Phe | Ser |

What is claimed is:

1. A method of producing one or more compounds by fermentation comprising culturing a modified *Candida bombicola* strain to produce the one or more compounds, wherein said *Candida bombicola* strain has, compared to the unmodified wild-type strain:
   a) at least one deletion in an endogenous gene encoding an enzyme selected from the group consisting of the cytochrome P450 monooxygenase CYP52M1 having the sequence of SEQ ID NO: 67, the glucosyltransferase UGTA1 having sequence of SEQ ID NO: 2, and the glucosyltransferase UGTB1 having the sequence of SEQ ID NO: 4, and
   b) a reduction in its capability of producing sophorolipids of at least 75%, and wherein said sophorolipids are constituted of the sugar sophorose attached to a $C_{16}$, $C_{18}$, $C_{22}$ or $C_{24}$ hydroxylated fatty acid.

2. The method according to claim 1 wherein said one or more compounds are selected from the group consisting of recombinant proteins, beta-hydroxy fatty acids and polyhydroxyalkanoates, dicarboxylic acids, polyunsaturated fatty acids, hydroxylated fatty acids, glycolipids, glucolipids, trehaloselipids rhamnolipids, sophorolipids with a fatty acid tail ranging from 10 to 15 carbon atoms, sophorolipids with a fatty acid tail of 17 carbon atoms, sophorolipids with a fatty acid tail ranging from 19 to 25 carbon atoms, sophorolipids with branched fatty acid tail, sophorolipids with multiple hydroxylated fatty acid tails, fully lactonized sophorolipids and fully acidic sophorolipids, rhamnose, sophorose, polyketide antibiotics, fatty acid based lactonic structures, organic acids, oleagenious compounds, hydrophobic compounds, squaleen, vitamin D, resveratrol, steroids, and carotenoides.

3. The method according to claim 1, wherein said reduction in its capability of producing sophorolipids is 100%.

4. The method according to claim 1, wherein said *Candida bombicola* is the strain *Candida bombicola* ATCC 22214.

\* \* \* \* \*